US012746207B2

(12) United States Patent
Koana et al.

(10) Patent No.: US 12,746,207 B2
(45) Date of Patent: Sep. 29, 2026

(54) LIPID AND COMPOSITION

(71) Applicants: SOGO PHARMACEUTICAL CO., LTD., Tokyo (JP); SHIZUOKA PREFECTURAL UNIVERSITY CORPORATION, Shizuoka (JP)

(72) Inventors: Tetsuo Koana, Tokyo (JP); Jun Hayashida, Tokyo (JP); Toshinori Takaki, Tokyo (JP); Yohei Tanaka, Tokyo (JP); Nahoko Ozaki, Tokyo (JP); Tomohiro Asai, Shizuoka (JP)

(73) Assignees: SOGO PHARMACEUTICAL CO., LTD., Tokyo (JP); SHIZUOKA PREFECTURAL UNIVERSITY CORPORATION, Shizuoka (JP)

( * ) Notice: Subject to any disclaimer, the term of this patent is extended or adjusted under 35 U.S.C. 154(b) by 378 days.

(21) Appl. No.: 18/285,991

(22) PCT Filed: Apr. 11, 2022

(86) PCT No.: PCT/JP2022/017539
§ 371 (c)(1),
(2) Date: Nov. 28, 2023

(87) PCT Pub. No.: WO2022/215758
PCT Pub. Date: Oct. 13, 2022

(65) Prior Publication Data

US 2024/0148664 A1 May 9, 2024

(30) Foreign Application Priority Data

Apr. 9, 2021 (JP) ................................ 2021-066762

(51) Int. Cl.
*A61K 47/44* (2017.01)
*A61K 9/51* (2006.01)

(52) U.S. Cl.
CPC ............ *A61K 9/5123* (2013.01); *A61K 47/44* (2013.01)

(58) Field of Classification Search
CPC .... A61K 9/5123; A61K 47/44; A61K 9/0019; A61K 47/14; A61K 48/0041; A61K 31/713; C07K 5/06086; C07K 5/06095; C12N 15/111; C12N 2310/14; C12N 15/88; C12N 15/113
See application file for complete search history.

(56) References Cited

U.S. PATENT DOCUMENTS

2010/0209458 A1 8/2010 Takeoka et al.

FOREIGN PATENT DOCUMENTS

| | | | |
|---|---|---|---|
| CN | 102532259 | A | 7/2012 |
| CN | 111087317 | A | 5/2020 |
| JP | 2005-519966 | A | 7/2005 |
| JP | 2009-528258 | A | 8/2009 |
| JP | 2012-508261 | A | 4/2012 |
| JP | 2012-530059 | A | 11/2012 |
| JP | 2016-514109 | A | 5/2016 |
| WO | WO 03/078383 | A1 | 9/2003 |
| WO | WO 2007/099650 | A1 | 9/2007 |
| WO | WO 2008/143339 | A1 | 11/2008 |
| WO | WO 2010/054401 | A1 | 5/2010 |
| WO | WO 2010/144740 | A1 | 12/2010 |
| WO | WO 2011/153493 | A2 | 12/2011 |
| WO | WO 2013/086354 | A1 | 6/2013 |
| WO | WO 2013/158579 | A1 | 10/2013 |
| WO | WO 2014/136086 | A1 | 9/2014 |

OTHER PUBLICATIONS

International Search Report for PCT/JP2022/017539 (PCT/ISA/210) mailed on Jun. 14, 2022.

Miao et al., "Delivery of mRNA vaccines with heterocyclic lipids increases anti-tumor efficacy by STING-mediated immune cell activation", Nature Biotechnology, vol. 37, Oct. 2019, pp. 1174-1185.

International Preliminary Report on Patentability and Written Opinion of the International Searching Authority (Forms PCT/IB/338, PCT/IB/373 and PCT/ISA/237) for International Application No. PCT/JP2022/017539, dated Oct. 19, 2023.

*Primary Examiner* — Jessica Worsham

(74) *Attorney, Agent, or Firm* — Birch, Stewart, Kolasch & Birch, LLP

(57) ABSTRACT

Provided are a lipid and a composition that can effectively deliver an introduction compound such as a nucleic acid to a target cell, tissue, or the like in vivo. The lipid of the present invention is a lipid represented by the following formula (I), wherein $R^1$ is a hydrocarbon group having 32 to 48 carbon atoms, $R^2$ is a side chain of one arbitrary amino acid or a side chain of a derivative of the amino acid, and $R^3$ is a side chain of a basic amino acid or a side chain of a derivative of the amino acid, (I)

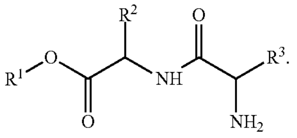

20 Claims, No Drawings

LIPID AND COMPOSITION

FIELD OF THE INVENTION

The present invention relates to a lipid and a composition.

BACKGROUND OF THE INVENTION

Delivery of a compound (for example, nucleoside, nucleotide, polynucleotide, nucleic acid, and derivative thereof, such as bioactive drug, including RNAi agent) into a subject such as a target cell or tissue in vivo generally uses a carrier molecule such as a lipid. However, in some cases, for example, a carrier molecule is degraded by a degradative enzyme in vivo, or the permeation of the cell membrane is restricted, making it difficult to deliver the compound to the subject. In addition, if the compound can be delivered to the subject, but not efficiently, it may require the use of a higher dosage than the desired dosage of an introduction compound in order to obtain the desired effect of the compound, and this may increase the risk of a cytotoxic action and a side effect. Therefore, there is a need for a carrier molecule that can efficient entry into a target cell or tissue.

In response to such problems, for example, Patent Literature 1 discloses that encapsulation of an siRNA as a nucleic acid in a lipid-containing microparticle protects the encapsulated siRNA from degradation in plasma and enables permeation thereof through a lipophilic cell membrane. In addition, Patent Literatures 2 to 4 disclose a lipid having improved biodegradability that is used for delivery of a nucleic acid drug such as an siRNA. Patent Literature 5 discloses a cationic lipid compound for delivery of a bioactive drug such as an RNAi agent.

PRIOR ART

Patent Literature

[Patent Literature 1] PCT International Application Publication No. 2012-530059

[Patent Literature 2] International Publication No. WO 2011/153493

[Patent Literature 3] International Publication No. WO 2013/086354

[Patent Literature 4] International Publication No. WO 2013/158579

[Patent Literature 5] Japanese Patent Laid-Open No. 2016-514109

SUMMARY OF THE INVENTION

Technical Problem

However, despite recent advances, there is still a need for a lipid that can effectively deliver a compound to be introduced into a subject such as a target cell or tissue in vivo (hereinafter also referred to as an introduction compound) into the subject.

Therefore, an object of the present invention is to provide a lipid and a composition that can effectively deliver an introduction compound such as a nucleic acid to a target cell, tissue, or the like in vivo.

Solution to Problem

The lipid of the present invention is a lipid represented by the following formula (I):

[Formula 1]

(I)

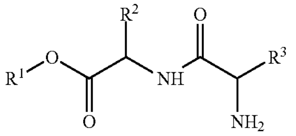

wherein $R^1$ is a hydrocarbon group having 32 to 48 carbon atoms, $R^2$ is a side chain of one arbitrary amino acid or a side chain of a derivative of the amino acid, and $R^3$ is a side chain of a basic amino acid or a side chain of a derivative of the amino acid.

In addition, the composition of the present invention is a composition of the lipid and an introduction compound.

Advantageous Effects of Invention

According to the present invention, it is possible to provide a lipid and a composition that can effectively deliver an introduction compound such as a nucleic acid to a target cell, tissue, or the like in vivo.

DETAILED DESCRIPTION OF THE INVENTION

[Lipid]

Hereinafter, an embodiment of the present invention will be described with reference to examples thereof.

The lipid of the present embodiment is represented by the following formula (I).

[Formula 2]

(I)

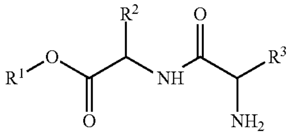

wherein $R^1$ is a hydrocarbon group having 32 to 48 carbon atoms, $R^2$ is a side chain of one arbitrary amino acid or a side chain of a derivative of the amino acid, and $R^3$ is a side chain of a basic amino acid or a side chain of a derivative of the amino acid.

More specifically, the lipid of the present embodiment may be amphiphilic molecule having a lipophilic region (tail) including a hydrocarbon group ($R^1$) and a hydrophilic region (head) including two amino acids or derivatives thereof (dipeptides) linked to the hydrocarbon by an ester bond.

For the two amino acid moieties (residues) of the hydrophilic region, amino acids, or derivatives of the amino acids, corresponding to the first and second amino acid moieties from the lipophilic region are also referred to as the first amino acid and the second amino acid, respectively.

According to the lipid of the present embodiment, an introduction compound such as a nucleic acid can be effectively delivered to a target cell, tissue, or the like in vivo.

Specifically, the hydrophilic region of the lipid of the present embodiment is formed by two amino acid-derived moieties, and thus the influence of the lipid of the present embodiment on the living body can be appropriately suppressed. In addition, in the lipid of the present embodiment, the terminal ($R^3$) side of the hydrophilic region is derived from a basic amino acid and has a moderate cationic property, and a lipid nanoparticle such as a liposome including the lipid can be easily produced in a state in which an introduction compound into a cell such as a nucleic acid is encapsulated, and in addition, the lipid nanoparticle can be caused to easily permeate the cell membrane of a cell. Further, such a hydrophilic region in the lipid of the present embodiment can improve the compatibility between a lipid nanoparticle such as a liposome and an intracellular introduction compound.

Further, by including a hydrocarbon group ($R^1$) having 32 to 48 carbon atoms in the lipophilic region, it is possible to appropriately form a membrane of a lipid nanoparticle such as a liposome while ensuring the stability and the like of the membrane.

As described above, by using the lipid of the present embodiment, an introduction compound such as a nucleic acid can be effectively delivered to a target cell, tissue, or the like in vivo.

The lipid of the present embodiment also includes, in addition to the compound represented by formula (I), a pharmaceutically acceptable salt thereof. The pharmaceutically acceptable salt refers to a salt that retains the biological effectiveness and the properties of the compound of the present invention and is typically not biologically or otherwise undesirable.

More specifically, in the lipid of the present embodiment, for example, the hydrophilic region can be protonated to form a cation or deprotonated to form an anion. An anion that can be paired with a cation of the lipid is not particularly limited as long as the anion is pharmaceutically acceptable, and examples thereof include an inorganic ion such as a chloride ion, a bromide ion, a nitrate ion, a sulfate ion, or a phosphate ion; and an organic acid ion such as an acetate ion, an oxalate ion, a maleate ion, a fumarate ion, a citrate ion, a benzoate ion, a methanesulfonate ion, or a trifluoroacetate ion. In addition, a cation that is paired with an anion of the lipid is not particularly limited as long as the cation is pharmaceutically acceptable, and examples thereof include an ammonium ion, a trialkylammonium ion, a sodium ion, a potassium ion, a magnesium ion, or a calcium ion.

Here, in the present embodiment, $R^1$ in formula (I) is a hydrocarbon group having 32 to 48 carbon atoms. By setting the number of carbon atoms in the hydrocarbon group to 32 to 48, the stability of the membrane of a lipid nanoparticle such as a liposome can be improved, and the membrane itself can be prevented from becoming too large.

Here, examples of the "hydrocarbon group" include an alkyl group, a cycloalkyl group, an alkenyl group, a cycloalkenyl group, an alkynyl group, an aryl group, an aralkyl group, and a cycloalkylalkyl group, and the hydrocarbon group is preferably an alkyl group, an alkenyl group, or an alkynyl group.

$R^1$ may be a branched hydrocarbon group or a linear hydrocarbon group, and is preferably branched. In addition, the number of carbon atoms in $R^1$ is preferably 32 to 46, more preferably 32 to 44, and further preferably 36 to 44. This can further improve the stability of the membrane of the lipid nanoparticle and further prevent the membrane itself from becoming too large.

Further, in the present embodiment, the hydrocarbon group of $R^1$ may be saturated and is preferably unsaturated, and the unsaturated bond is more preferably a cis type.

In the present embodiment, $R^1$ is preferably a hydrocarbon group represented by the following formula (II).

[Formula 3]

(II)

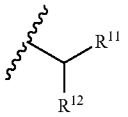

wherein $R^{11}$ is a hydrocarbon group having a carbon atoms, and $R^{12}$ is a hydrocarbon group having b carbon atoms, where a and b satisfy $31 \leq a+b \leq 47$.

$R^1$ and $R^{12}$ are not particularly limited, may each be, for example, a linear hydrocarbon group, and are each preferably a linear hydrocarbon group having 1 to 46 carbon atoms. $R^1$ and $R^{12}$ are each more preferably a linear hydrocarbon group having 6 to 22 carbon atoms, more preferably a linear hydrocarbon group having 10 to 22 carbon atoms, further preferably a linear hydrocarbon group having 17 to 22 carbon atoms, and more further preferably a linear hydrocarbon group having 18 to 22 carbon atoms. This can further improve the stability of the membrane of the lipid nanoparticle and further prevent the membrane itself from becoming too large.

$R^1$ and $R^{12}$ are each a hydrocarbon group having the above number of carbon atoms, and at least one thereof is preferably an unsaturated hydrocarbon group. In addition, further preferably, $R^1$ and $R^{12}$ are each an unsaturated hydrocarbon group having the above number of carbon atoms. In addition, when at least one of $R^1$ and $R^{12}$ is an unsaturated hydrocarbon group, the number of unsaturated bonds in one unsaturated hydrocarbon group is preferably three or less, and more preferably two or less, and most preferably one.

In addition, when $R^{11}$ and $R^{12}$ are each an unsaturated hydrocarbon group, the position of the unsaturated group from the terminal carbon in $R^{11}$ and $R^{12}$ is preferably the same between $R^{11}$ and $R^{12}$.

In addition, the number a of carbon atoms for $R^{11}$ and the number b of carbon atoms for $R^{12}$ satisfy preferably $1 \leq b-a \leq 20$, more preferably $1 \leq b-a \leq 18$, further preferably $1 \leq b-a \leq 15$, more further preferably $1 \leq b-a \leq 10$, and most preferably $1=b-a$.

Further, the numbers a and b of carbon atoms satisfy preferably $31 \leq a+b \leq 45$, more preferably $31 \leq a+b \leq 43$, and further preferably $35 \leq a+b \leq 43$.

$R^{11}$ and $R^{12}$ are not particularly limited, and examples thereof preferably include a linear saturated hydrocarbon groups having 10 to 22 carbon atoms (that is, n-decyl, n-undecyl, n-dodecyl, n-tridecyl, n-tetradecyl, n-pentadecyl, n-hexadecyl, n-heptadecyl, n-octadecyl, n-nonadecyl, or n-eicosyl) or a linear unsaturated hydrocarbon group having 10 to 22 carbon atoms (for example, a monounsaturated hydrocarbon group such as cis-9-tetradecen-1-yl, cis-8-pentadecen-1-yl, cis-9-hexadecen-1-yl, cis-8-heptadecen-1-yl, cis-9-octadecen-1-yl, cis-8-nonadecen-1-yl, cis-11-octadecen-1-yl, cis-9-eicosen-1-yl, cis-11-eicosen-1-yl, cis-12-henicosen-1-yl, or cis-13-docosen-1-yl, a di-unsaturated hydrocarbon group such as cis-8-cis-11-heptadecdien-1-yl, or cis-9-cis-12-octadecdien-1-yl, a tri-unsaturated hydrocarbon group such as cis-8-cis-11-cis-14-heptadectrien-1-yl, cis-9-cis-12-cis-15-octadectrien-1-yl, cis-8-cis-10-cis-12-heptadectrien-1-yl, or cis-9-cis-11-cis-13-octadectrien-1-yl, or a tetra-unsaturated hydrocarbon group such as cis-3-cis-7-cis-11-cis-14-heptadectetraen-1-yl, cis-4-cis-8-cis-12-cis-15-octadectetraen-1-yl, cis-4-cis-7-cis-10-cis-13-nonadectetraen-1-yl, or cis-5-cis-8-cis-11-cis-14-eicosatetraen-1-yl).

$R^{11}$ and $R^{12}$ are each preferably a linear unsaturated hydrocarbon group having 16 to 24 carbon atoms, and more preferably a linear unsaturated hydrocarbon group having 18 to 22 carbon atoms, further preferably $R^{11}$ is cis-8-heptadecen-1-yl, cis-8-cis-11-heptadecdien-1-yl, or cis-12-henicosen-1-yl, and $R^{12}$ is cis-9-octadecen-1-yl, cis-9-cis-12-octadecdien-1-yl, or cis-13-docosen-1-yl, and most preferably $R^{11}$ is cis-8-heptadecen-1-yl, and $R^{12}$ is cis-9-octadecen-1-yl.

In the present embodiment, $R^2$ in formula (I) is a side chain of one arbitrary amino acid or a side chain of a derivative of the amino acid. Examples of the amino acid include 20 natural amino acids (Gly, Ala, Leu, lie, Val, Arg, Lys, Glu, Gln, Asp, Asn, Cys, Met, His, Pro, Phe, Tyr, Thr, Ser, and Trp), and modified and unnatural amino acids (for example, 2-aminoadipic acid, 3-aminoadipic acid, p-alanine, 2-aminobutyric acid, 4-aminobutyric acid, 5-aminovaleric acid, 6-aminocaproic acid, 2-aminoheptanoic acid, 2,3-diaminopropionic acid, N-ethylglycine, N-ethylasparagine, hydroxylysine, norvaline, norleucine, ornithine, 2-aminopimelic acid, 2-aminosuberic acid, homoserine, aminomalonic acid, homoarginine, glycocyamine, 2,4-diaminobutyric acid, or aminophenylalanine).

Preferably, $R^2$ is a side chain of a hydrophilic amino acid or a side chain of a derivative of the hydrophilic amino acid. This can more effectively deliver an introduction compound such as a nucleic acid to a target cell, tissue, or the like in vivo. The hydrophilic amino acid is not particularly limited, and examples thereof include serine, threonine, asparagine, glutamine, arginine, histidine, lysine, aspartic acid, glutamic acid, tyrosine, cysteine, 2-aminoadipic acid, 2-aminopimelic acid, 2-aminosuberic acid, homoserine, and aminomalonic acid.

In addition, $R^2$ is preferably a side chain of an amino acid selected from the group consisting of aspartic acid, glutamic acid, histidine, serine, and threonine, or a side chain of a derivative of the amino acid, and $R^2$ is more preferably a side chain of an amino acid selected from the group consisting of aspartic acid, glutamic acid, histidine, serine, and threonine. This can more effectively deliver an introduction compound such as a nucleic acid to a target cell, tissue, or the like in vivo.

Further, $R^2$ is preferably a side chain of an amino acid selected from the group consisting of aspartic acid, glutamic acid, histidine, and threonine, or a side chain of a derivative of the amino acid, and $R^2$ is more preferably a side chain of aspartic acid, glutamic acid, histidine, and threonine. This can effectively deliver an introduction compound such as a nucleic acid to the cytoplasm while further suppressing cytotoxicity.

When $R^2$ is a side chain of a derivative of a hydrophilic amino acid, the derivative of the hydrophilic amino acid preferably also exhibits hydrophilicity, and can exhibit hydrophilicity by, for example, having a polar group or a functional group that can have an electric charge.

Examples of the side chain of a derivative of an amino acid include one having (i) a $-NH_2$ group replaced with a $-NHR^4$ or $-N(R^4)_2$ group, where each $R^4$ is independently alkyl, cycloalkyl, heterocycloalkyl, aryl, alkylaryl, arylalkyl, or heteroaryl, which may be substituted or unsubstituted, (ii) a $-OH$ group replaced with a $-O-PO_3H_2$, $-OR^4$, or $-OCOR^4$ group, where each $R^4$ is independently alkyl, cycloalkyl, heterocycloalkyl, aryl, alkylaryl, arylalkyl, or heteroaryl, which may be substituted or unsubstituted, (iii) a $-COOH$ group replaced with a $-COOR^4$ group, wherein each $R^4$ is independently alkyl, cycloalkyl, heterocycloalkyl, aryl, alkylaryl, arylalkyl, or heteroaryl, which may be substituted or unsubstituted, (iv) a $-COOH$ group replaced with a $-CON(R^4)_2$ group, where each $R^4$ may independently be H or is independently alkyl, cycloalkyl, heterocycloalkyl, aryl, alkylaryl, arylalkyl, or heteroaryl, which may be substituted or unsubstituted, (v) a $-SH$ group replaced with $-S-S-CH_2-CH(NH_2)-COOH$ or $-S-S-CH_2-CH_2-CH(NH_2)-COOH$, (vi) a $-CH_2-$ group replaced with a $-CH(NH_2)-$, $-CH(OH)-$, or $-CHR^4-$ group, where each $R^4$ may independently be H or is independently alkyl, cycloalkyl, heterocycloalkyl, aryl, alkylaryl, arylalkyl, or heteroaryl, which may be substituted or unsubstituted, (vii) a $-CH_3$ group replaced with a $-CH_2-NH_2$, $-CH_2-OH$, or $-CH_2R^4$ group, wherein each $R^4$ is independently an alkyl, cycloalkyl, heterocycloalkyl, aryl, alkylaryl, arylalkyl, or heteroaryl, which may be substituted or unsubstituted, and/or (viii) H bonded to a carbon atom, replaced with halogen.

In addition, $R^4$ above is preferably alkyl, more preferably alkyl having 1 to 6 carbon atoms, further preferably alkyl having 1 to 3 carbon atoms, and more further preferably alkyl having 1 carbon atom.

In addition, herein, an amino acid includes an L form, a D form, and also a racemic form, and an L form is preferable.

When $R^2$ is a side chain of a derivative of an amino acid selected from the group consisting of aspartic acid, glutamic acid, histidine, methionine, serine, and threonine, examples of a side chain of a derivative of aspartic acid, glutamic acid, histidine, methionine, serine, and threonine include the following. That is, when $R^2$ is aspartic acid or glutamic acid, examples of a side chain of a derivative include one having (iii) a $-COOH$ group replaced with a $-COOR^4$ group, (vi) a $-CH_2-$ group replaced with a $-CH(NH_2)-$, $-CH(OH)-$, or $-CHR^4-$ group, and/or (viii) H bonded to a carbon atom, replaced with halogen.

In addition, when $R^2$ is histidine or methionine, examples of a side chain of a derivative include one having (vi) a $-CH_2-$ group replaced with a $-CH(NH_2)-$, $-CH(OH)-$, or $-CHR^4-$ group, and/or (viii) H bonded to a carbon atom, replaced with halogen.

Further, when $R^2$ is serine, examples of a side chain of a derivative include one having (ii) a —OH group replaced with a —O—$PO_3H^2$, —$OR^4$, or —$OCOR^4$ group, (vi) a —$CH_2$— group replaced with a —$CH(NH_2)$—, —CH(OH)—, or —$CHR^4$— group, and/or (viii) H bonded to a carbon atom, replaced with halogen.

In addition, when $R^2$ is threonine, examples of a side chain of a derivative include one having (ii) a —OH group replaced with a —O—$PO_3H^2$, —$OR^4$, or —$OCOR^4$ group, (vii) a —$CH_3$ group replaced with a —$CH_2$—$NH_2$, —$CH_2$—OH, or —$CH_2R^4$ group, and/or (viii) H bonded to a carbon atom, replaced with halogen. The side chain of a derivative of any of the above amino acids is preferably one having (vi) a —$CH_2$— group replaced with a —CH($NH_2$)—, —CH(OH)—, or —$CHR^4$— group (in the case of threonine, (vii) a —$CH_3$ group replaced with a —$CH_2$—$NH_2$, —$CH_2$—OH, or —$CH_2R^4$ group), and more preferably one having a —$CH_2$— group replaced with a —$CHR^4$— group (in the case of threonine, a —$CH_3$ group replaced with a —$CH_2R^4$ group).

In addition, $R^4$ above may be H or is alkyl, cycloalkyl, heterocycloalkyl, aryl, alkylaryl, arylalkyl, or heteroaryl, which may be substituted or unsubstituted. In addition, when a plurality of $R^4$ are present in the molecule, these are independently of each other selected from the above. Further, $R^4$ is preferably alkyl, more preferably alkyl having 1 to 6 carbon atoms, further preferably alkyl having 1 to 3 carbon atoms, and more further preferably alkyl having 1 carbon atom.

In the present embodiment, $R^3$ in formula (I) is a side chain of a basic amino acid or a side chain of a derivative of the basic amino acid, and $R^3$ is preferably a side chain of a basic amino acid. $R^3$ is more preferably a side chain of an amino acid selected from the group consisting of lysine, histidine, and arginine, or a side chain of a derivative of the amino acid, and $R^3$ is further preferably a side chain of an amino acid selected from the group consisting of lysine, histidine, and arginine. In addition, $R^3$ is more preferably a side chain of arginine or a side chain of a derivative of arginine, and $R^3$ is further preferably a side chain of arginine.

By doing so, an introduction compound such as a nucleic acid can be effectively delivered to the cytoplasm.

Examples of the basic amino acid include an amino acid having a residue exhibiting basicity among natural amino acids and modified and unnatural amino acids, and specific examples thereof include, but are not limited to, lysine, histidine, arginine, homoarginine, glycocyamine, ornithine, 2,4-diaminobutyric acid, 2,3-diaminopropionic acid, and aminophenylalanine.

When $R^3$ is a side chain of a derivative of a basic amino acid, the side chain thereof may be a side chain having any of (i) to (viii) listed above as a side chain of a derivative of an amino acid. In addition, in this case, $R^4$ is preferably alkyl, more preferably alkyl having 1 to 6 carbon atoms, further preferably alkyl having 1 to 3 carbon atoms, and more further preferably alkyl having 1 carbon atom.

When $R^3$ is a side chain of a derivative of a basic amino acid, the derivative of the basic amino acid preferably also exhibits basicity, and can exhibit basicity by, for example, having an amino group or a functional group that can accept a proton.

When $R^3$ is a side chain of a derivative of an amino acid selected from the group consisting of lysine, histidine, and arginine, examples of the side chain of a derivative of lysine, histidine, and arginine include the following.

That is, when $R^3$ is lysine, examples of the side chain of a derivative include one having (i) a —$NH_2$ group replaced with a —$NHR^4$ or —N(R) group, and/or (vi) a —$CH_2$— group replaced with a —$CH(NH_2)$—, —CH(OH)—, or —$CHR^4$— group.

In addition, when $R^3$ is histidine, examples of the side chain of a derivative include one having (vi) a —$CH_2$— group replaced with a —$CH(NH_2)$—, —CH(OH)—, or —$CHR^4$— group.

Further, when $R^3$ is arginine, examples of the side chain of a derivative include one having (vi) a —$CH_2$— group replaced with a —$CH(NH_2)$—, —CH(OH)—, or —$CHR^4$— group.

The side chain of a derivative of any of the above amino acids is preferably one having (vi) a —$CH_2$— group replaced with a —$CH(NH_2)$—, —CH(OH)—, or —$CHR^4$— group, and more preferably one having —$CH_2$— group replaced with a —$CHR^4$— group.

In addition, $R^4$ above may be H or is alkyl, cycloalkyl, heterocycloalkyl, aryl, alkylaryl, arylalkyl, or heteroaryl, which may be substituted or unsubstituted. In addition, when a plurality of $R^4$ are present in the molecule, these are independently of each other selected from the above. Further, $R^4$ is preferably alkyl, more preferably alkyl having 1 to 6 carbon atoms, further preferably alkyl having 1 to 3 carbon atoms, and more further preferably alkyl having 1 carbon atom.

In the present embodiment, preferably, $R^2$ in formula (I) is a side chain of an amino acid selected from the group consisting of aspartic acid, glutamic acid, histidine, serine, and threonine or a side chain of a derivative of the amino acid, and $R^3$ is a side chain of an amino acid selected from the group consisting of lysine, histidine, and arginine, or a side chain of a derivative of the amino acid, and more preferably, $R^2$ in formula (I) is a side chain of an amino acid selected from the group consisting of aspartic acid, glutamic acid, histidine, serine, and threonine, and $R^3$ is a side chain of an amino acid selected from the group consisting of lysine, histidine, and arginine.

In addition, preferably, $R^2$ in formula (I) is a side chain of an amino acid selected from the group consisting of aspartic acid, glutamic acid, histidine, and threonine or a side chain of a derivative of the amino acid, and $R^3$ is a side chain of arginine, or a side chain of a derivative of arginine, and more preferably, $R^2$ in formula (I) is a side chain of an amino acid selected from the group consisting of aspartic acid, glutamic acid, histidine, and threonine, and $R^3$ is a side chain of arginine.

Specific examples of the lipid represented by formula (I) above include, but are not limited to, lipids represented by the following formulas (Ia) to (II). In addition, among the lipids represented by the following formulas (Ia) to (II), formulas (Ia), (Ib), (Ie), and (II) are more preferable.

[Formula 4]
(Ia)
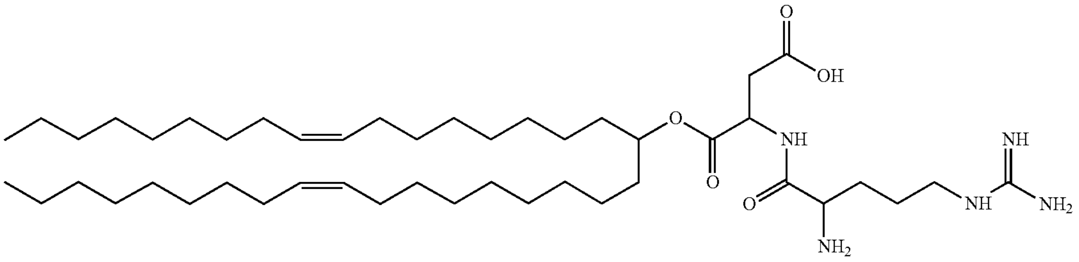
[Formula 5]
(Ib)
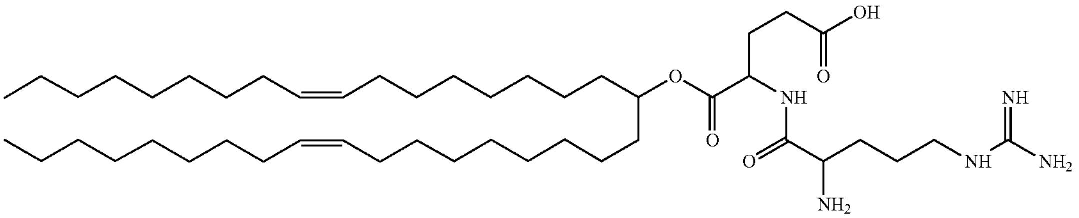
[Formula 6]
(Ic)
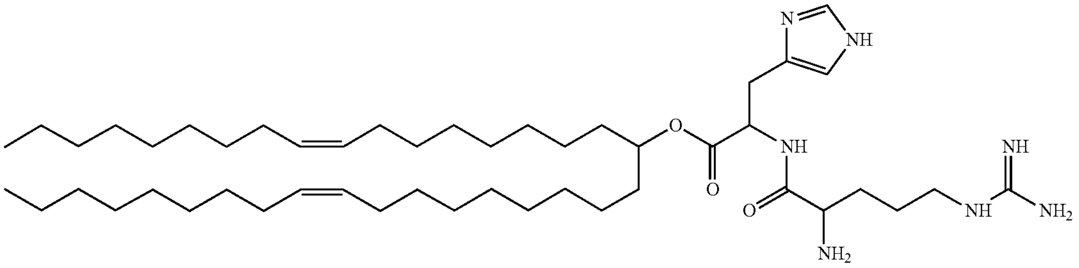
[Formula 7]
(Id)
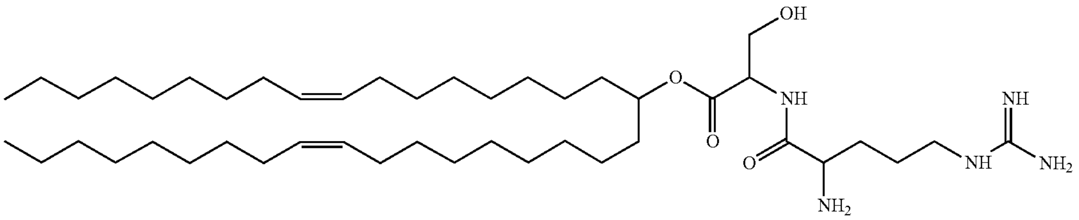
[Formula 8]
(Ie)
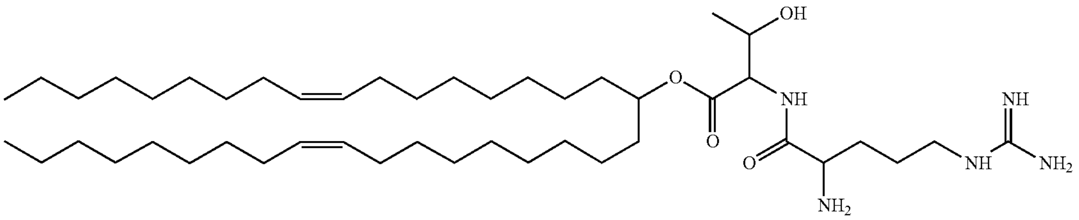

-continued
[Formula 9]
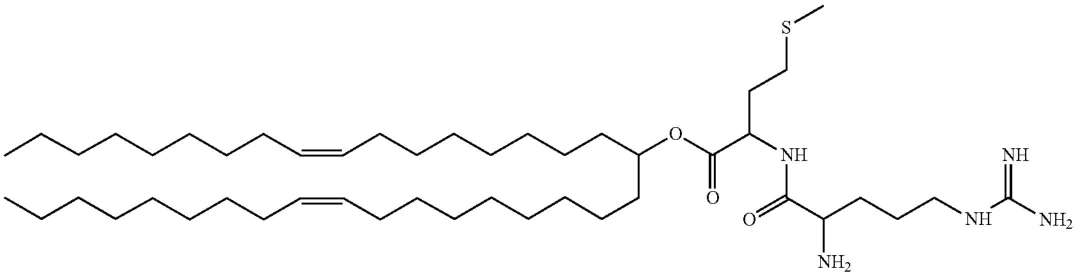
(If)
[Formula 10]
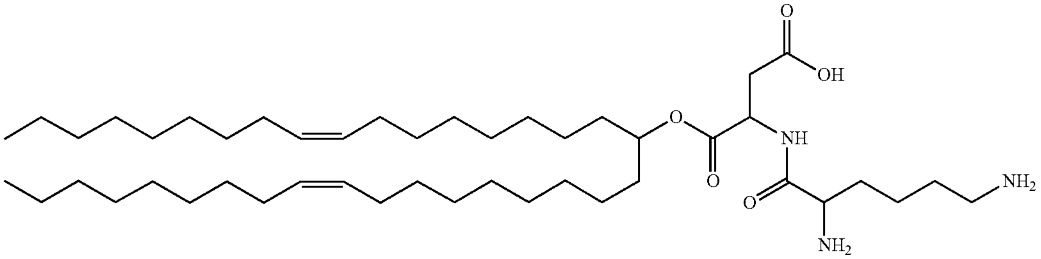
(Ig)
[Formula 11]
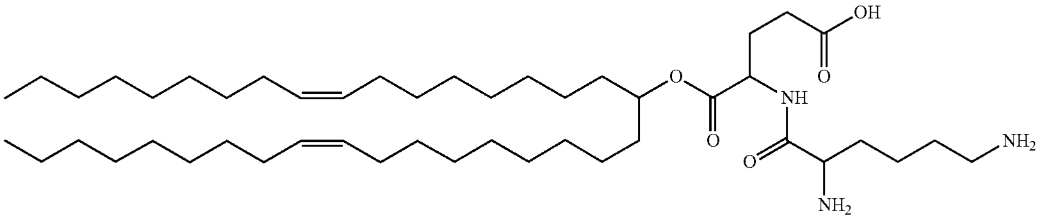
(Ih)
[Formula 12]
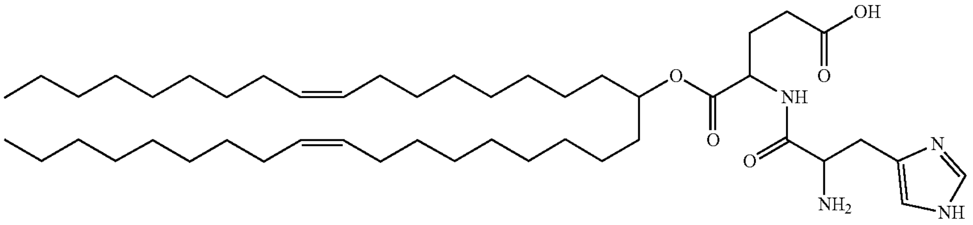
(Ii)
[Formula 13]
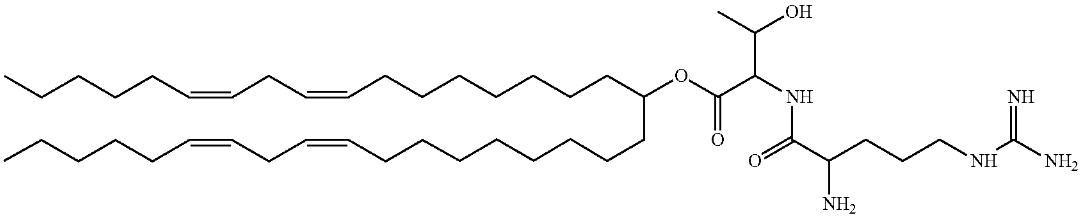
(Ij)

-continued

[Formula 14]

(Ik)

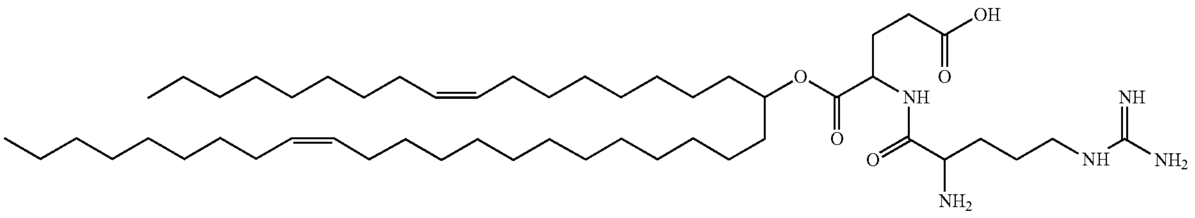

[Formula 15]

(Il)

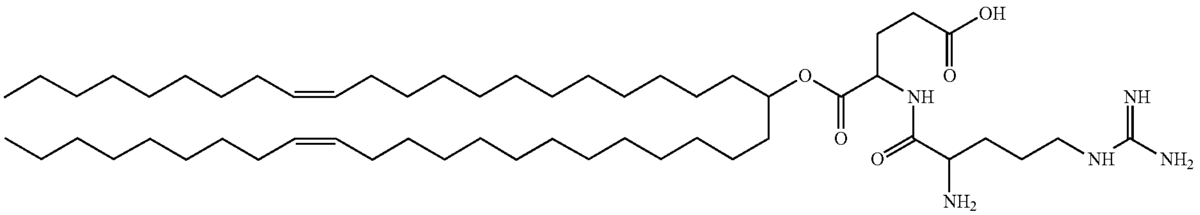

[Method for Producing Lipid]

The method for producing the compound represented by formula (I) is not particularly limited, and the compound can be produced, for example, as follows.

First, an aliphatic alcohol ($R^1$—OH) corresponding to the lipophilic region ($R^1$—O—), an amino acid ($HO_2C$—$CR^2$—$NH_2$) corresponding to a first amino acid moiety (—O—CO—$CR^2$—NH—), which is the first from the lipophilic region, or a derivative of the amino acid (the amino acid and the derivative of the amino acid are also referred to as the first amino acid), and an amino acid corresponding to a second amino acid moiety (—NH—CO—$CR^3$—$NH_2$), which is the second, or a derivative of the amino acid (the amino acid or the derivative of the amino acid are also referred to as the second amino acid) are provided.

Subsequently, the hydroxy group of the aliphatic alcohol and the carboxy group of the first amino acid are esterified, and then the amino group of the esterified product and the carboxy group of the second amino acid are amidated. By doing so, the lipid of the present embodiment can be obtained.

When carrying out the esterification reaction or the amidation reaction, the functional groups of the first amino acid and the second amino acid can also be protected in advance with a protective group so that each compound reacts with a desired functional group.

In addition, it is also possible to amidate the first amino acid and the second amino acid and then esterify the amidated product and the aliphatic alcohol.

The aliphatic alcohol ($R^1$—OH) can be obtained by subjecting a desired fatty acid or aliphatic ketone to a reduction reaction, and for example, when $R^1$ of the aliphatic alcohol ($R^1$—OH) is represented by the following formula (II) (that is, in the case of a secondary alcohol), the aliphatic alcohol ($R^1$—OH) can be obtained as follows.

[Formula 16]

(II)

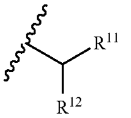

First, a fatty acid having a carboxyl group at position 1 of the hydrocarbon group of $R^1$ (fatty acid in which $R^1$ is attached to the carbonyl carbon of formic acid) and for example, an aliphatic alcohol having a hydroxy group at position 1 of the hydrocarbon group of $R^{12}$ are provided (a fatty acid having a carboxy group at position 1 of the hydrocarbon group of $R^{12}$ and for example, an aliphatic alcohol having a hydroxy group at position 1 of the hydrocarbon group of $R^1$ may be provided, but here the former case will be described).

Next, an organometallic reagent is obtained from the aliphatic alcohol having a hydroxy group at position 1 of $R^{12}$ through, for example, halogenation of the hydroxy group. Then, by reacting the fatty acid having a carboxyl group at position 1 of $R^1$ with the organometallic reagent, an aliphatic alcohol in which $R^1$ is represented by formula (II) can be obtained.

Here, a specific method for producing the lipid of the present embodiment will be described below by using the lipid of formula (Ia) above (aspartic acid as the first amino acid and arginine as the second amino acid moiety).

In the example below, to the carboxy group and the amino group of aspartic acid, protective groups (t-Bu group and Fmoc group, respectively) were attached before esterifying aspartic acid with the aliphatic alcohol, and the aliphatic alcohol (a) is esterified with aspartic acid (b).

[Formula 17]

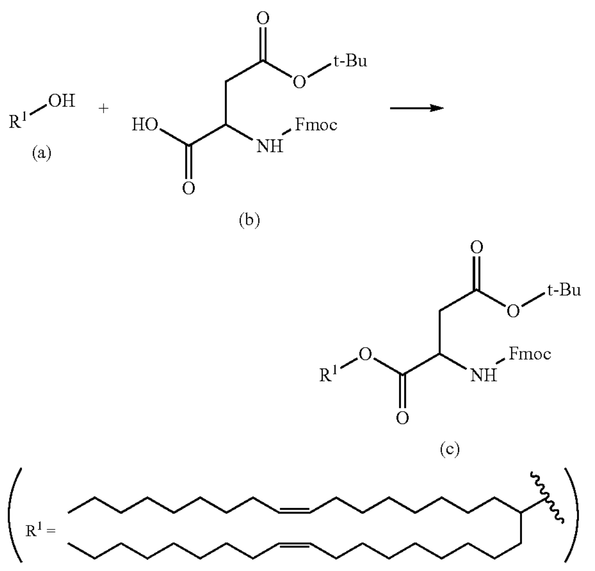

(a) (b) (c)

Subsequently, as shown below, the protective group (-Fmoc) attached to the amino group of the esterified product (c) obtained in the above process is removed, and the amino group of the esterified product (d) resulting from the removal is amidated with the carboxy group of arginine (e). In this example, to the amino group and the guanidino group of arginine, protective groups (Fmoc group and Pbf group, respectively) are attached before amidating arginine.

[Formula 18]

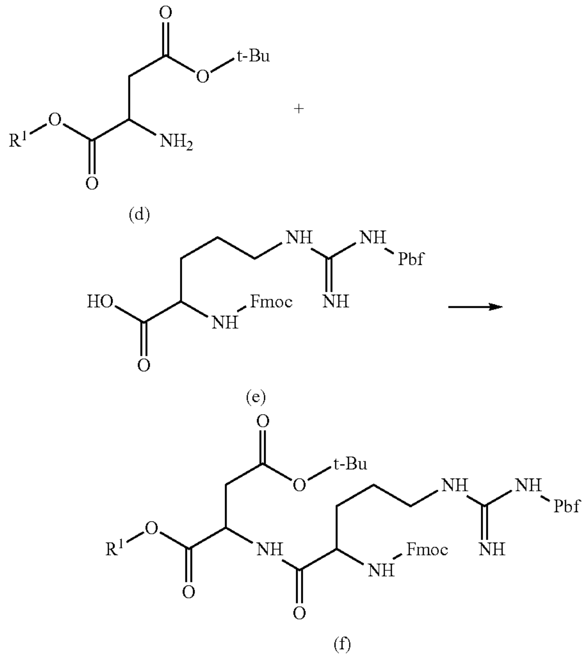

(d) (e) (f)

The amidated product (f) thus obtained has protective groups in this example, and thus the lipid of formula (Ia) can be obtained by removing the protective groups.

[Formula 19]

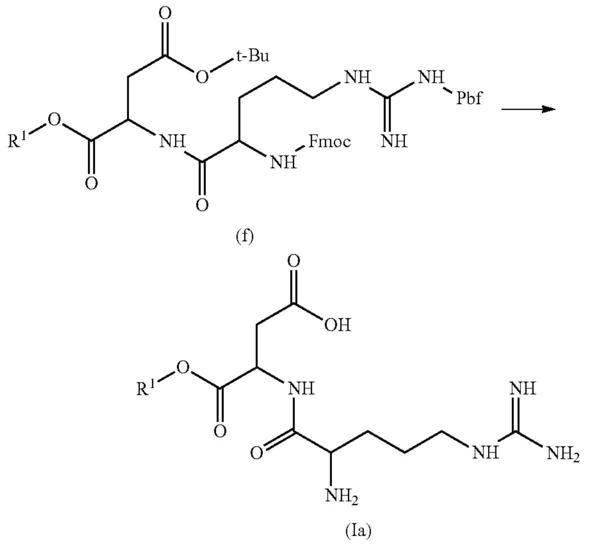

(f) (Ia)

[Introduction Compound]

Here, the lipid of the present embodiment can be used for intracellular introduction for introducing a predetermined introduction compound into a cell. Specific examples of the introduction compound include a nucleic acid, a peptide, and a protein. The introduction compound may be a biologically active substance, may be a substance that, when delivered to a cell or an organ and introduced into a cell, brings about a desired change in the cell, the organ, or another bodily tissue or system, or may be useful for treatment or prevention of an infection, a disease, a disorder, a pathological condition, or the like.

In addition, the introduction compound may be a cytotoxin, a radioactive ion, a chemotherapeutic drug, a vaccine, or a compound that induces an immune response (therapeutic drug and/or preventive drug). The vaccine includes a compound and a formulation that can provide immunity against one or more conditions associated with an infection such as influenza, measles, human papillomavirus (HPV), rabies, meningitis, pertussis, tetanus, plague, hepatitis, tuberculosis, and a coronavirus. In addition, the vaccine may include a nucleic acid, specifically an mRNA, that encodes an antigen and/or an epitope derived from such an infection. In addition, the vaccine also includes a compound and a formulation that induces an immune response against a tumor cell such as a cancer cell, and may include a nucleic acid, specifically an mRNA, that encodes an antigen, an epitope, and/or a neoepitope derived from a tumor cell. The compound that induces an immune response includes, but is not limited to, a vaccine, a corticosteroid (for example, dexamethasone), and other types.

In the present embodiment, the nucleic acid may be any molecule as long as it is a molecule obtained by polymerizing a nucleotide and/or a molecule having a function comparable to that of the nucleotide, and examples thereof include an RNA, which is a polymer of a ribonucleotide, a DNA, which is a polymer of a deoxyribonucleotide, a chimeric nucleic acid consisting of an RNA and a DNA, and a nucleotide polymer in which at least one nucleotide of these nucleic acids is replaced with a molecule having a function comparable to that of the nucleotide. In addition, the nucleic acid in the present embodiment also includes a derivative including at least one molecule obtained by polymerizing a nucleotide and/or a molecule having a function comparable to that of the nucleotide. Further, examples thereof also include a peptide nucleic acid (PNA) [Acc. Chem. Res., 32, 624 (1999)], an oxypeptide nucleic acid (OPNA) [J. Am. Chem. Soc., 123, 4653 (2001)], and a peptide ribonucleic acid (PRNA) [J. Am. Chem. Soc., 122, 6900 (2000)]. In the present embodiment, uridine U in an RNA and thymine T in a DNA can be read interchangeably.

Examples of the molecule having a function comparable to that of a nucleotide include a nucleotide derivative.

In the present embodiment, examples of the nucleic acid include a ribonucleic acid (RNA) including a messenger RNA (mRNA), and an mRNA may encode a target polypeptide including any naturally occurring or non-naturally occurring or otherwise modified polypeptide. The polypeptide encoded by an mRNA may be of any size and may have any secondary structure or activity. In some embodiments, the polypeptide encoded by an mRNA may exert a therapeutic effect when expressed intracellularly.

In addition, in the present embodiment, examples of the nucleic acid preferably include a nucleic acid that suppresses the expression of a target gene, and more preferably include a nucleic acid that has a target gene expression-suppressing action using RNA interference (RNAi).

In the present embodiment, the target gene is not particularly limited as long as it is a gene that produces and expresses an mRNA, and the target gene is preferably, for example, a gene related to a tumor or an inflammation, and examples thereof include a gene encoding a protein such as a vascular endothelial growth factor (hereinafter abbreviated as VEGF), a vascular endothelial growth factor receptor (hereinafter abbreviated as VEGFR), a fibroblast growth factor, a fibroblast growth factor receptor, a platelet-derived growth factor, a platelet-derived growth factor receptor, a hepatocyte growth factor, a hepatocyte growth factor receptor, a Kruppel-like factor (hereinafter abbreviated as KLF), an Ets transcription factor, a nuclear factor, a hypoxia-inducible factor, a cell cycle-related factor, a chromosome replication-related factor, a chromosome repair-related factor, a microtubule-related factor, a growth signal pathway-related factor, a growth-related transcription factor, or an apoptosis-related factor, and specifically include a VEGF gene, a VEGFR gene, a fibroblast growth factor gene, a fibroblast growth factor receptor gene, a platelet-derived growth factor gene, a platelet-derived growth factor receptor gene, a hepatocyte growth factor gene, a hepatocyte growth factor receptor gene, a KLF gene, an Ets transcription factor gene, a nuclear factor gene, a hypoxia-inducible factor gene, a cell cycle-related factor gene, a chromosome replication-related factor gene, a chromosome repair-related factor gene, a microtubule-related factor gene (for example, CKAP5 gene), a growth signal pathway-related factor gene (for example, KRAS gene), a growth-related transcription factor gene, and an apoptosis-related factor (for example, BCL-2 gene).

In addition, in the present embodiment, the target gene is preferably, for example, a gene expressed in the liver, the lung, the kidney, or the spleen, and examples thereof include the above gene related to a tumor or an inflammation, a hepatitis B virus genome, a hepatitis C virus genome, and a gene encoding a protein such as an apolipoprotein (APO), hydroxymethylglutaryl (HMG) CoA reductase, kexin type 9 serine protease (PCSK9), factor 12, a glucagon receptor, a glucocorticoid receptor, a leukotriene receptor, a thromboxane A2 receptor, a histamine H1 receptor, a carbonic anhydrase, an angiotensin converting enzyme, renin, p53, a tyrosine phosphatase (PTP), a sodium-dependent glucose transporter, a tumor necrosis factor, or an interleukin.

For the nucleic acid that suppresses the expression of a target gene, for example, as a nucleic acid that includes a base sequence complementary to a partial base sequence of an mRNA of a gene encoding a protein or the like (target gene) and that suppresses the expression of a target gene, any nucleic acid of a double-stranded nucleic acid such as an siRNA (small interfering RNA) or an miRNA (micro RNA), a single-stranded nucleic acid such as an shRNA (short hairpin RNA), an antisense nucleic acid, or a ribozyme, and the like may be used, and a double-stranded nucleic acid is suitably used.

The nucleic acid that includes a base sequence complementary to a partial base sequence of an mRNA of a target gene is referred to as an antisense strand nucleic acid, and the nucleic acid that includes a base sequence complementary to the base sequence of the antisense strand nucleic acid is also referred to as a sense strand nucleic acid. The sense strand nucleic acid refers to a nucleic acid that can form a double strand formation portion by pairing with an antisense strand nucleic acid, such as a nucleic acid itself consisting of a partial base sequence of a target gene.

The double-stranded nucleic acid refers to a nucleic acid having a double strand formation portion consisting of paired two strands. The double strand formation portion refers to a portion in which a double strand is formed by base pairing of nucleotides or derivatives thereof constituting a double-stranded nucleic acid. The base pairs constituting the double strand formation portion are usually 15 to 27 base pairs, preferably 15 to 25 base pairs, more preferably 15 to 23 base pairs, further preferably 15 to 21 base pairs, and particularly preferably 15 to 19 base pairs.

As the antisense strand nucleic acid of the double strand formation portion, a nucleic acid that includes a base sequence complementary to a partial sequence of an mRNA of a target gene, or a nucleic acid that is derived from the above nucleic acid by substitution, deletion, or addition of 1 to 3 bases, preferably 1 to 2 bases, or more preferably 1 base and that has target protein expression-suppressing activity is suitably used. The length of a single-stranded nucleic acid constituting the double-stranded nucleic acid is usually 15 to 30 bases, preferably 15 to 29 bases, more preferably 15 to 27 bases, further preferably 15 to 25 bases, particularly preferably 17 to 23 bases, and most preferably 19 to 21 bases.

Either one or both nucleic acids of an antisense strand and a sense strand that constitute the double-stranded nucleic acid may have an additional nucleic acid that does not form a double strand on the 3' side or the 5' side contiguous with the double strand formation portion. This portion that does not form a double strand is also referred to as an overhang.

As a double-stranded nucleic acid having an overhang, one having an overhang consisting of 1 to 4 bases, usually 1 to 3 bases, at the 3' end or the 5' end of at least one strand is used, one having an overhang consisting of 2 bases is preferably used, and one having an overhang consisting of dTdT or UU is more preferably used. An overhang may be present only on the antisense strand, only on the sense strand, or on both the antisense strand and the sense strand, and a double-stranded nucleic acid having an overhang on both the antisense strand and the sense strand is preferably used.

In addition, a sequence, contiguous with the double strand formation portion, that partially or completely matches an mRNA of a target gene, or a sequence, contiguous with the double strand formation portion, that matches the base sequence of the complementary strand of an mRNA of a target gene may be used. Further, as a nucleic acid that suppresses the expression of a target gene, for example, a nucleic acid molecule that generates the above double-stranded nucleic acid by the action of a ribonuclease such as Dicer (International Publication No. WO 2005/089287) or a double-stranded nucleic acid that does not have an overhang at the 3' end or the 5' end can also be used.

In addition, when the double-stranded nucleic acid is an siRNA, the antisense strand has a sequence of at least bases 1 to 17 from the 5' end side toward the 3' end side that is a base sequence complementary to a sequence of 17 consecutive bases of the mRNA of the target gene, and the antisense strand has preferably a sequence of at least bases 1 to 19 from the 5' end side toward the 3' end side that is a base sequence complementary to a sequence of 19 consecutive bases of the mRNA of the target gene, or a sequence of at least bases 1 to 21 that is a base sequence complementary to a sequence of 21 consecutive bases of the mRNA of the target gene, or a sequence of at least bases 1 to 25 that is a base sequence complementary to a sequence of 25 consecutive bases of the mRNA of the target gene.

Further, in the present embodiment, when the nucleic acid is an siRNA, preferably 10 to 70%, more preferably 15 to 60%, and further preferably 20 to 50% of the sugar in the nucleic acid is ribose substituted with a modifying group at position 2'. In the present embodiment, "substituted with a modifying group at position 2' of ribose" means that the hydroxyl group at position 2' is substituted with a modifying group, and the resulting configuration may be the same as or different from that of the hydroxyl group at position 2' of ribose, and is preferably the same as that of the hydroxyl group at position 2' of ribose. Ribose substituted with a modifying group at position 2' is included in a 2'-modified nucleotide in a sugar moiety-modified nucleotide, and the modifying group of ribose substituted with a modifying group at position 2' is synonymous with a modifying group of the 2'-modified nucleotide.

In the present embodiment, the nucleic acid includes a derivative in which an oxygen atom or the like included in a phosphoric acid moiety, an ester moiety, or the like in the structure of the nucleic acid is replaced with another atom such as a sulfur atom.

In addition, in a sugar bound to the base at the 5' end of each of the antisense strand and the sense strand, the hydroxyl group at position 5' may be modified with a phosphic acid group or the above modifying group, or a group that is converted to a phosphic acid group or the above modifying group by an in vivo nuclease or the like.

In addition, in a sugar bound to the base at the 3' end of each of the antisense strand and the sense strand, the hydroxyl group at position 3' may be modified with a phosphic acid group or the above modifying group, or a group that is converted to a phosphic acid group or the above modifying group by an in vivo nuclease or the like.

The single-stranded nucleic acid may be any of a nucleic acid that consists of a sequence complementary to a sequence consisting of 15 to 27 consecutive bases of the target gene, preferably 15 to 25 bases, more preferably 15 to 23 bases, further preferably 15 to 21 bases, and particularly preferably 15 to 19 bases, or a nucleic acid that is derived from the above nucleic acid by substitution, deletion, or addition of 1 to 3 bases, preferably 1 to 2 bases, or more preferably 1 base and that has target protein expression-suppressing activity. A single-stranded nucleic acid having 15 to 30 bases, preferably 15 to 29 bases, more preferably 15 to 27 bases, further preferably 15 to 25 bases, particularly preferably 15 to 23 bases as the length of the single-stranded nucleic acid is suitably used.

As the single-stranded nucleic acid, one obtained by linking the antisense strand and the sense strand that constitute the above double-stranded nucleic acid via a spacer sequence (spacer oligonucleotide) may be used. The spacer oligonucleotide is preferably a single-stranded nucleic acid molecule having 6 to 12 bases, and the sequence thereof on the 5' end side is preferably UU. Examples of the spacer oligonucleotide include a nucleic acid consisting of the sequence UUCAAGAGA. For the order of the antisense strand and the sense strand linked via the spacer oligonucleotide, either thereof may be on the 5' side. The single-stranded nucleic acid is preferably a single-stranded nucleic acid such as an shRNA having a double strand formation portion due to a stem-loop structure. The single-stranded nucleic acid such as an shRNA is usually 50 to 70 bases long.

A nucleic acid 70 bases or less long, preferably 50 bases or less long, further preferably 30 bases or less long, designed to generate the above single-stranded nucleic acid or double-stranded nucleic acid by the action of a ribonuclease or the like may be used.

The nucleic acid used in the present embodiment may be produced by using a known RNA or DNA synthesis method and an RNA or DNA modification method.

[Composition]

Subsequently, the composition according to the present embodiment will be described.

The composition of the present embodiment contains the above lipid represented by formula (I) above and the above introduction compound, and more specifically, may include a lipid nanoparticle that is formed by assembly of a plurality of lipids represented by formula (I) and encapsulates the introduction compound therein.

The composition of the present embodiment may contain a combination of two or more lipids represented by formula (I), or may further contain a molecule other than the above lipid represented by formula (I), such as an amphiphilic molecule (for example, a biomembrane-derived phospholipid such as phosphatidylinositol, phosphatidylserine, phosphatidylethanolamine, or phosphatidylcholine), a cationic lipid molecule, a surfactant (for example, CHAPS, sodium cholate, octylglucoside, or an N-D-gluco-N-methylalkanamide), a polyethylene glycol-modified lipid, a glycolipid, a peptide lipid, a protein, or a sterol, as long as advantages of the present invention such as efficiency of intracellular introduction of the introduction compound and low cytotoxicity are not impaired.

Examples of the polyethylene glycol-modified lipid include PEG2000-DMG (PEG2000-dimyristylglycerol), PEG2000-DPG (PEG2000-dipalmitoylglycerol), PEG2000-DSG (PEG2000-distearoylglycerol), PEG5000-DMG (PEG5000-dimyristylglycerol), PEG5000-DPG (PEG5000-dipalmitoylglycerol), PEG5000-DSG (PEG5000-distearoylglycerol), PEG-cDMA (N-[(methoxypoly(ethylene glycol)2000)carbamyl]-1,2-dimyristyloxylpropyl-3-amine), PEG-C-DOMG (R-3-[(w-methoxy-poly(ethylene glycol) 2000)carbamoyl]-1,2-dimyristyloxylpropyl-3-amine), polyethylene glycol (PEG)-diacylglycerol (DAG), PEG-dialkyloxypropyl (DAA), PEG-phospholipid, and PEG-ceramide (Cer). Such polyethylene glycol-modified lipids may be used singly or as a mixture of two or more thereof.

Examples of the sterol include cholesterol, dihydrocholesterol, lanosterol, β-sitosterol, campesterol, stigmasterol, brassicasterol, ergosterol, fucosterol, and 3β-[N—(N',N'- dimethylaminoethyl)carbamoyl]cholesterol (DC-Chol). Such sterols may be used singly or as a mixture of two or more thereof.

In the present embodiment, a lipid nanoparticle may be formed by assembling and organizing the above lipid represented by formula (I). Here, "organizing" means that constituent molecules including the above lipid represented by formula (I) and a molecule other than the lipid represented by formula (I), which may optionally be contained, assemble via a non-covalent bond such as a hydrophobic bond. Examples of an organized assembly include a bilayer, a liposome, a multi-vesicle, a string-like aggregate, a disk-like aggregate, a lamellar aggregate, a rod-like aggregate, or the like formed by hydrophobic bonding of hydrophobic moieties of constituent molecules, and a mixture thereof. A lipid nanoparticle can be obtained by encapsulating the introduction compound therein in the organization process.

In addition to the components described above, the composition of the present embodiment may contain, as a further additive, a sugar such as sucrose, glucose, sorbitol, or lactose; an amino acid such as glutamine, glutamic acid, sodium glutamate, or histidine; or a salt of an acid such as citric acid, phosphoric acid, acetic acid, lactic acid, carbonic acid, or tartaric acid.

The composition of the present embodiment may be formulated as a pharmaceutical composition. Examples of a dosage form of the pharmaceutical composition include an injection, among others.

The composition of the present embodiment may be, for example, in a state of a powder from which the solvent has been removed by freeze-drying or the like, or in a state of a liquid. When the composition is in a state of a powder, the composition can be used as an injection by suspending or dissolving the composition in a pharmaceutically acceptable vehicle before use. When the composition is in a state of a liquid, the composition can be used as an injection as it is or by suspending or dissolving the composition in a pharmaceutically acceptable vehicle.

Examples of the pharmaceutically acceptable vehicle include sterile water; physiological saline; and an isotonic solution including an adjuvant such as glucose, D-sorbitol, D-mannose, D-mannitol, or sodium chloride. The composition of the present embodiment may further contain an additive such as a dissolution enhancer such as an alcohol such as ethanol, propylene glycol, or polyethylene glycol, a stabilizer, an antioxidant, or an antiseptic.

For the particle size of the lipid nanoparticle in the composition of the present embodiment, the average particle size can be calculated, and the particle size (average particle size) of the lipid nanoparticle is preferably 250 nm or less, more preferably 200 nm or less, further preferably 150 nm or less, further more preferably 130 nm or less, and most preferably 120 nm or less. In addition, the particle size (average particle size) of the lipid nanoparticle is preferably 10 nm or more, and more preferably 30 nm or more.

In addition, the polydispersity index (PDI) of the lipid nanoparticle is preferably 0.4 or less, more preferably 0.3 or less, and further preferably 0.2 or less.

When the particle size and/or the polydispersity index are in the above range, it can be made easier to reach a subject such as a target cell or tissue in vivo.

The average particle size and the polydispersity index can be measured by the methods described in the Examples section.

The composition of the embodiment preferably has a low electric charge as measured, for example, in Tris-HCl at pH 7.4, from the viewpoint of suppressing nonspecific adsorption and immune reaction.

The electric charge of the composition measured in Tris-HCl at pH 7.4 can be measured by the method described in the Examples section.

The lipid nanoparticle of the composition of the present embodiment can be formed by a known method without particular limitation.

The method for producing the composition includes, for example, a step of preparing an aqueous solution such as a citrate buffer solution including the introduction compound and a polar organic solvent-containing solution containing at least the lipid of the present embodiment, a step of mixing the solution with the polar organic solvent-containing solution to obtain a mixed solution, and a step of removing the polar organic solvent in the mixed solution. According to this method for producing the composition, a composition including a lipid nanoparticle in which the introduction compound is efficiently encapsulated can be obtained.

The polar organic solvent-containing solution may further contain a molecule other than the lipid of the present embodiment, such as an amphiphilic molecule (for example, a biomembrane-derived phospholipid such as phosphatidylinositol, phosphatidylserine, phosphatidylethanolamine, or phosphatidylcholine), a cationic lipid molecule, a surfactant (for example, CHAPS, sodium cholate, octylglucoside, or an N-D-gluco-N-methylalkanamide), a polyethylene glycol-modified lipid, a glycolipid, a peptide lipid, a protein, or a sterol such as cholesterol.

In addition, the polar organic solvent of the polar organic solvent-containing solution is not particularly limited, and examples thereof include an alcohol such as ethanol or t-butanol from the viewpoint of the polarity of the solvent and the ease of removing the solvent after the formation of a lipid nanoparticle.

The step of obtaining a mixed solution can be carried out by using, for example, a vortex mixer or a microchannel. In addition, the step of obtaining a mixed solution can form a lipid nanoparticle in which the introduction compound is encapsulated, in the mixed solution.

The step of removing the polar organic solvent can reduce the content of the polar organic solvent, for example, by diafiltration, ultrafiltration, or evaporation under reduced pressure.

An incubation step may also be carried out between the step of obtaining a mixed solution and the step of reducing the content of the polar organic solvent.

In the present embodiment, for example, the composition of the present embodiment may be intravenously administered to a mammal including a human and thereby delivered to, for example, an organ or a site where a cancer or an inflammation has occurred, to introduce the introduction compound such as a nucleic acid in the composition of the present embodiment into a cell of the delivery organ or site. The organ or the site where a cancer or an inflammation has occurred is not particularly limited, and examples thereof include the stomach, the large intestine, the liver, a lung, the spleen, the pancreas, a kidney, the bladder, the skin, a blood vessel, and an eyeball. In addition, the composition of the present embodiment may be intravenously administered to a mammal including a human and thereby delivered to, for example, a blood vessel, the liver, a lung, the spleen, and/or a kidney, to introduce the introduction compound in the composition of the present embodiment into a cell of the delivery organ or site. The cell of the liver, a lung, the spleen, and/or a kidney may be any of a normal cell, a cell associated with a cancer or an inflammation, or a cell associated with another disease.

If the introduction compound in the composition of the present embodiment is a nucleic acid and the nucleic acid is a nucleic acid that has a target gene expression-suppressing action using RNA interference (RNAi), a nucleic acid or the like that suppresses the expression of a gene can be introduced into a mammalian cell, and the expression of the gene or the like can be suppressed. The administration subject is preferably a human.

In addition, if the target gene in the composition of the present embodiment is, for example, a gene associated with a tumor or an inflammation, the composition of the present embodiment may be used as a therapeutic agent and/or a preventive agent for a cancer or an inflammatory disease, preferably a therapeutic agent or a preventive agent for a solid cancer or an inflammation of a blood vessel or in the vicinity of a blood vessel. Specifically, if the target gene in the composition of the present embodiment is a gene associated with angiogenesis or the like, vascular smooth muscle proliferation, angiogenesis, or the like can be suppressed, and thus the composition of the present embodiment may be used, for example, as a therapeutic or preventive agent for a cancer or an inflammatory disease that involves vascular smooth muscle proliferation or angiogenesis.

That is, the present embodiment also provides a method for treating a cancer or an inflammatory disease, including administering the composition of the present embodiment described above to a mammal. The administration subject is preferably a human, and more preferably a human suffering from a cancer or an inflammatory disease.

The composition of the present embodiment may also be used as a formulation that aims to stabilize the nucleic acid, for example, in a biological component such as a blood component (for example, blood or gastrointestinal tract), reduce a side effect, increase agent accumulation in a tissue or an organ that includes a target gene expression site, or the like.

Further, if the introduction compound in the composition of the present embodiment is a nucleic acid and the nucleic acid is an mRNA encoding an antigen derived from infectious diseases or tumor cells, or the like, the mRNA can be directed to induce a specific immune response and thus can be applied to development of a wide range of therapeutic and preventive mRNA vaccines for a wide variety of diseases, including an infection and a tumor.

For the administration route of the composition of the present embodiment, it is desirable to use the most effective administration route for treatment, and examples thereof include a parenteral administration such as intraoral administration, airway administration, intrarectal administration, subcutaneous administration, intradermal administration, intramuscular administration, or intravenous administration, or oral administration, and preferably include intravenous administration or intramuscular administration. In addition, intramuscular administration is preferable when the composition of the present embodiment is used as an mRNA vaccine.

The dosage of the composition also varies depending on the administration subject, the target organ, the symptom, or the administration method.

The embodiment of the present invention has been described above, but the lipid and the composition of the present invention are not limited to the above examples, and a modification may appropriately be made to the lipid and the composition of the present invention.

EXAMPLES

Hereinafter, the present invention will be described in more detail with reference to Examples, but the following Examples are intended to illustrate the present invention and should not be construed as limiting. The structures of a final product, an intermediate, and a starting material are confirmed, for example, by a standard analytical method, such as MS or NMR. The abbreviations used in the Examples below are conventional abbreviations well known to those skilled in the art. Some abbreviations are listed below.

DCC: dicyclohexylcarbodiimide
DMAP: N,N-dimethyl-4-aminopyridine
TEA: triethylamine
THF: tetrahydrofuran
TFA: trifluoroacetic acid
MsCl: methanesulfonyl chloride $^1$H NMR spectra were recorded with a nuclear magnetic resonance apparatus, JNM-ECZ400S, 400 MHz spectrometer, manufactured by JEOL Ltd. All chemical shifts are reported in parts per million (8) relative to chloroform. The following abbreviations are used to denote signal patterns: s=singlet, d=doublet, t=triplet, q=quartet, quin=quintet, M=multiplet, br=broad.

MS data were measured in ESI+ ion mode by using a high-performance liquid chromatography tandem mass spectrometer (apparatus name: UPLC-MS/MS System ACQUITY TQD; manufactured by Nihon Waters K.K.). The measurement conditions were a capillary voltage of 4.0 kV, a cone voltage of 30 V, a source temperature of 100° C., and a desolvation gas temperature of 250° C.

<Synthesis of Lipids>

The lipids of the Examples and the Comparative Examples shown below were synthesized.

Example 1

Synthesis of 3-(2-amino-5-guanidinopentanamido)-4-(((9Z,27Z)-hexatriaconta-9,27-dien-18-yl)oxy)-4-oxobutanoic acid (hereinafter also referred to as lipid (Ia)) Lipid (Ia) is a dipeptide in which the lipophilic region is a hydrocarbon group having 36 carbon atoms and the hydrophilic region is derived from Asp (first amino acid) and Arg (second amino acid). Hereinafter, a method for synthesizing lipid (Ia) will be described.

Step (a1): Synthesis of N-methoxy-N-methylolamide

[Formula 20]

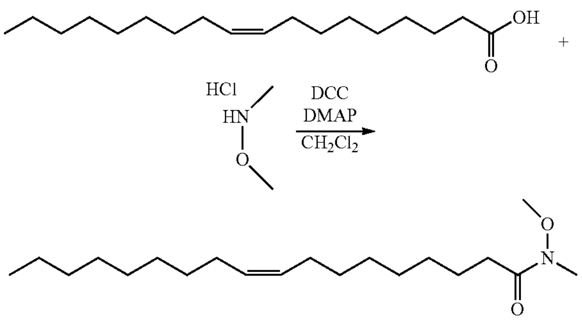

Oleic acid (42.4 g, 150 mmol), DMAP (2.75 g, 22.5 mmol), N,O-dimethylhydroxylamine hydrochloride (21.9 g, 225 mmol) were dissolved in dichloromethane (150 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to quantitatively obtain the target N-methoxy-N-methylolamide.

Step (a2): Synthesis of (Z)-octadec-9-en-1-yl methanesulfonate

[Formula 21]

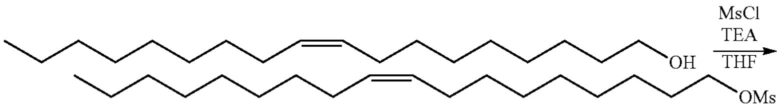

Oleyl alcohol (100.0 g, 372.45 mmol) and TEA (113.07 g, 1.117 mmol) was dissolved in THF (900 mL), the resulting solution was cooled to 0° C., and MsCl (63.9 g, 558.7 mmol) was added thereto. After the addition, the resulting mixture was heated to room temperature and allowed to react at room temperature for 2 hours. After completion of the reaction, dichloromethane and triethylamine were concentrated under reduced pressure, the resulting residue was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to quantitatively obtain the target (Z)-octadec-9-en-1-yl methanesulfonate.

Step (a3): Synthesis of (Z)-1-bromooctadec-9-ene

[Formula 22]

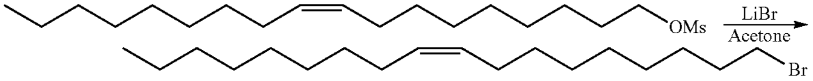

(Z)-octadec-9-en-1-yl methanesulfonate (135 g, 390 mmol) obtained in step (a2) above and lithium bromide (161 g, 1850 mmol) were dissolved in acetone (300 mL) and allowed to react under reflux for 1 hour. After completion of the reaction, the solvent was concentrated under reduced pressure, the resulting residue was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (heptane) to quantitatively obtain the target (Z)-1-bromooctadec-9-ene.

Step (a4): Synthesis of (9Z,27Z)-hexatriaconta-9,27-dien-18-one

[Formula 23]

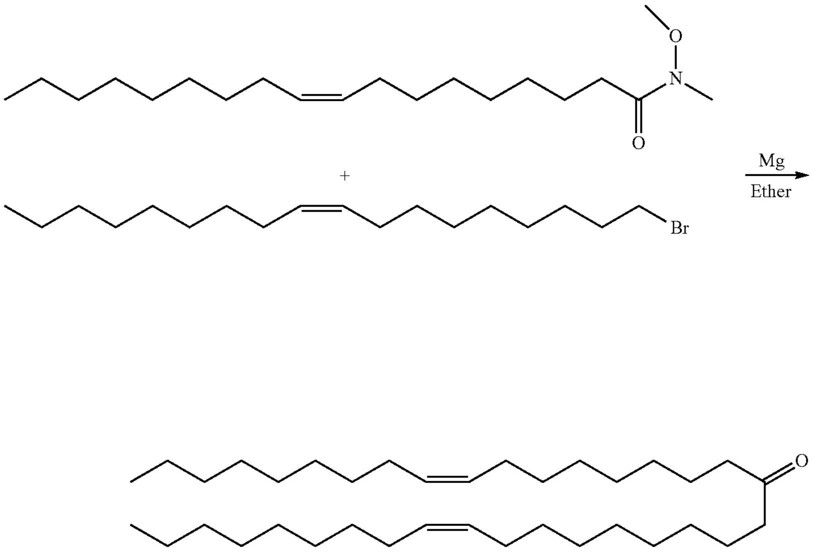

A solution of (Z)-1-bromooctadec-9-ene (40.7 g, 123 mmol) obtained in step (a3) in diethyl ether (250 mL) was added dropwise with stirring to magnesium (3.73 g, 154 mmol) and diethyl ether (25 mL). After completion of the dropwise addition, the resulting mixture was stirred for 1 hour, and subsequently a solution of N-methoxy-N-methylolamide (20 g, 61.4 mmol) obtained in step (a1) in diethyl ether (125 mL) was added dropwise. The reaction was considered complete when the disappearance of the raw materials was confirmed by thin layer chromatography (TLC). After completion of the reaction, the reaction system was quenched by adding water and extracted with ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to quantitatively obtain the target (9Z,27Z)-hexatriaconta-9,27-dien-18-one.

Step (a5): Synthesis of (9Z,27Z)-hexatriaconta-9,27-dien-18-01

[Formula 24]

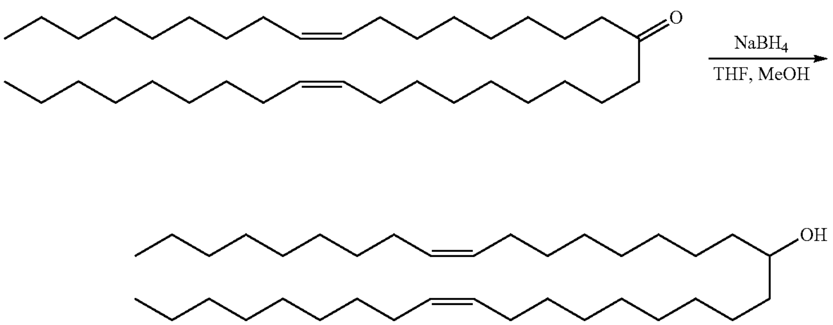

Sodium borohydride (11.7 g, 309 mmol) was added to a solution of (9Z,27Z)-hexatriaconta-9,27-dien-18-one (31.9 g, 61.7 mmol) obtained in step (a4) in THF (120 mL) and methanol (120 mL) and allowed to react. After completion of the reaction, the solvent was concentrated under reduced pressure, the resulting residue was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to quantitatively obtain the target (9Z,27Z)-hexatriaconta-9, 27-dien-18-01.

Step (a6): Synthesis of 4-(tert-butyl) 1-((9Z,27Z)-hexatriaconta-9,27-dien-18-yl) (((9H-fluoren-9-yl) methoxy)carbonyl)aspartate

[Formula 25]

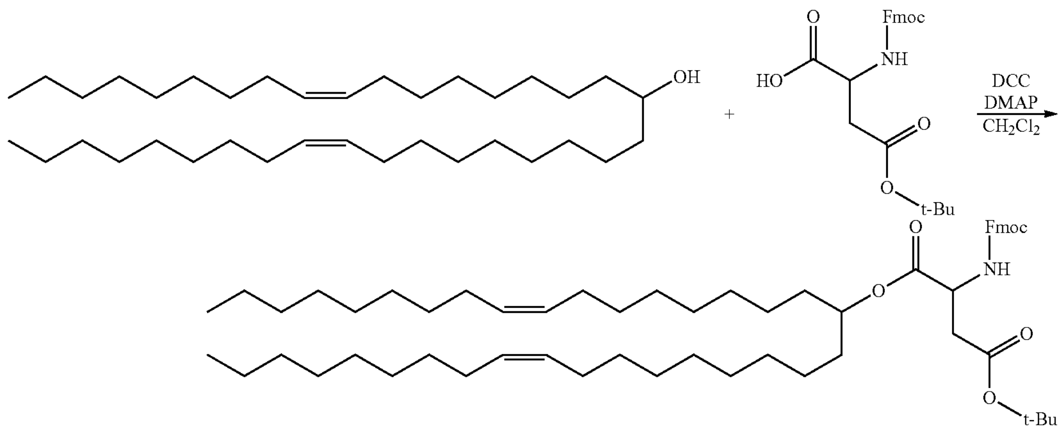

(9Z,27Z)-Hexatriaconta-9,27-dien-18-ol (4.0 g, 7.7 mmol) obtained in step (a5), Fmoc-Asp(tBu)-OH (3.8 g, 9.2 mmol) in which to the amino group and the carboxy group of aspartic acid, protective groups (Fmoc group and tBu group, respectively) had been attached in advance, DCC (2.3 g, 11.5 mmol), and DMAP (0.28 g, 2.3 mmol) were dissolved in dichloromethane (15 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) (((9H-fluoren-9-yl)methoxy)carbonyl)aspartate (3.5 g, 3.8 mmol, 50%).

Step (a7): Synthesis of 4-(tert-butyl) 1-((9Z,27Z)-hexatriaconta-9,27-dien-18-yl) aspartate

[Formula 26]

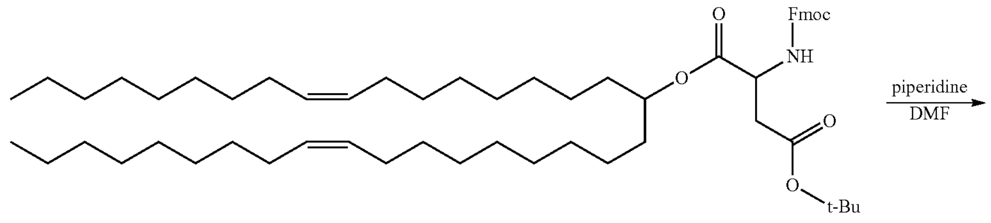

-continued

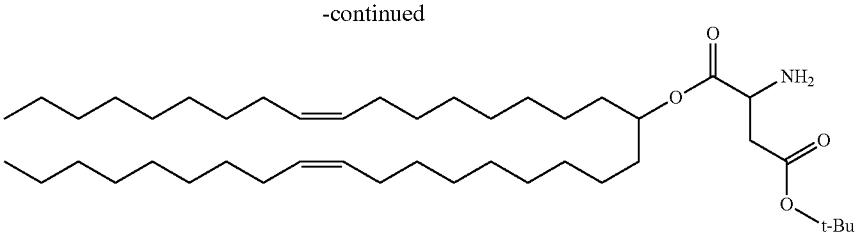

4-(tert-Butyl) 1-((9Z,27Z)-hexatriaconta-9,27-dien-18-yl) (((9H-fluoren-9-yl)methoxy)carbonyl)aspartate (3.0 g, 3.3 mmol) obtained in step (a6) was dissolved in a 20% piperidine/DMF solution (40 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) aspartate (1.2 g, 1.7 mmol, 53%).

Step (a8): Synthesis of 4-(tert-butyl) 1-((9Z,27Z)-hexatriaconta-9,27-dien-18-yl) N2-(((9H-fluoren-9-yl)methoxy)carbonyl)-Nw-((2,2,4,6,7-pentamethyl-2,3-dihydrobenzofuran-5-yl)sulfonyl) arginylaspartate

[Formula 27]

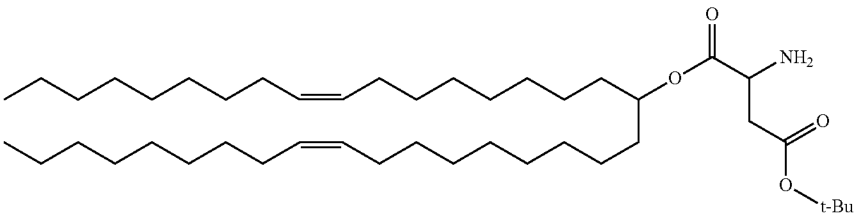

+

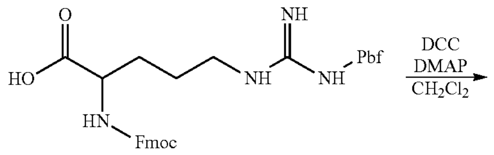

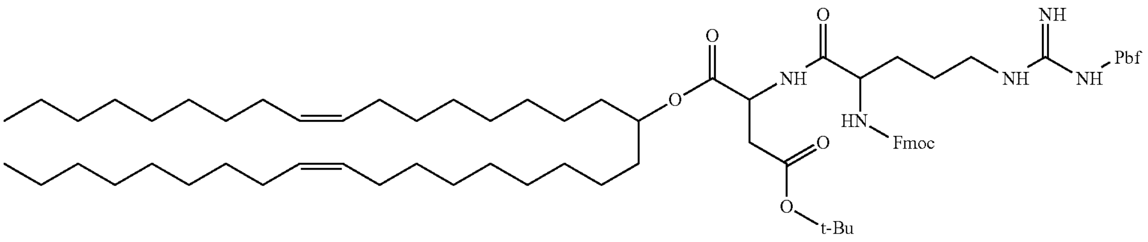

4-(tert-butyl) 1-((9Z,27Z)-hexatriaconta-9,27-dien-18-yl) aspartate (1.0 g, 1.4 mmol) obtained in step (a7), Fmoc-Arg (Pbf)-OH (1.88 g, 2.9 mmol) (manufactured by TCI), and DCC (0.42 g, 2.9 mmol) were dissolved in dichloromethane (9 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) N2-(((9H-fluoren-9-yl)methoxy)carbonyl)-Nw-((2,2,4,6,7-pentamethyl-2,3-dihydrobenzofuran-5-yl)sulfonyl) arginylaspartate (1.8 g, 1.4 mmol, 94%).

Step (a9): Synthesis of 4-(tert-butyl) 1-((9Z,27Z)-hexatriaconta-9,27-dien-18-yl) Nw-((2,2,4,6,7-pentamethyl-2,3-dihydrobenzofuran-5-yl)sulfonyl)arginylaspartate

[Formula 28]

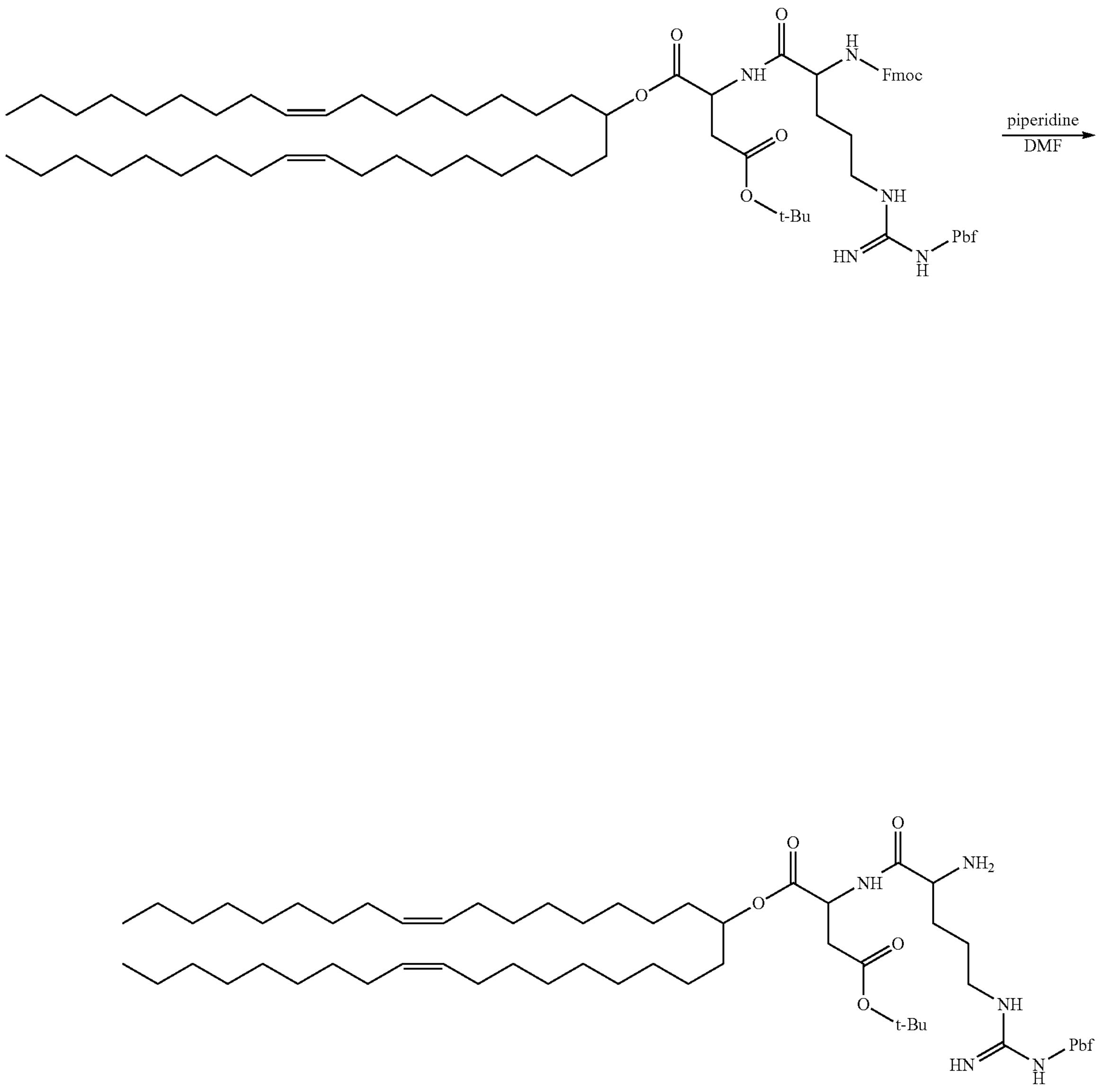

4-(tert-Butyl) 1-((9Z,27Z)-hexatriaconta-9,27-dien-18-yl) N2-(((9H-fluoren-9-yl)methoxy)carbonyl)-Nw-((2,2,4,6,7-pentamethyl-2,3-dihydrobenzofuran-5-yl)sulfonyl)arginylaspartate (1.8 g, 1.4 mmol) obtained in step (a8) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) Nw-((2,2,4,6,7-pentamethyl-2,3-dihydrobenzofuran-5-yl) sulfonyl)arginylaspartate (0.9 g, 1.1 mmol, 73%).

Step (a10): Synthesis of 3-(2-amino-5-guanidinopentanamido)-4-(((9Z,27Z)-hexatriaconta-9,27-dien-18-yl)oxy)-4-oxobutanoic acid (lipid (Ia))

[Formula 29]

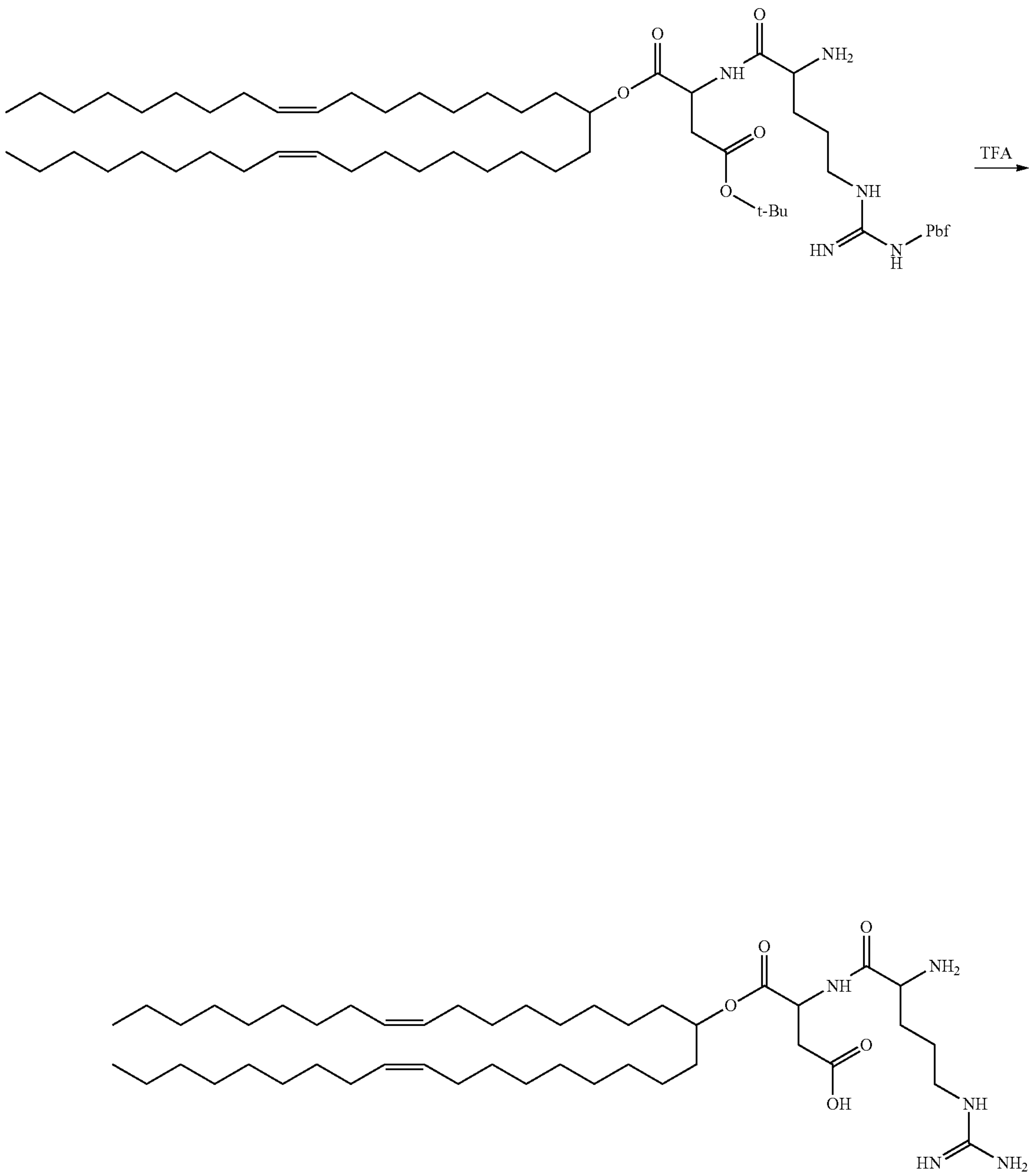

4-(tert-Butyl) 1-((9Z,27Z)-hexatriaconta-9,27-dien-18-yl) Nw-((2,2,4,6,7-pentamethyl-2,3-dihydrobenzofuran-5-yl)sulfonyl)arginylaspartate (0.9 g, 1.1 mmol) obtained in step (a9) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target 3-(2-amino-5-guanidinopentanamido)-4-(((9Z,27Z)-hexatriaconta-9,27-dien-18-yl)oxy)-4-oxobutanoic acid (lipid (Ia)) (0.3 g, 0.37 mmol, 36%).

$^1$H-NMR (400 MHz, CHLOROFORM-D) δ 5.47-5.13 (4H), 4.93-4.61 (2H), 4.13-3.73 (1H), 3.36-2.90 (2H), 2.89-2.42 (2H), 2.11-1.76 (10H), 1.57-1.42 (6H), 1.42-0.98 (46H), 0.98-0.25 (6H)

$[C_{46}H_{87}N_5O_5H]^+$: 790.73

Example 2

Synthesis of 4-(2-amino-5-guanidinopentanamido)-5-(((9Z,27Z)-hexatriaconta-9,27-dien-18-yl)oxy)-5-oxopentanoic acid (hereinafter also referred to as lipid (Ib))

Lipid (Ib) is a lipid in which the first amino acid of lipid (Ia) is changed to Glu. Hereinafter, a method for synthesizing lipid (Ib) will be described. The step of synthesizing a lipophilic region in the synthesis step is the same as the steps of step (a1) to step (a5) for lipid (Ia), and thus will be omitted.

Step (b6): Synthesis of 5-(tert-butyl) 1-((9Z,27Z)-hexatriaconta-9,27-dien-18-yl) (((9H-fluoren-9-yl)methoxy)carbonyl)glutamate

[Formula 30]

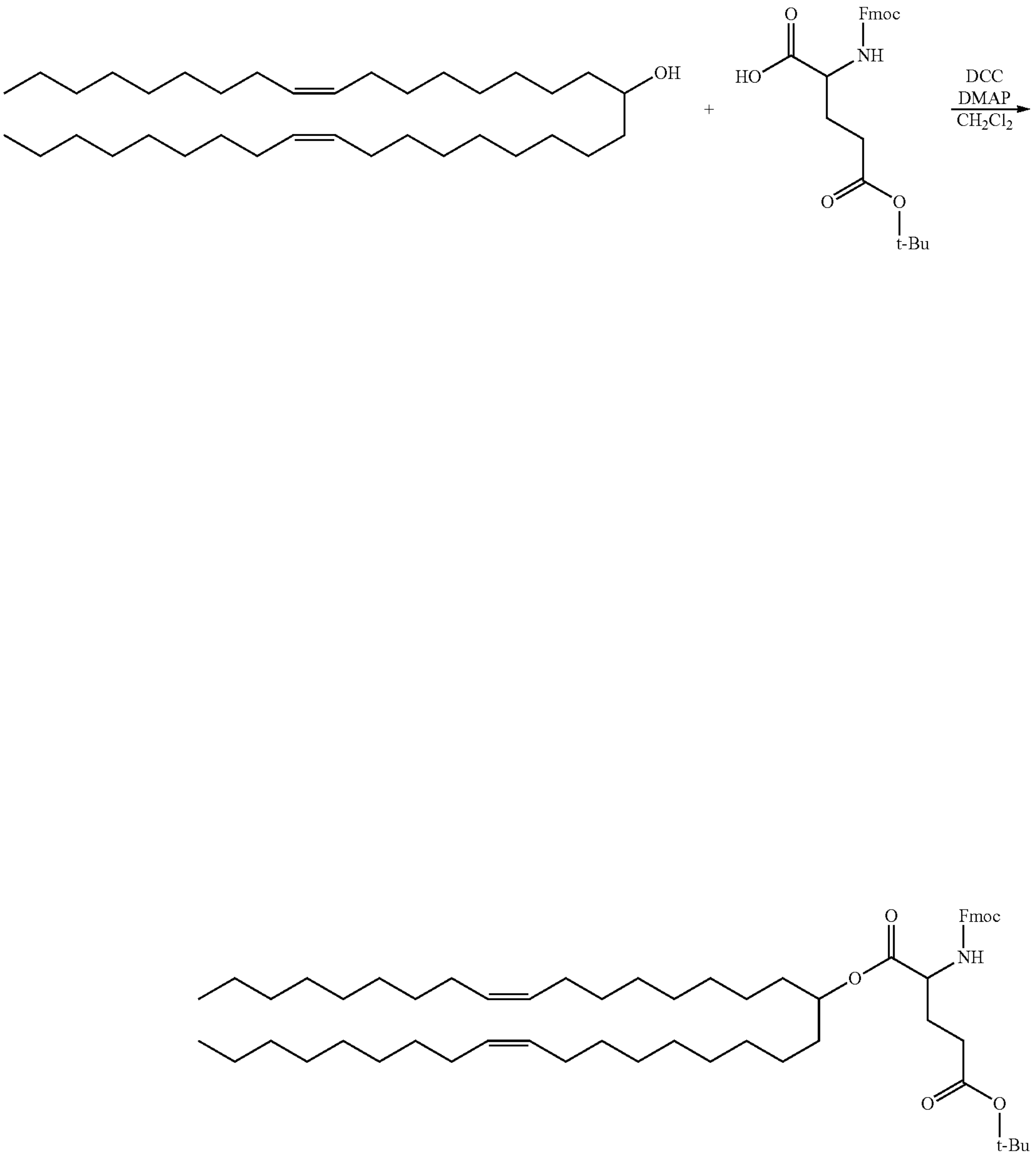

(9Z,27Z)-Hexatriaconta-9,27-dien-18-01 (3.0 g, 5.7 mmol) obtained in step (a5), Fmoc-Glu(tBu)-OH (4.92 g, 11.5 mmol) in which to the amino group and the carboxy group of glutamic acid, protective groups (Fmoc group and tBu group, respectively) had been attached in advance, DCC (2.6 g, 13 mmol), and DMAP (0.24 g, 1.9 mmol) were dissolved in dichloromethane (40 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) (((9H-fluoren-9-yl)methoxy)carbonyl)glutamate (6.8 g, 7.6 mmol, 79%).

Step (b7): Synthesis of 5-(tert-butyl) 1-((9Z,27Z)-hexatriaconta-9,27-dien-18-yl) glutamate

[Formula 31]

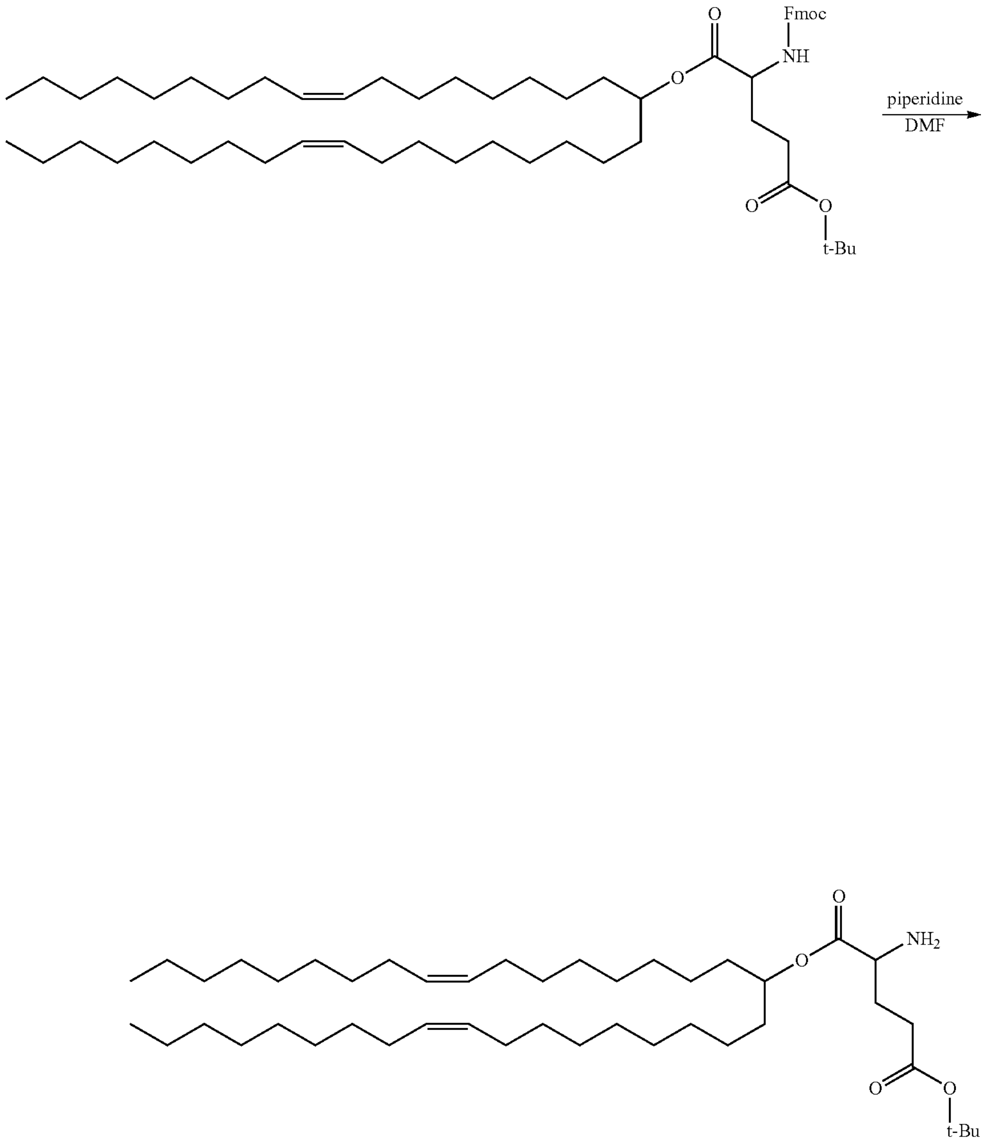

5-(tert-Butyl) 1-((9Z,27Z)-hexatriaconta-9,27-dien-18-yl) (((9H-fluoren-9-yl)methoxy)carbonyl)glutamate (3.6 g, 3.8 mmol) obtained in step (b6) was dissolved in a 20% piperidine/DMF solution (40 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) glutamate (1.6 g, 2.3 mmol, 58%).

Step (b8): Synthesis of 5-(tert-butyl) 1-((9Z,27Z)-hexatriaconta-9,27-dien-18-yl) N2-(((9H-fluoren-9-yl)methoxy)carbonyl)-Nw-((2,2,4,6,7-pentamethyl-2,3-dihydrobenzofuran-5-yl)sulfonyl) arginylglutamate

[Formula 32]

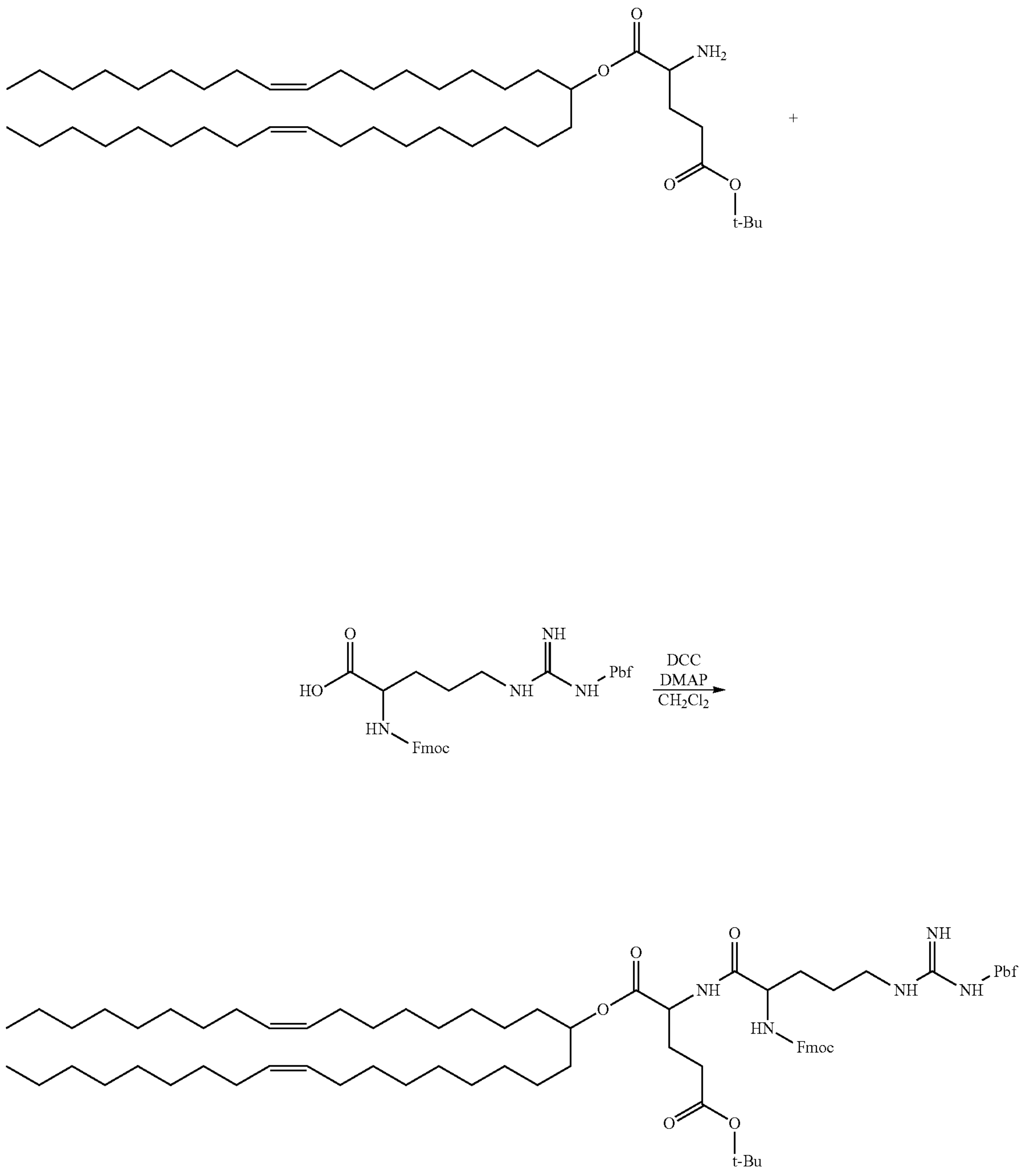

5-(tert-Butyl) 1-((9Z,27Z)-hexatriaconta-9,27-dien-18-yl) glutamate (1.6 g, 2.3 mmol) obtained in step (b7), Fmoc-Arg(Pbf)-OH (2.95 g, 4.5 mmol) in which to the amino group and the guanidino group of arginine, protective groups (Fmoc group and Pbf group, respectively) had been attached in advance, and DCC (0.65 g, 4.5 mmol) were dissolved in dichloromethane (10 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) N2-(((9H-fluoren-9-yl)methoxy)carbonyl)-Nw-((2,2,4,6,7-pentamethyl-2,3-dihydrobenzofuran-5-yl)sulfonyl)arginylglutamate (2.8 g, 2.1 mmol, 92%).

Step (b9): Synthesis of 5-(tert-butyl) 1-((9Z,27Z)-hexatriaconta-9,27-dien-18-yl) Nw-((2,2,4,6,7-pentamethyl-2,3-dihydrobenzofuran-5-yl)sulfonyl)arginylglutamate

[Formula 33]

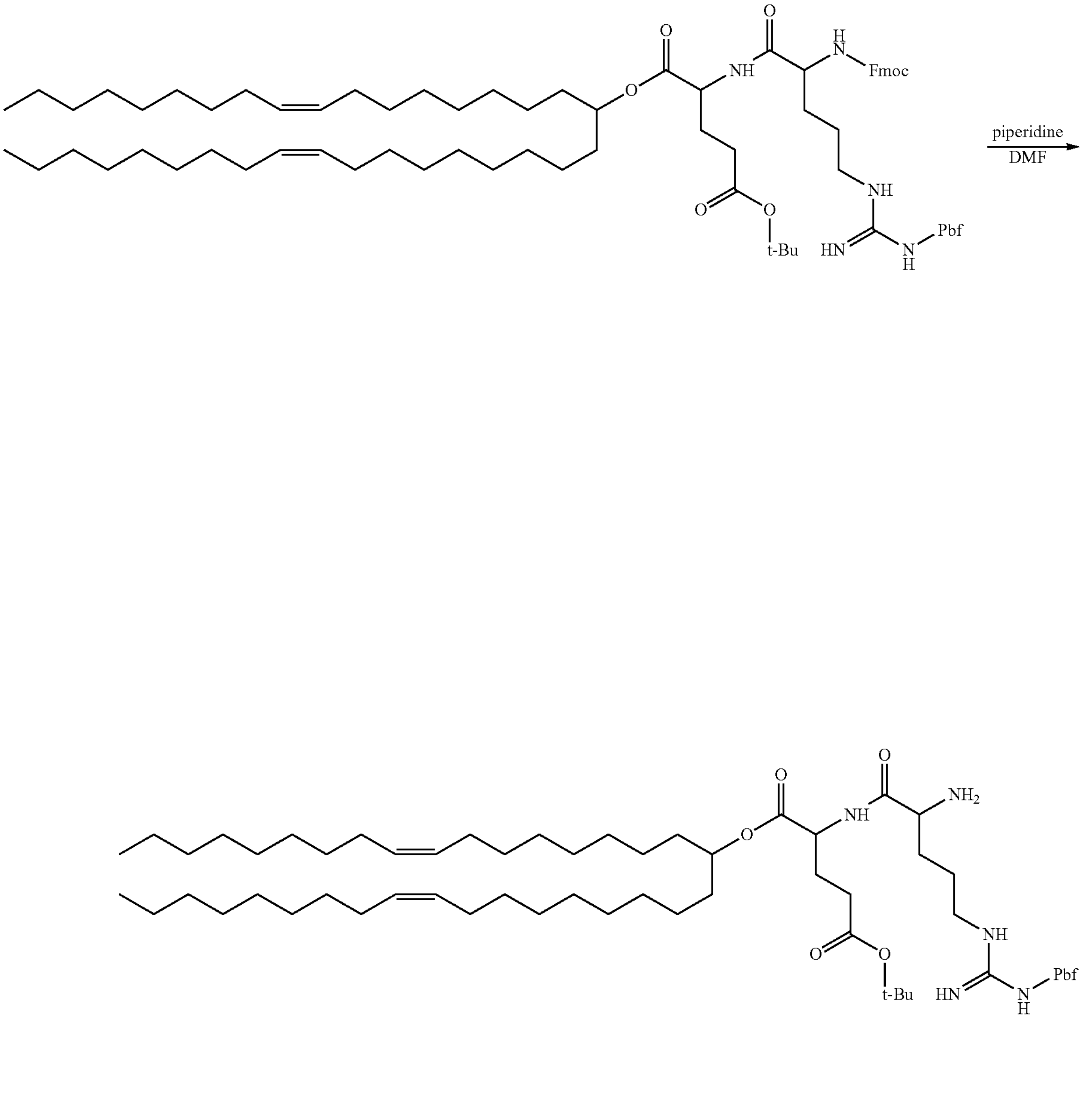

5-(tert-Butyl) 1-((9Z,27Z)-hexatriaconta-9,27-dien-18-yl) N2-(((9H-fluoren-9-yl)methoxy)carbonyl)-Nw-((2,2,4,6,7-pentamethyl-2,3-dihydrobenzofuran-5-yl)sulfonyl)arginylglutamate (2.8 g, 2.1 mmol) obtained in step (b8) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) Nw-((2,2,4,6,7-pentamethyl-2,3-dihydrobenzofuran-5-yl)sulfonyl)arginylglutamate (1.2 g, 1.4 mmol, 68%).

Step (b10): Synthesis of 4-(2-amino-5-guanidino-pentanamido)-5-(((9Z,27Z)-hexatriaconta-9,27-dien-18-yl)oxy)-5-oxopentanoic acid (lipid (Ib))

[Formula 34]

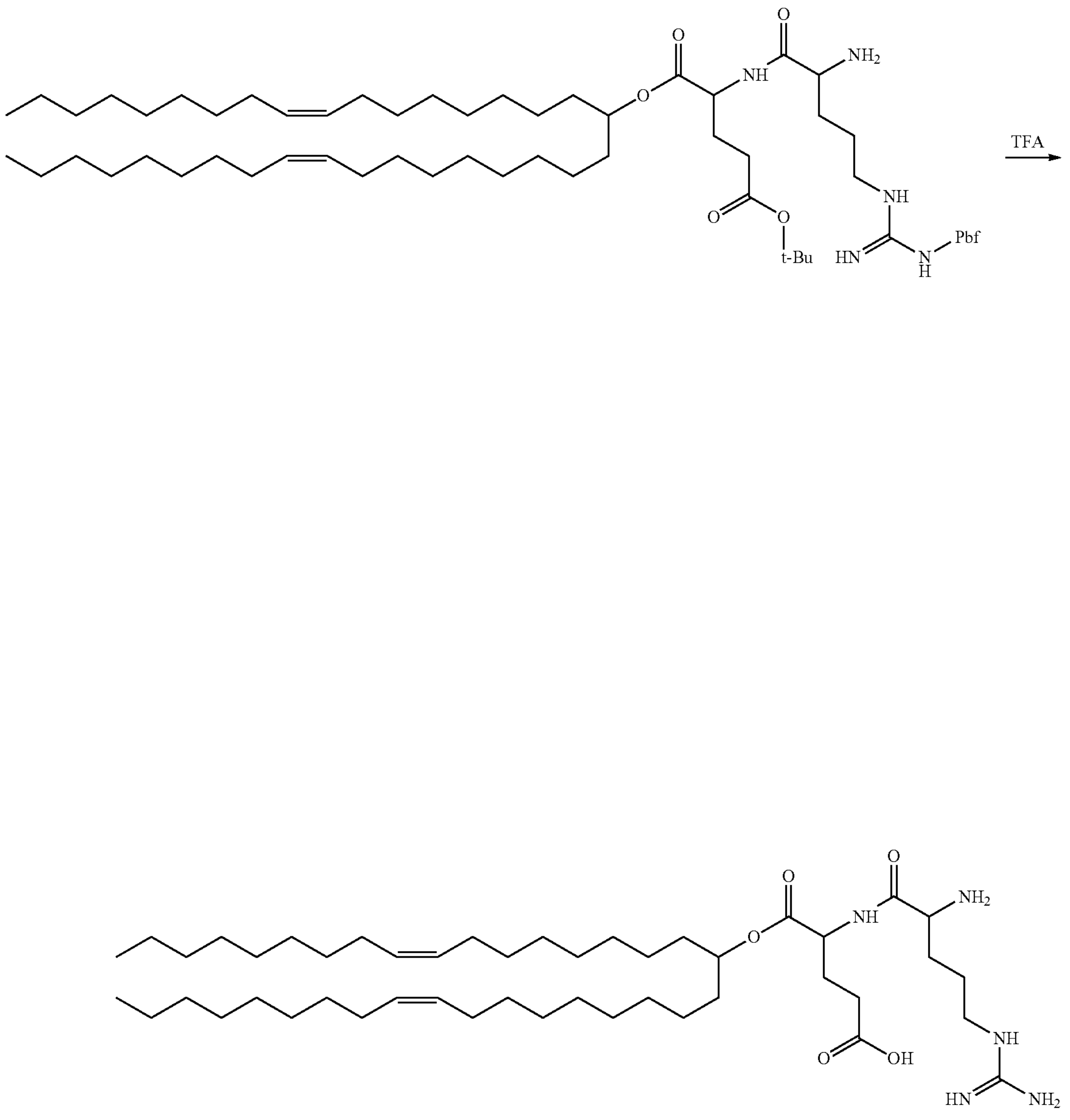

5-(tert-Butyl) 1-((9Z,27Z)-hexatriaconta-9,27-dien-18-yl) Nw-((2,2,4,6,7-pentamethyl-2,3-dihydrobenzofuran-5-yl)sulfonyl)arginylglutamate (1.2 g, 1.4 mmol) obtained in step (b9) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target 4-(2-amino-5-guanidinopentanamido)-5-(((9Z,27Z)-hexatriaconta-9,27-dien-18-yl)oxy)-5-oxopentanoic acid (lipid (Ib)) (0.3 g, 0.37 mmol, 27%).

$^{1}$H-NMR (400 MHz, CHLOROFORM-D) δ 5.43-5.19 (4H), 5.09-4.96 (1H), 4.91-4.74 (1H), 4.69-4.46 (1H), 3.71-3.52 (2H), 3.33-2.99 (2H), 2.58-2.31 (2H), 2.03-1.84 (8H), 1.81-1.69 (2H), 1.68-1.42 (6H), 1.41-0.98 (46H), 0.96-0.71 (6H) $[C_{47}H_{89}N_5O_5H]^+$: 804.75

Example 3

Synthesis of (9Z,27Z)-hexatriaconta-9,27-dien-18-ylarginylhistidinate (hereinafter also referred to as lipid (Ic))

Lipid (Ic) is a lipid in which the first amino acid of lipid (Ia) is changed to His. Hereinafter, a method for synthesizing lipid (Ic) will be described. The step of synthesizing a lipophilic region in the synthesis step is the same as the steps of step (a1) to step (a5) for lipid (Ia), and thus will be omitted.

Step (c6): Synthesis of (9Z,27Z)-hexatriaconta-9,27-dien-18-yl Na-(((9H-fluoren-9-yl)methoxy)carbonyl)-Nt-tritylhistidinate

[Formula 35]

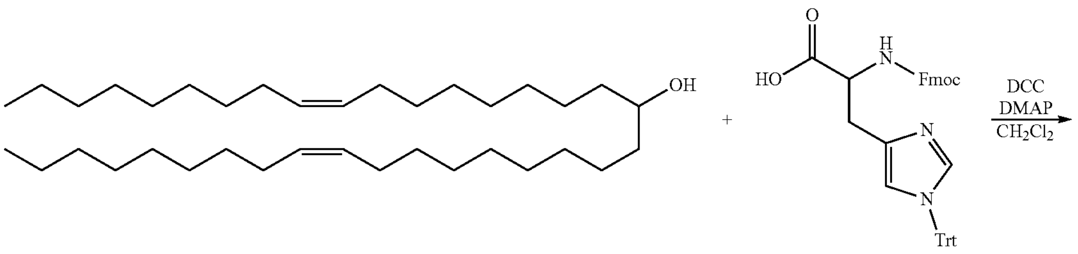

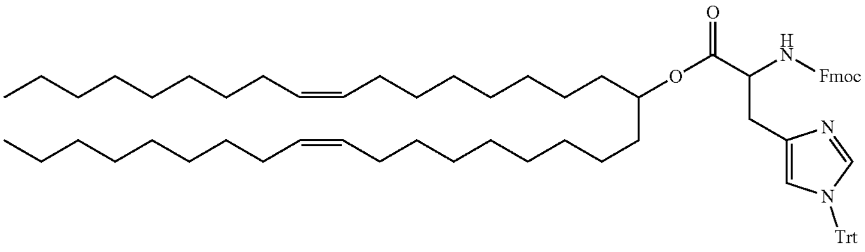

(9Z,27Z)-Hexatriaconta-9,27-dien-18-01 (3.0 g, 5.8 mmol) obtained in step (a5), Fmoc-His(Trt)-OH (4.3 g, 6.9 mmol) in which to the amino group and the imidazole group of histidine, protective groups (Fmoc group and Trt group, respectively) had been attached in advance, DCC (1.8 g, 8.6 mmol), and DMAP (0.10 g, 0.58 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl Na-(((9H-fluoren-9-yl)methoxy)carbonyl)-Nt-tritylhistidinate (3.8 g, 3.4 mmol, 58%).

Step (c7): Synthesis of (9Z,27Z)-hexatriaconta-9,27-dien-18-yl-Nt-tritylhistidinate

[Formula 36]

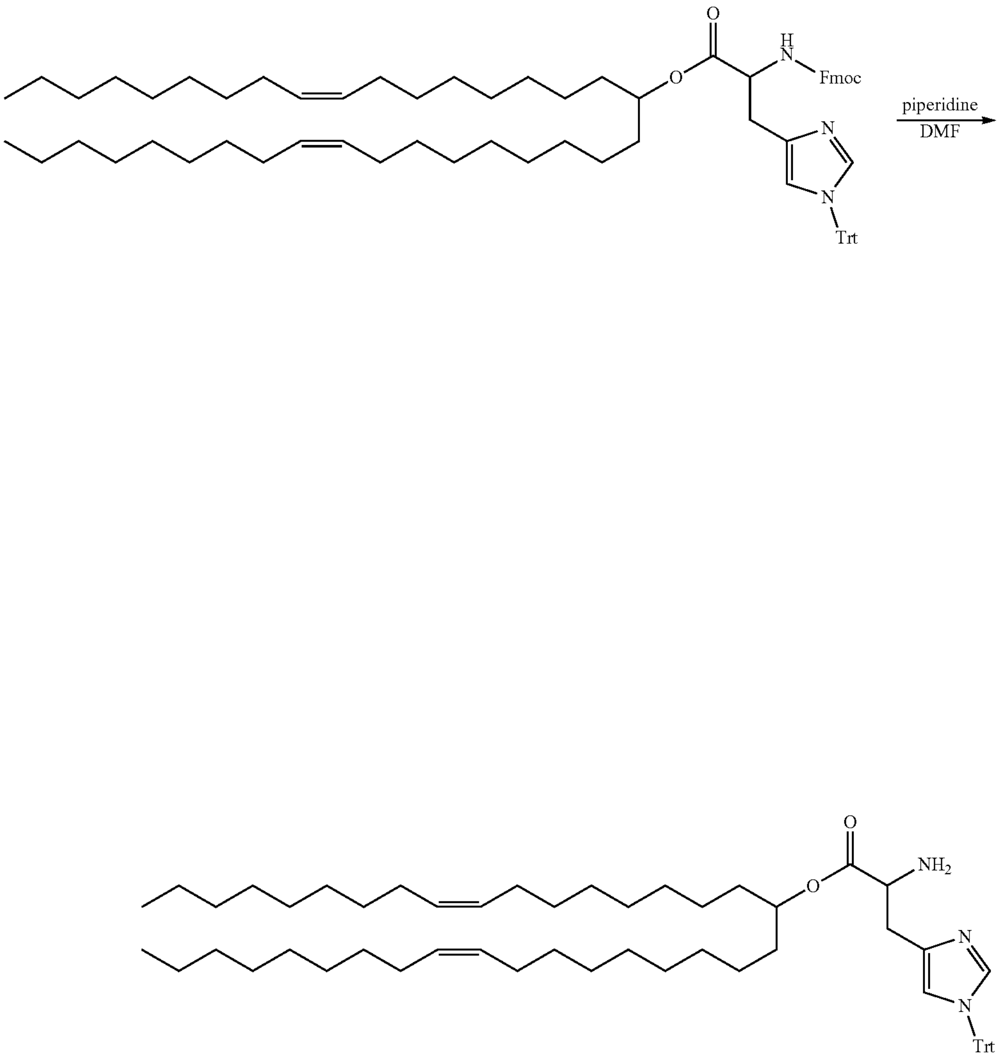

(9Z,27Z)-Hexatriaconta-9,27-dien-18-yl Na-(((9H-fluoren-9-yl)methoxy)carbonyl)-Nt-tritylhistidinate (3.8 g, 3.4 mmol) obtained in step (c6) was dissolved in a 20% piperidine/DMF solution (40 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl-Nt-tritylhistidinate (2.0 g, 2.2 mmol, 53%).

Step (c8): Synthesis of (9Z,27Z)-hexatriaconta-9,27-dien-18-yl Na—(N2-(((9H-fluoren-9-yl)methoxy)carbonyl)-Nw-(2,2,4,6,7-pentamethyl-2,3-dihydrobenzofuran-5-yl)arginyl)-Nt-tritylhistidinate

[Formula 37]

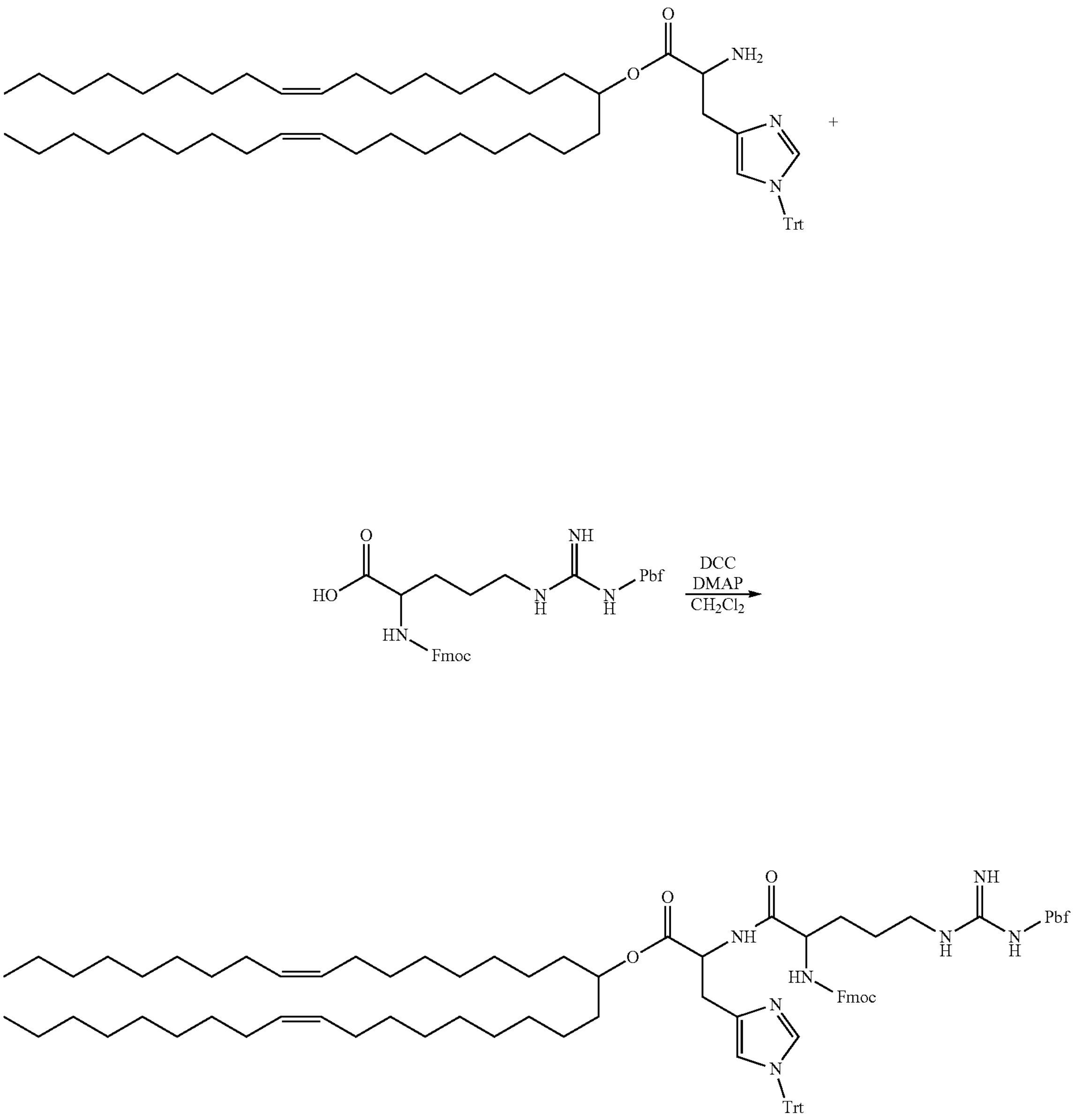

(9Z,27Z)-Hexatriaconta-9,27-dien-18-yl-Nt-tritylhistidinate (2.2 g, 3.0 mmol) obtained in step (c7), Fmoc-Arg(Pbf)-OH (1.7 g, 2.6 mmol) in which to the amino group and the guanidino group of arginine, protective groups (Fmoc group and Pbf group, respectively) had been attached in advance, DCC (0.67 g, 3.5 mmol), and DMAP (27 mg, 0.10 mmol) were dissolved in dichloromethane (20 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl Na—(N2-(((9H-fluoren-9-yl)methoxy)carbonyl)-Nw-(2,2,4,6,7-pentamethyl-2,3-dihydrobenzofuran-5-yl)arginyl)-Nt-tritylhistidinate (2.3 g, 1.6 mmol, 72%).

Step (c9): Synthesis of (9Z,27Z)-hexatriaconta-9,27-dien-18-yl Na—(Nw-(2,2,4,6,7-pentamethyl-2,3-dihydrobenzofuran-5-yl)arginyl)-Nt-tritylhistidinate

[Formula 38]

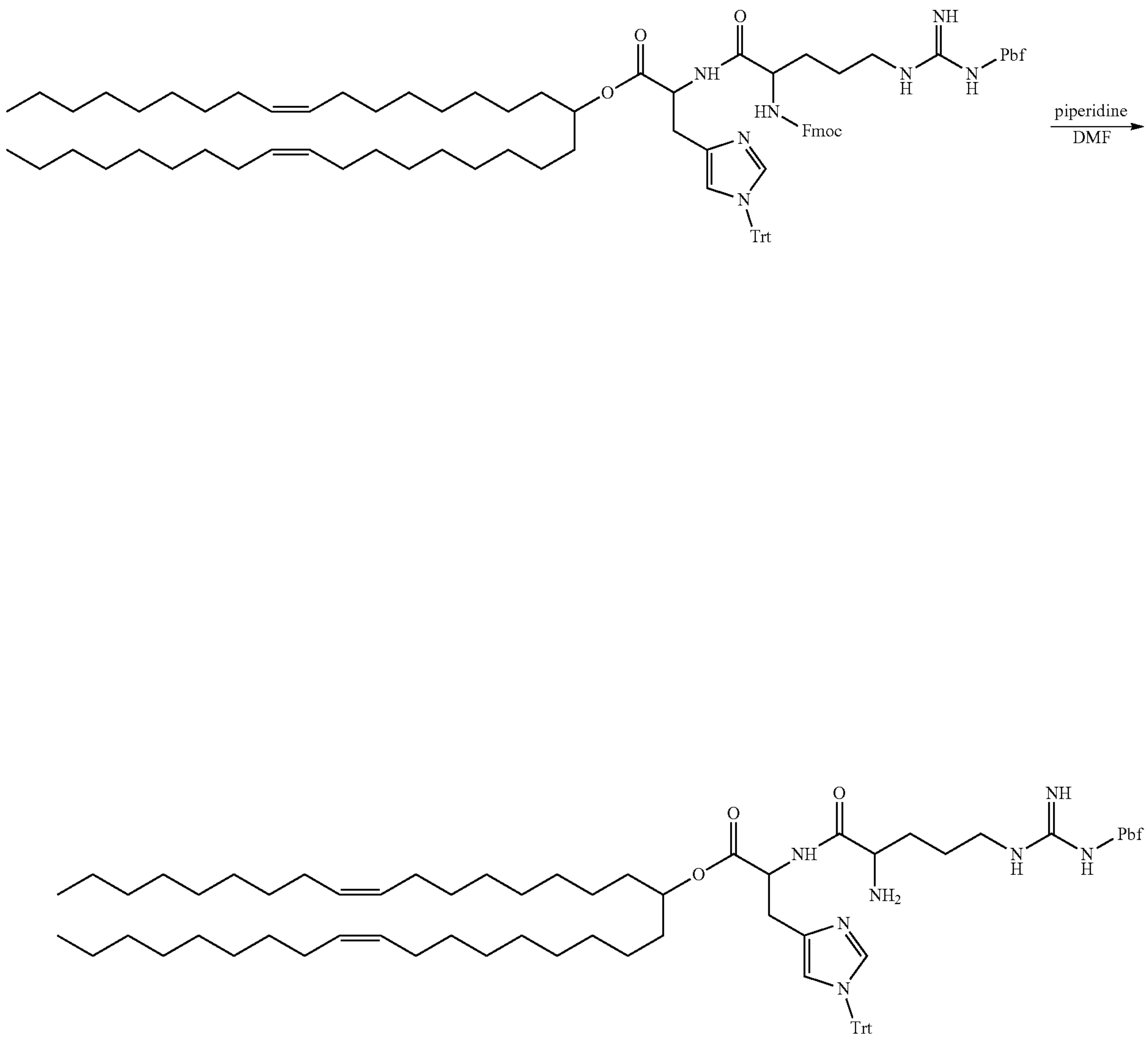

(9Z,27Z)-Hexatriaconta-9,27-dien-18-yl Na—(N2-(((9H-fluoren-9-yl)methoxy)carbonyl)-Nw-(2,2,4,6,7-pentamethyl-2,3-dihydrobenzofuran-5-yl)arginyl)-Nt-tritylhistidinate (2.3 g, 1.6 mmol) obtained in step (c8) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl Na—(Nw-(2,2,4,6,7-pentamethyl-2,3-dihydrobenzofuran-5-yl)arginyl)-Nt-tritylhistidinate (1.5 g, 1.2 mmol, 75%).

Step (c10): Synthesis of (9Z,27Z)-hexatriaconta-9,27-dien-18-yl arginylhistidinate (lipid (Ic))

[Formula 39]

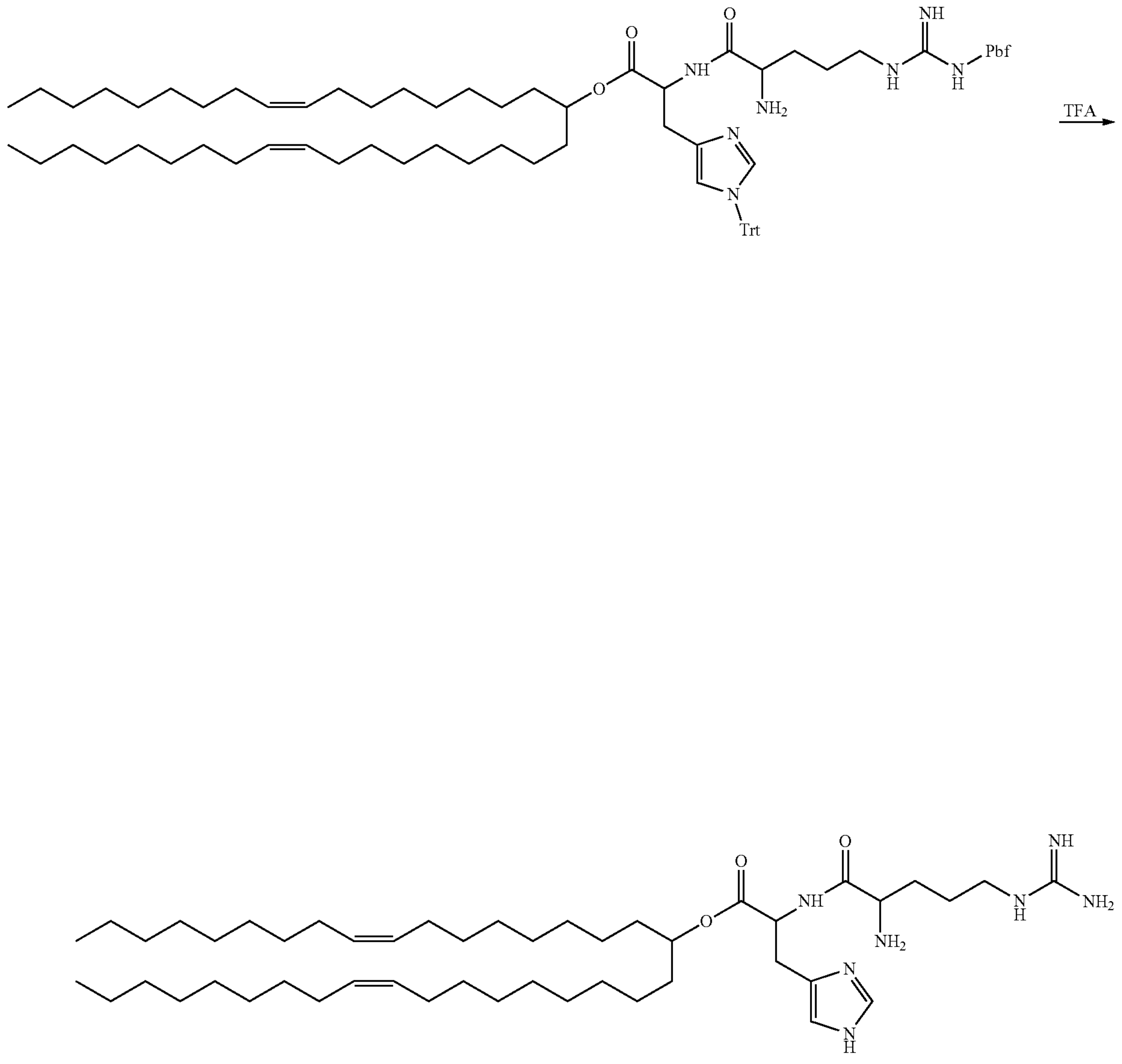

(9Z,27Z)-Hexatriaconta-9,27-dien-18-yl Na—(Nw-(2,2,4,6,7-pentamethyl-2,3-dihydrobenzofuran-5-yl)arginyl)-Nt-tritylhistidinate (1.5 g, 1.2 mmol) obtained in step (c9) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target (9Z,27Z)-hexatriaconta-9,27-dien-18-yl arginylhistidinate (lipid (Ic)) (0.2 g, 0.26 mmol, 22%).

$^1$H-NMR (400 MHz, CHLOROFORM-D) δ 7.86-7.44 (1H), 7.09-6.74 (1H), 5.40-5.22 (4H), 4.91-4.78 (1H), 4.16-3.97 (1H), 3.78-3.31 (3H), 3.27-3.06 (2H), 2.10-1.84 (8H), 1.84-1.60 (2H), 1.60-1.47 (6H), 1.36-1.00 (46H), 0.93-0.76 (6H) $[C_{48}H_{89}N_7O_3H]^+$: 812.74

Example 4

Synthesis of (9Z,27Z)-hexatriaconta-9,27-dien-18-yl (2S)-2-((S)-2-amino-5-guanidinopentanamido)-3-hydroxypropionate (hereinafter also referred to as lipid (Id))

Lipid (Id) is a lipid in which the first amino acid of lipid (Ia) is changed to Ser. Hereinafter, a method for synthesizing lipid (Id) will be described. The step of synthesizing a lipophilic region in the synthesis step is the same as the steps of step (a1) to step (a5) for lipid (Ia), and thus will be omitted.

Step (d6): Synthesis of (9Z,27Z)-hexatriaconta-9,27-dien-18-yl N-(((9H-fluoren-9-yl)methoxy)carbonyl)-O-(tert-butyl)serinate

[Formula 40]

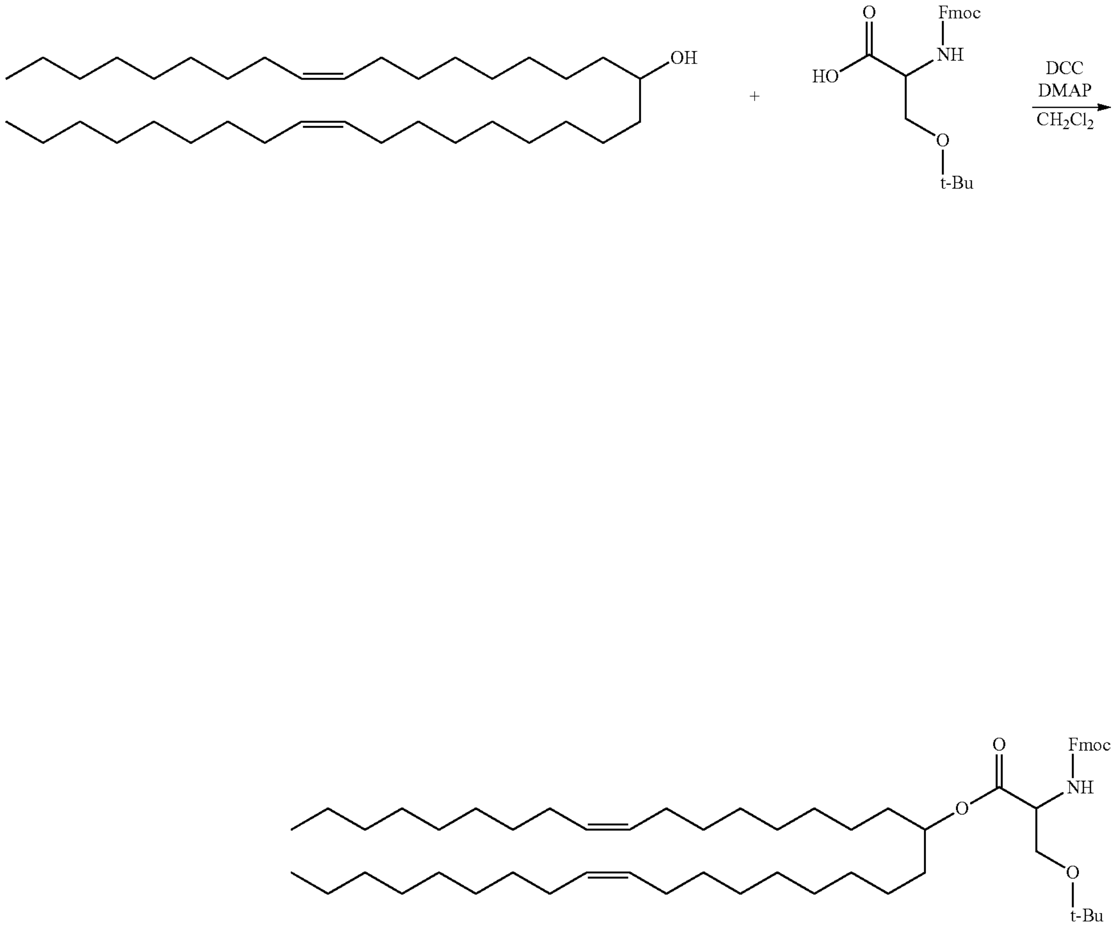

(9Z,27Z)-Hexatriaconta-9,27-dien-18-01 (3.0 g, 5.7 mmol) obtained in step (a5), Fmoc-Ser(tBu)-OH (2.7 g, 6.9 mmol) in which to the amino group and the hydroxy group of serine, protective groups (Fmoc group and tBu group, respectively) had been attached in advance, DCC (1.8 g, 8.7 mmol), and DMAP (70 mg, 0.58 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl N-(((9H-fluoren-9-yl)methoxy)carbonyl)-O-(tert-butyl)serinate (3.7 g, 4.2 mmol, 72%).

Step (d7): Synthesis of (9Z,27Z)-hexatriaconta-9,27-dien-18-yl O-(tert-butyl)serinate

[Formula 41]

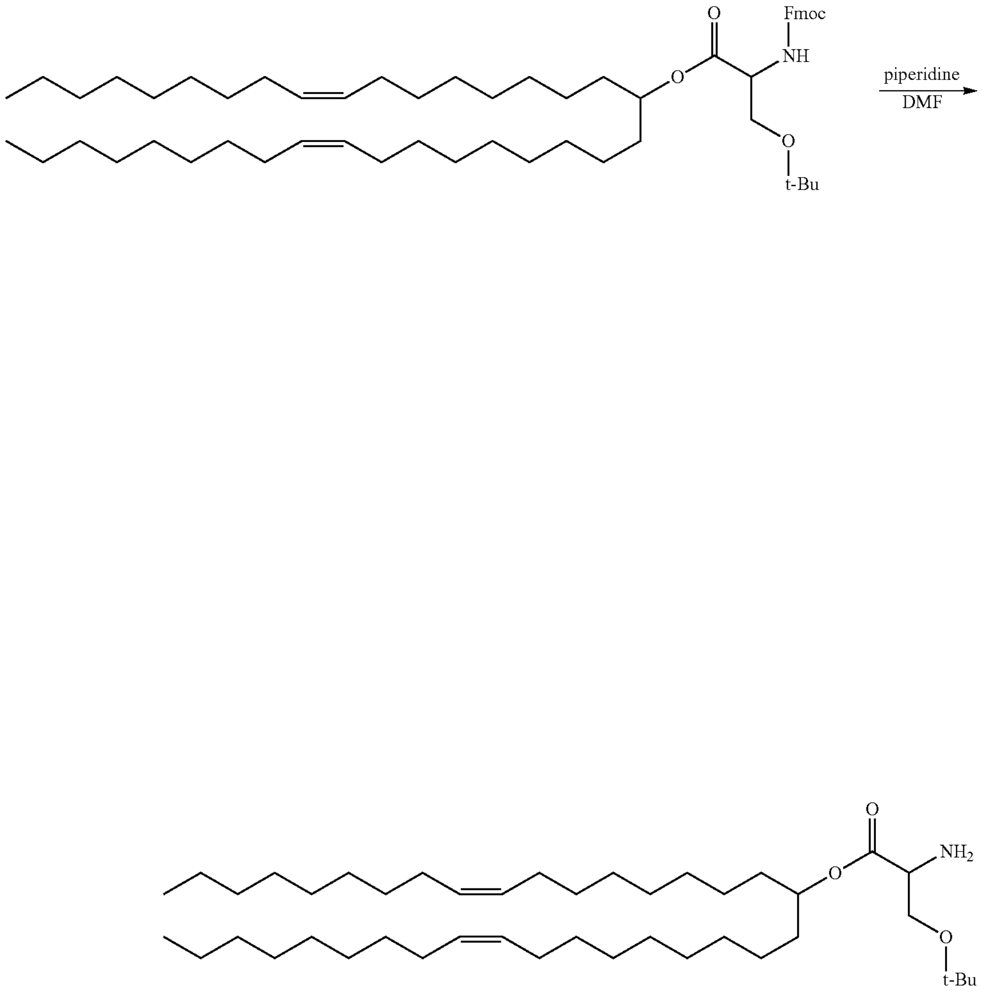

(9Z,27Z)-Hexatriaconta-9,27-dien-18-yl N-(((9H-fluoren-9-yl)methoxy)carbonyl)-O-(tert-butyl)serinate (3.7 g, 4.2 mmol) obtained in step (d6) was dissolved in a 20% piperidine/DMF solution (40 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl O-(tert-butyl)serinate (2.4 g, 3.6 mmol, 86%).

Step (d8): Synthesis of (9Z,27Z)-hexatriaconta-9,27-dien-18-yl N—(N2-(((9H-fluoren-9-yl)methoxy)carbonyl)-Nw-(2,2,4,6,7-pentamethyl-2,3-dihydrobenzofuran-5-yl)arginyl)-O-(tert-butyl)serinate

[Formula 42]

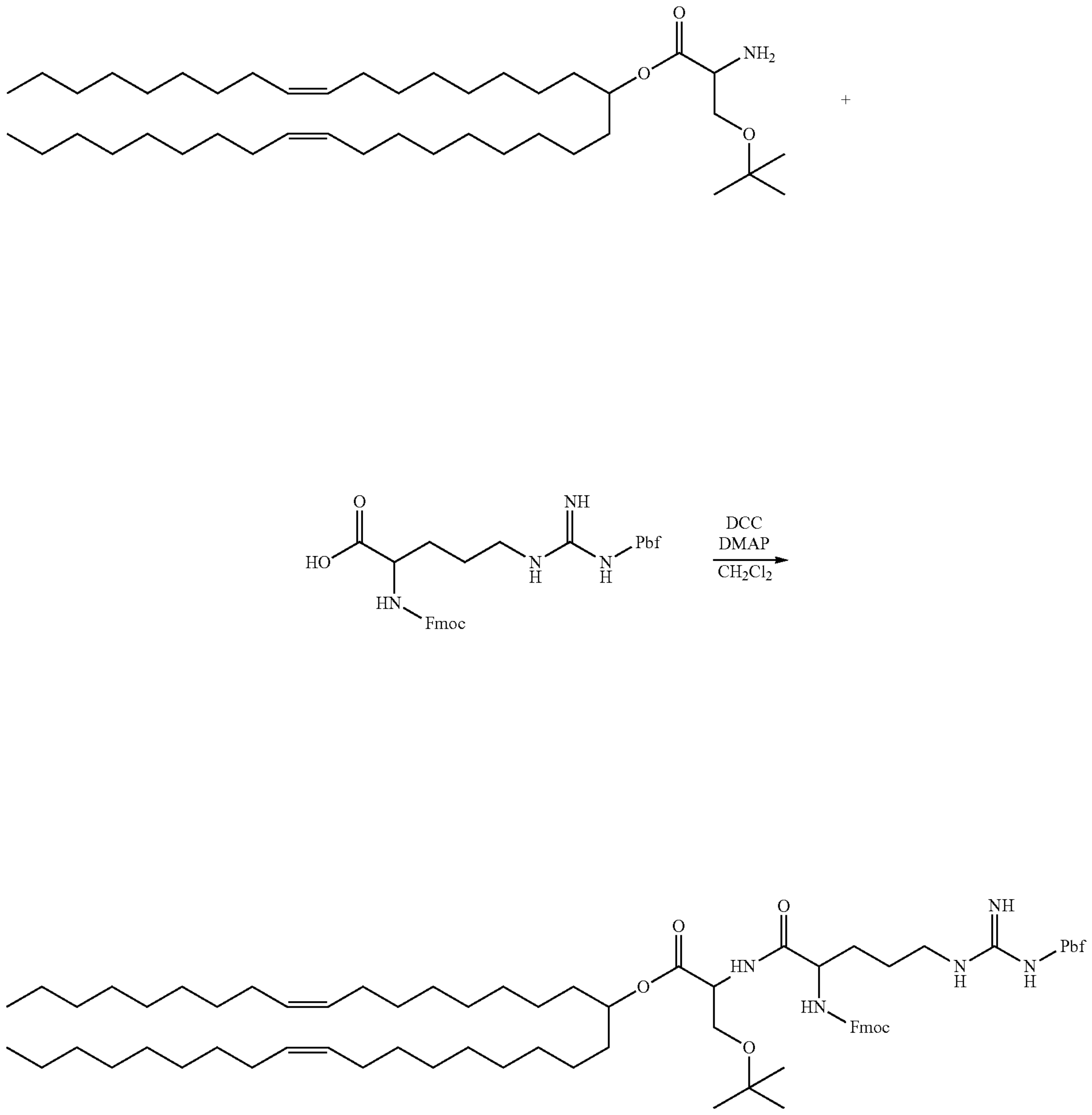

(9Z,27Z)-Hexatriaconta-9,27-dien-18-yl O-(tert-butyl) serinate (2.4 g, 3.6 mmol) obtained in step (d7), Fmoc-Arg (Pbf)-OH (2.8 g, 4.3 mmol) in which to the amino group and the guanidino group of arginine, protective groups (Fmoc group and Pbf group, respectively) had been attached in advance, DCC (1.1 g, 5.4 mmol), and DMAP (44 mg, 0.36 mmol) were dissolved in dichloromethane (24 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl N—(N2-(((9H-fluoren-9-yl)methoxy)carbonyl)-Nw-(2,2,4,6,7-pentamethyl-2,3-dihydrobenzofuran-5-yl)arginyl)-O-(tert-butyl)serinate (3.0 g, 2.4 mmol, 68%).

Step (d9): Synthesis of (9Z,27Z)-hexatriaconta-9,27-dien-18-yl O-(tert-butyl)-N—(Nw-(2,2,4,6,7-pentamethyl-2,3-dihydrobenzofuran-5-yl)arginyl) serinate

[Formula 43]

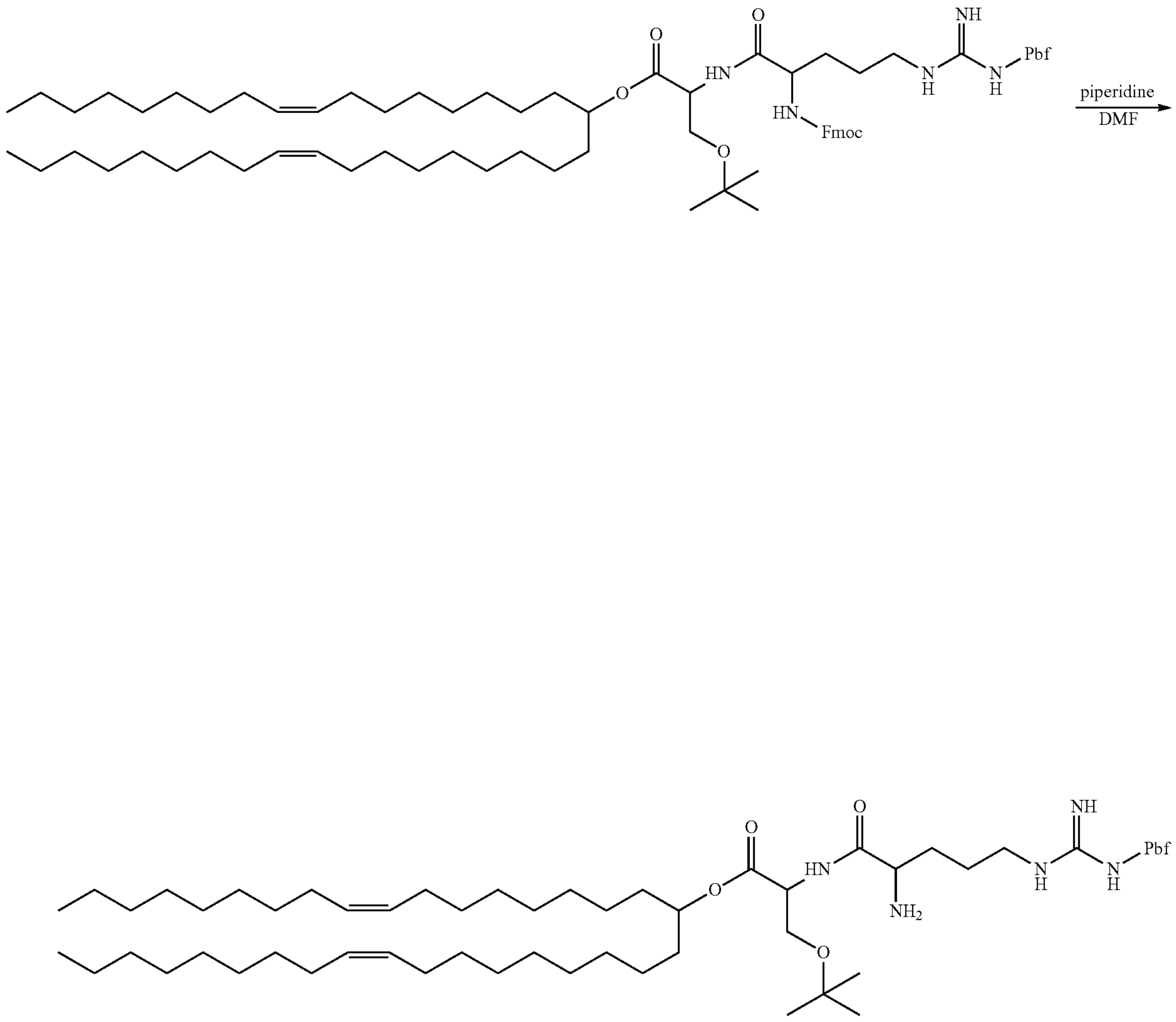

(9Z,27Z)-Hexatriaconta-9,27-dien-18-yl N—(N2-(((9H-fluoren-9-yl)methoxy)carbonyl)-Nw-(2,2,4,6,7-pentamethyl-2,3-dihydrobenzofuran-5-yl)arginyl)-O-(tert-butyl) serinate (3.0 g, 2.4 mmol) obtained in step (a8) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl O-(tert-butyl)-N—(Nw-(2,2,4,6,7-pentamethyl-2,3-dihydrobenzofuran-5-yl)arginyl)serinate (1.8 g, 1.8 mmol, 72%).

Step (d9): Synthesis of (9Z,27Z)-hexatriaconta-9,27-dien-18-yl arginylserinate (lipid (Id))

[Formula 44]

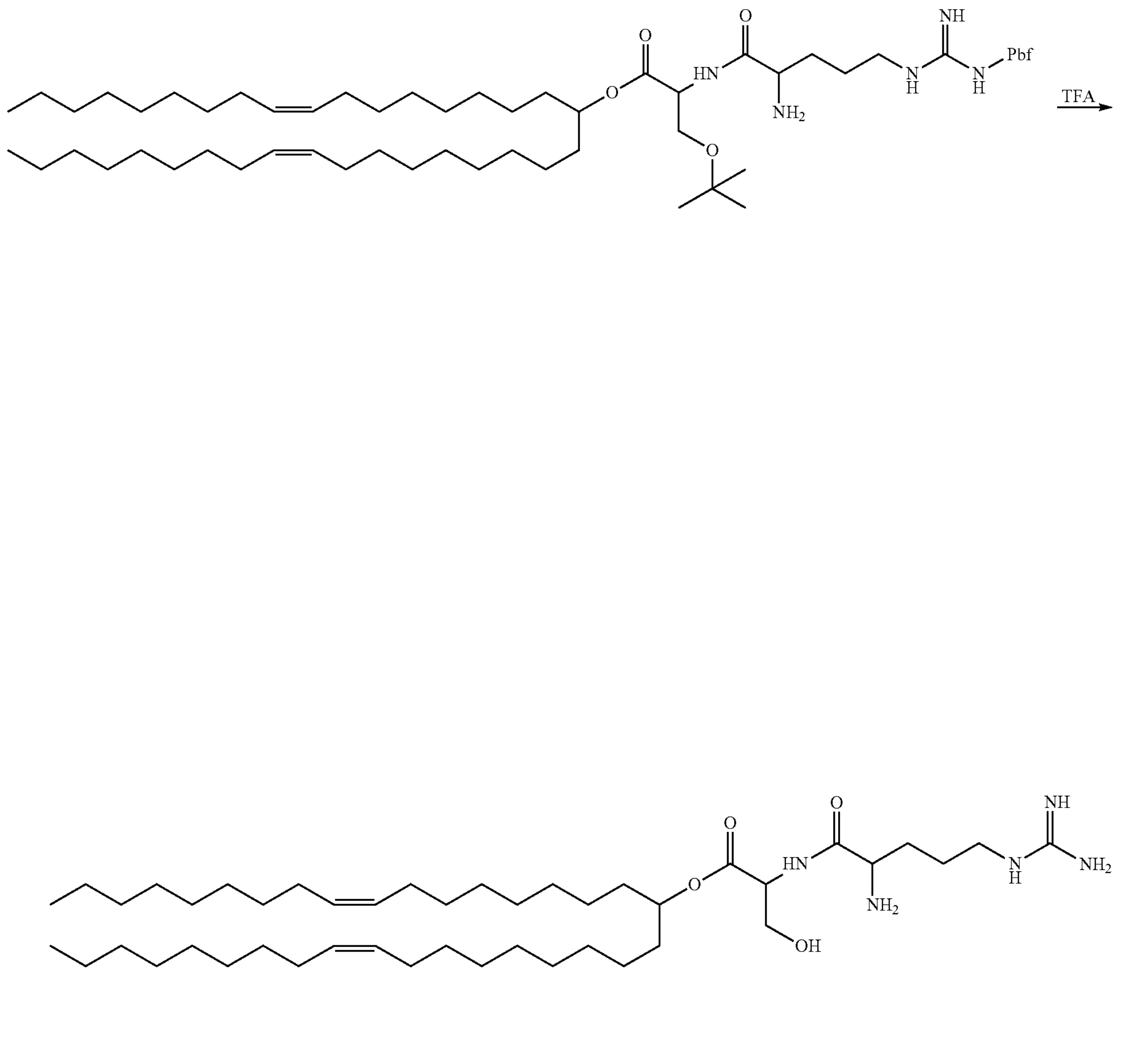

(9Z,27Z)-Hexatriaconta-9,27-dien-18-yl O-(tert-butyl)-N—(Nw-(2,2,4,6,7-pentamethyl-2,3-dihydrobenzofuran-5-yl)arginyl)serinate (1.8 g, 1.8 mmol) obtained in step (d8) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target (9Z,27Z)-hexatriaconta-9,27-dien-18-yl arginylserinate (lipid (Id)) (0.20 g, 0.26 mmol, 15%).

$^1$H-NMR (400 MHz, CHLOROFORM-D) δ 5.33 (dd, 4H), 4.81 (s, 2H), 4.70-3.46 (m, 3H), 3.46-2.81 (m, 2H), 2.27-1.85 (m, 10H), 1.85-1.37 (m, 6H), 1.37-0.93 (m, 46H), 0.87 (td, 6H)

$[C_{45}H_{87}N_5O_4H]^+$: 762.92

Example 5

Synthesis of (9Z,27Z)-hexatriaconta-9,27-dien-18-yl (2S)-2-((S)-2-amino-5-guanidinopentanamido)-3-hydroxybutanoate (hereinafter also referred to as lipid (Ie))

Lipid (Ie) is a lipid in which the first amino acid of lipid (Ia) is changed to Thr. Hereinafter, a method for synthesizing lipid (Ie) will be described. The step of synthesizing a lipophilic region in the synthesis step is the same as the steps of step (a1) to step (a5) for lipid (Ia), and thus will be omitted.

Step (e6): Synthesis of (9Z,27Z)-hexatriaconta-9,27-dien-18-yl (2S)-2-((((9H-fluoren-9-yl)methoxy)carbonyl)amino)-3-(tert-butoxy)butanoate

[Formula 45]

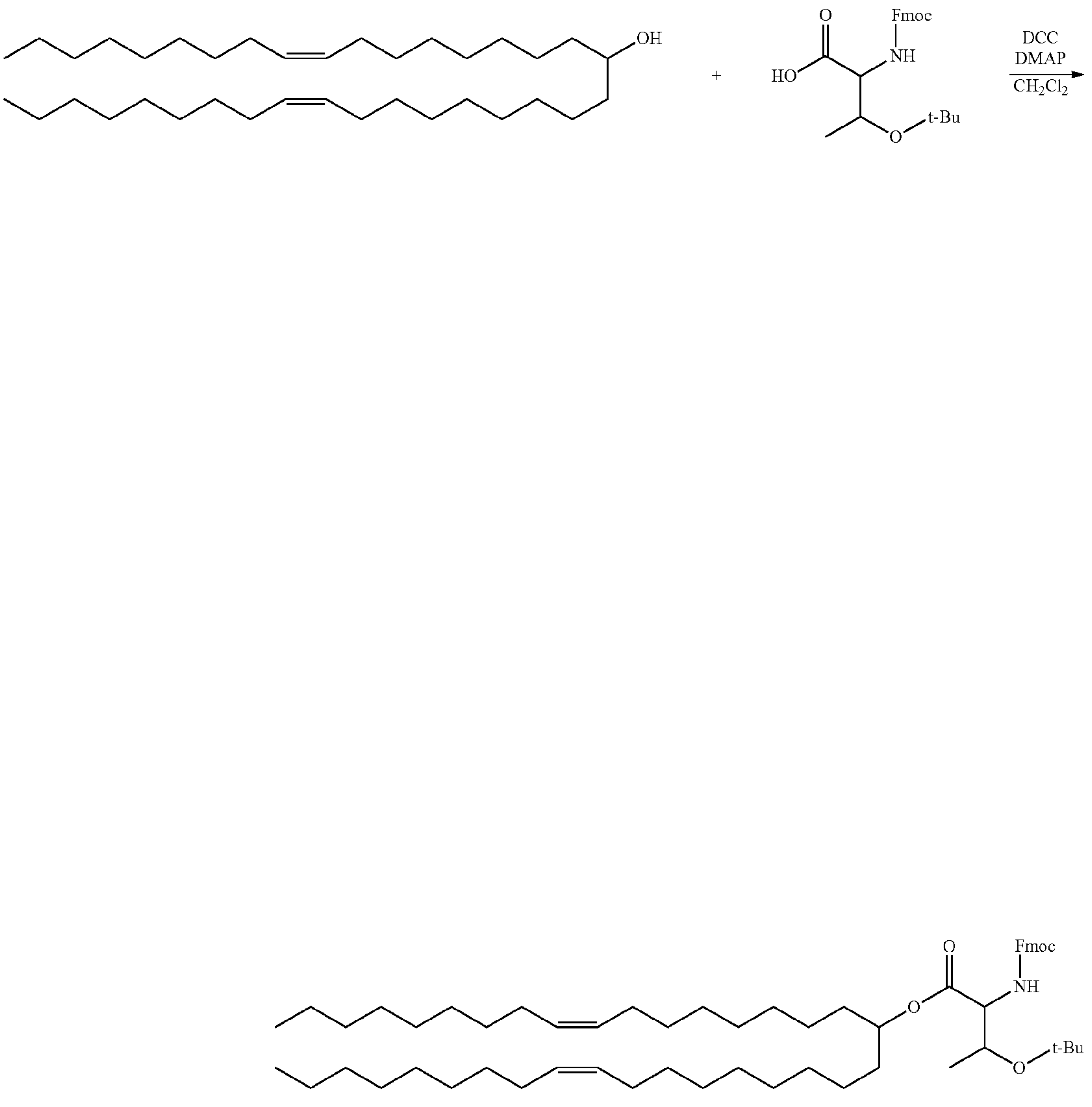

(9Z,27Z)-Hexatriaconta-9,27-dien-18-01 (5.0 g, 9.6 mmol) obtained in step (a5), Fmoc-Thr(tBu)-OH (4.6 g, 12 mmol) in which to the amino group and the hydroxy group of threonine, protective groups (Fmoc group and tBu group, respectively) had been attached in advance, DCC (2.6 g, 13 mmol), and DMAP (0.24 g, 1.9 mmol) were dissolved in dichloromethane (40 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl (2S)-2-((((9H-fluoren-9-yl)methoxy)carbonyl)amino)-3-(tert-butoxy)butanoate (6.8 g, 7.6 mmol, 79%).

Step (e7): Synthesis of (9Z,27Z)-hexatriaconta-9,27-dien-18-yl (2S)-2-amino-3-(tert-butoxy)butanoate

[Formula 46]

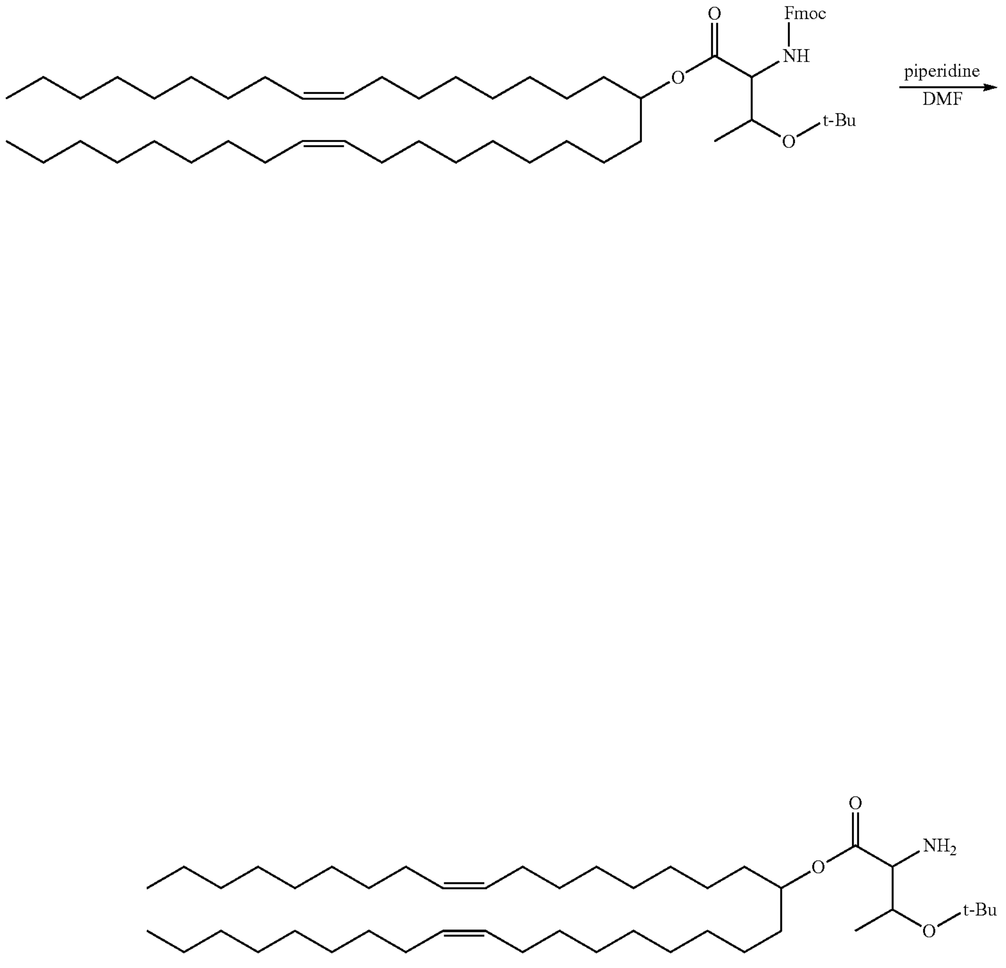

(9Z,27Z)-Hexatriaconta-9,27-dien-18-yl (2S)-2-((((9H-fluoren-9-yl)methoxy)carbonyl)amino)-3-(tert-butoxy)butanoate (5.0 g, 5.6 mmol) obtained in step (e6) was dissolved in a 20% piperidine/DMF solution (40 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl (2S)-2-amino-3-(tert-butoxy)butanoate (2.0 g, 3.0 mmol, 53%).

Step (e8): Synthesis of (9Z,27Z)-hexatriaconta-9,27-dien-18-yl (2S)-3-(tert-butoxy)-2-((S)-2-((tert-butoxycarbonyl)amino)-5-(3-((2,2,4,6,7-pentamethyl-2,3-dihydrobenzofuran-5-yl)sulfonyl)guanidino)pentanamido)butanoate

[Formula 47]

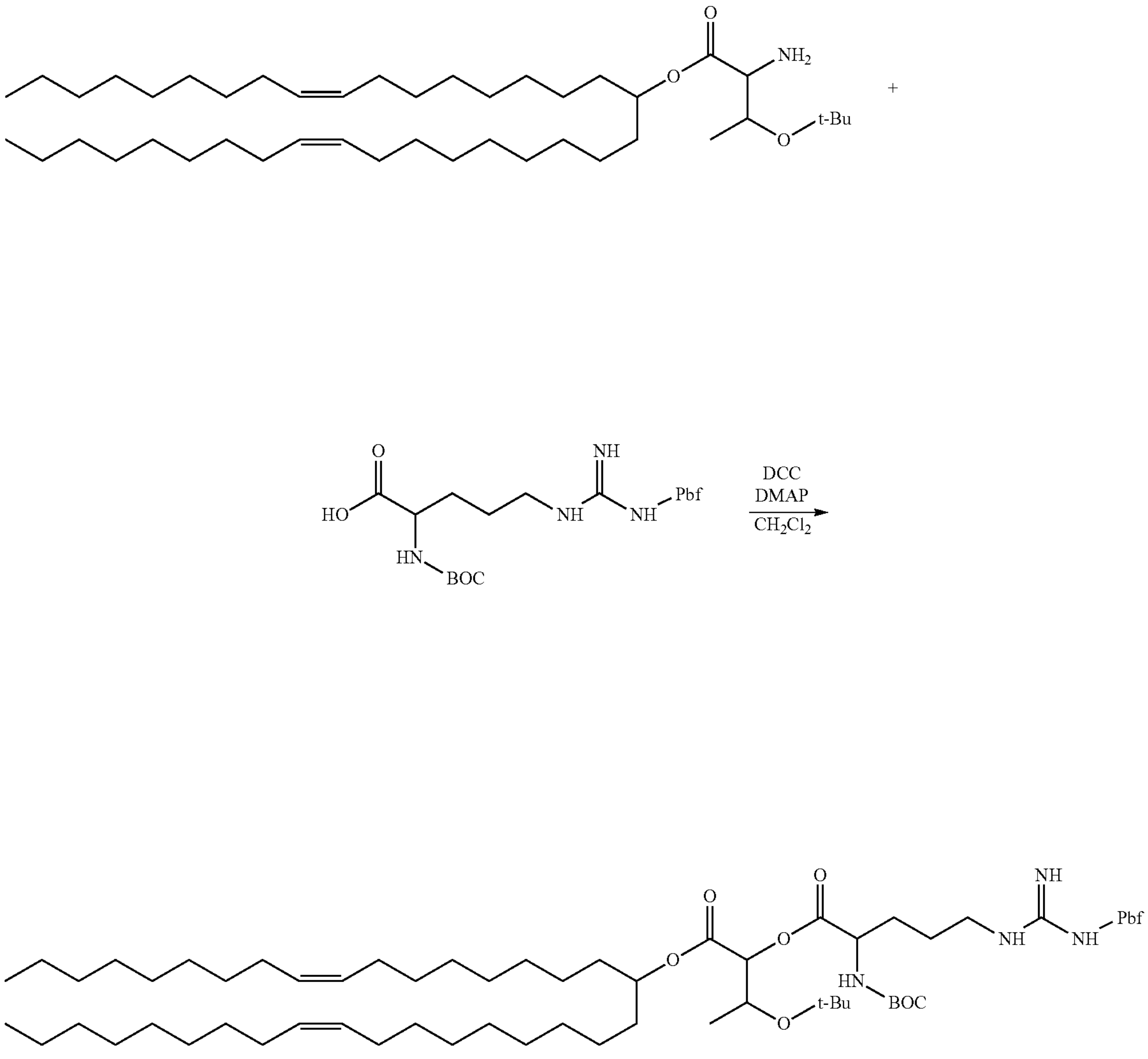

(9Z,27Z)-Hexatriaconta-9,27-dien-18-yl (2S)-2-amino-3-(tert-butoxy)butanoate (2.0 g, 3.0 mmol) obtained in step (e7), Boc-Arg(Pbf)-OH (1.7 g, 3.3 mmol) in which to the amino group and the guanidino group of arginine, protective groups (Boc group and Pbf group, respectively) had been attached in advance, DCC (0.73 g, 3.5 mmol), and DMAP (36 mg, 0.30 mmol) were dissolved in dichloromethane (20 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl (2S)-3-(tert-butoxy)-2-((S)-2-((tert-butoxycarbonyl)amino)-5-(3-((2,2,4,6,7-pentamethyl-2,3-dihydrobenzofuran-5-yl)sulfonyl) guanidino)pentanamido)butanoate (3.1 g, 2.6 mmol, 88%).

Step (e9): Synthesis of (9Z,27Z)-hexatriaconta-9,27-dien-18-yl (2S)-2-((S)-2-amino-5-guanidinopentanamido)-3-hydroxybutanoate (lipid (Ie))

[Formula 48]

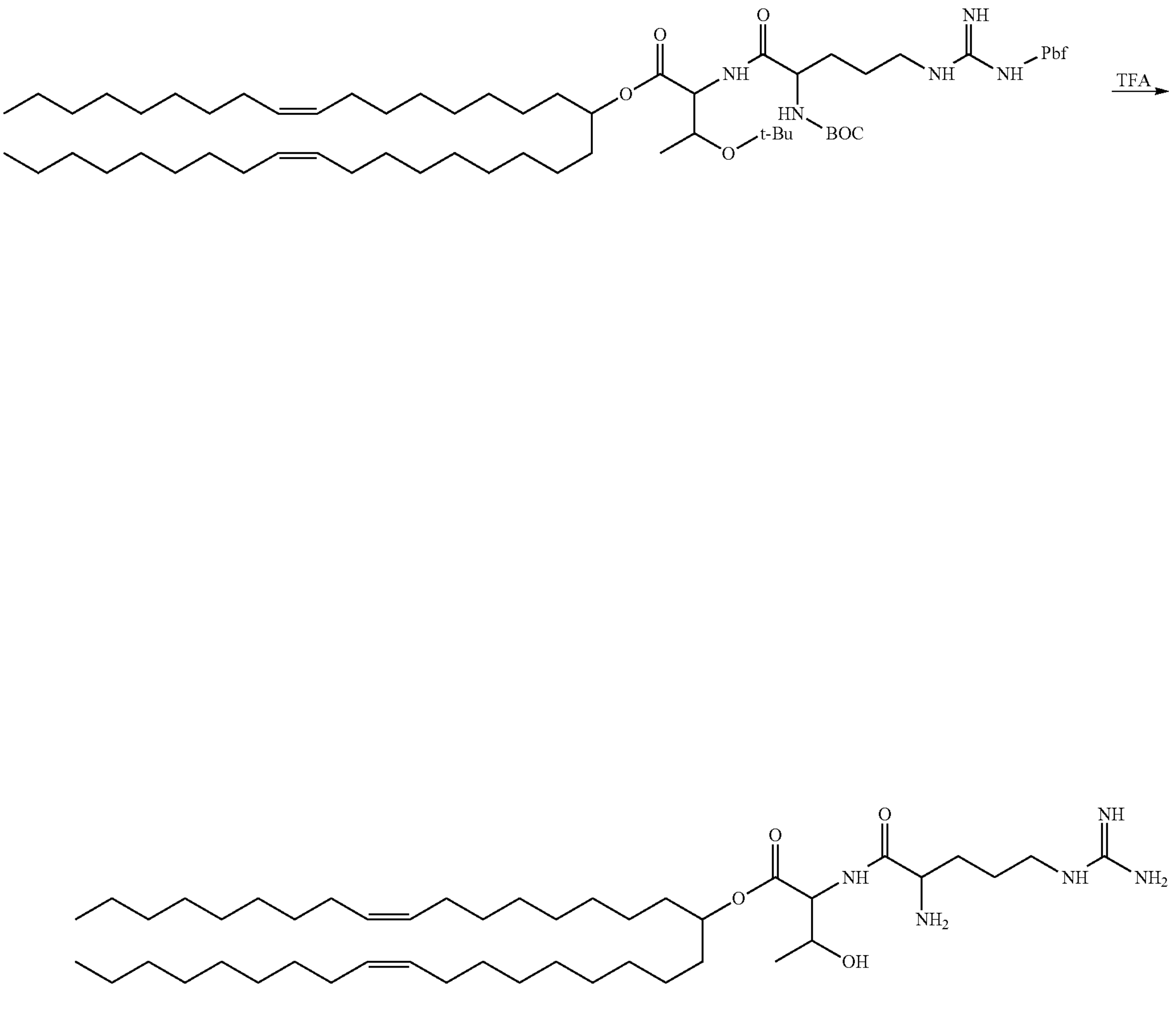

(9Z,27Z)-Hexatriaconta-9,27-dien-18-yl (2S)-3-(tert-butoxy)-2-((S)-2-((tert-butoxycarbonyl)amino)-5-(3-((2,2,4,6,7-pentamethyl-2,3-dihydrobenzofuran-5-yl)sulfonyl)guanidino)pentanamido)butanoate (2.0 g, 1.7 mmol) obtained in step (e8) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target (9Z,27Z)-hexatriaconta-9,27-dien-18-yl (2S)-2-((S)-2-amino-5-guanidinopentanamido)-3-hydroxybutanoate (lipid (Ie)) (0.3 g, 0.38 mmol, 20%).

$^1$H-NMR (400 MHz, CHLOROFORM-D) δ 5.45-5.19 (4H), 4.88-4.76 (1H), 4.45-4.32 (1H), 4.30-4.10 (2H), 3.28-2.98 (2H), 2.16-1.88 (10H), 1.88-1.62 (2H), 1.62-1.48 (4H), 1.39-0.94 (49H), 0.93-0.78 (6H)

$[C_{46}H_{89}N_5O_4H]^+$: 776.72

Example 6

Synthesis of (9Z,27Z)-hexatriaconta-9,27-dien-18-yl arginylmethioninate (hereinafter also referred to as lipid (If))

Lipid (If) is a lipid in which the first amino acid of lipid (Ia) is changed to Met. Hereinafter, a method for synthesizing lipid (If) will be described. The step of synthesizing a lipophilic region in the synthesis step is the same as the steps of step (a1) to step (a5) for lipid (Ia), and thus will be omitted.

Step (f6): Synthesis of (9Z,27Z)-hexatriaconta-9,27-dien-18-yl (((9H-fluoren-9-yl)methoxy)carbonyl) methioninate

[Formula 49]

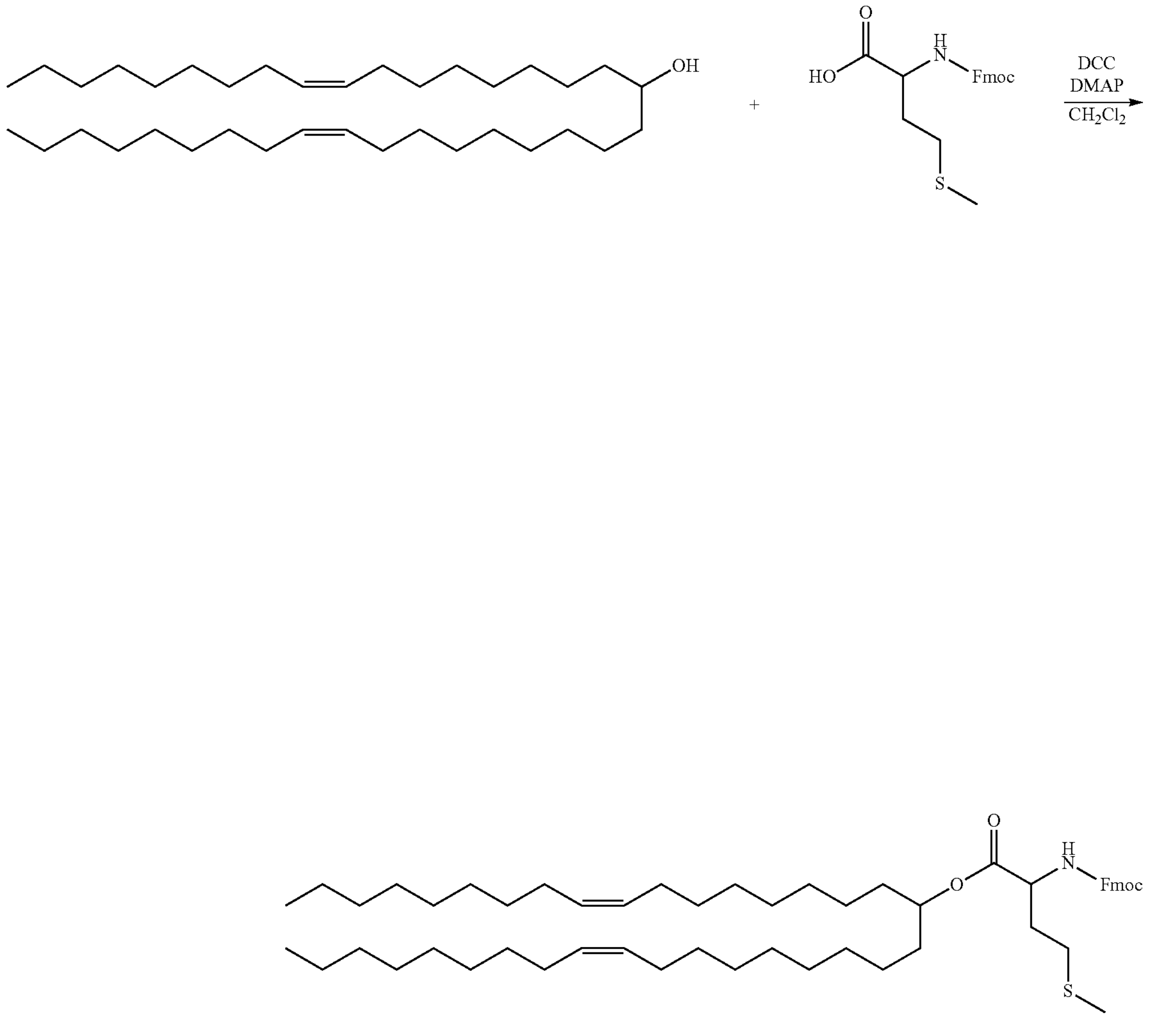

(9Z,27Z)-Hexatriaconta-9,27-dien-18-01 (3.0 g, 5.8 mmol) obtained in step (a5), Fmoc-Met-OH (2.7 g, 6.9 mmol) in which to the amino group of methionine, a protective group (Fmoc group) had been attached in advance, DCC (1.8 g, 8.7 mmol), and DMAP (70 mg, 0.58 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl (((9H-fluoren-9-yl)methoxy)carbonyl)methioninate (2.9 g, 3.4 mmol, 58%).

Step (f7): Synthesis of (9Z,27Z)-hexatriaconta-9,27-dien-18-yl methioninate

[Formula 50]

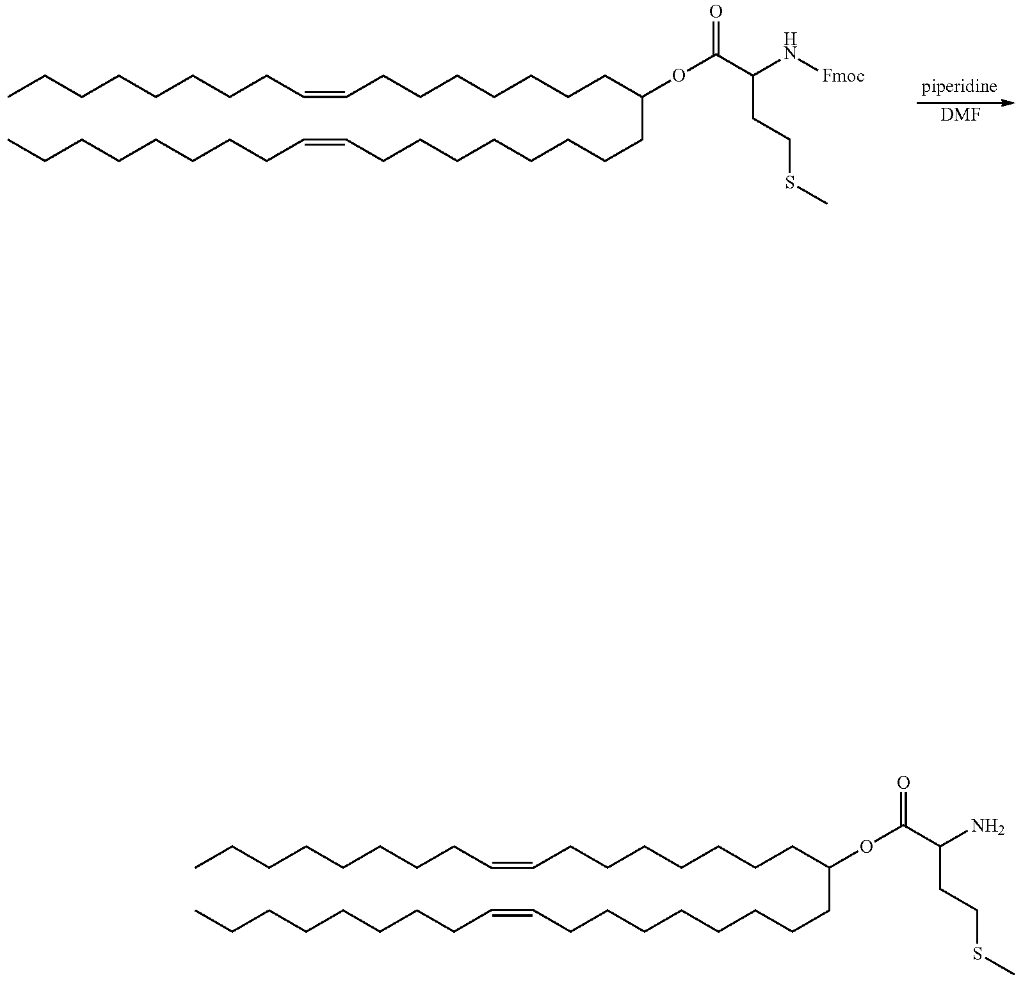

(9Z,27Z)-Hexatriaconta-9,27-dien-18-yl (((9H-fluoren-9-yl)methoxy)carbonyl)methioninate (2.9 g, 3.4 mmol) obtained in step (f6) was dissolved in a 20% piperidine/DMF solution (15 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl methioninate (1.9 g, 2.9 mmol, 87%).

Step (f8): Synthesis of (9Z,27Z)-hexatriaconta-9,27-dien-18-yl N2-(((9H-fluoren-9-yl)methoxy)carbonyl)-Nw-(2,2,4,6,7-pentamethyl-2,3-dihydrobenzofuran-5-yl)arginylmethioninate

[Formula 51]

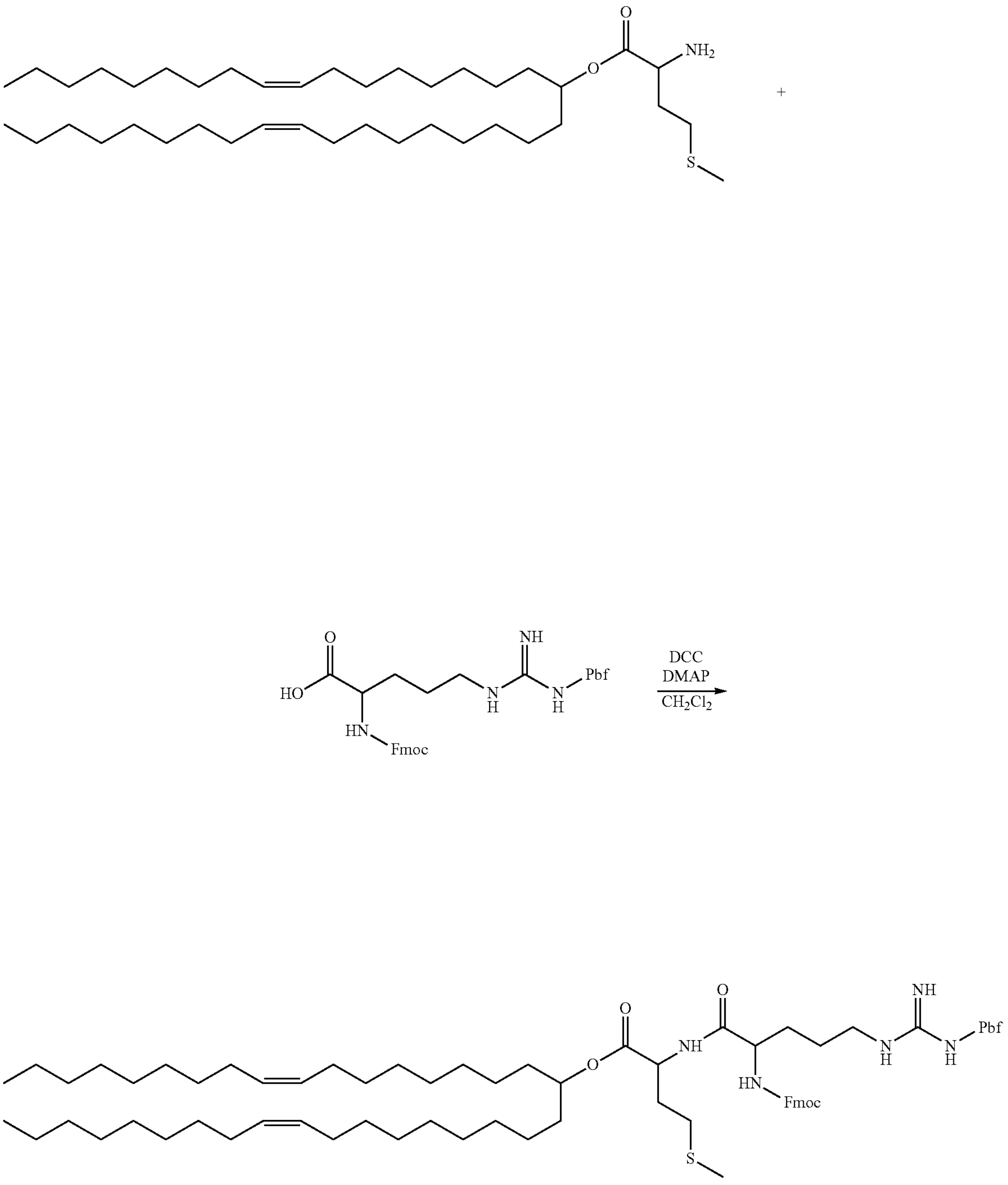

(9Z,27Z)-Hexatriaconta-9,27-dien-18-yl methioninate (1.9 g, 2.9 mmol) obtained in step (f7), Fmoc-Arg(Pbf)-OH (2.3 g, 3.5 mmol) in which to the amino group and the guanidino group of arginine, protective groups (Fmoc group and Pbf group, respectively) had been attached in advance, DCC (0.90 g, 4.4 mmol), and DMAP (36 mg, 0.29 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl N2-(((9H-fluoren-9-yl)methoxy)carbonyl)-Nw-(2,2,4,6,7-pentamethyl-2,3-dihydrobenzofuran-5-yl)arginylmethioninate (2.6 g, 2.1 mmol, 71%).

Step (f9): Synthesis of (9Z,27Z)-hexatriaconta-9,27-dien-18-yl Nw-(2,2,4,6,7-pentamethyl-2,3-dihydrobenzofuran-5-yl)arginylmethioninate

[Formula 52]

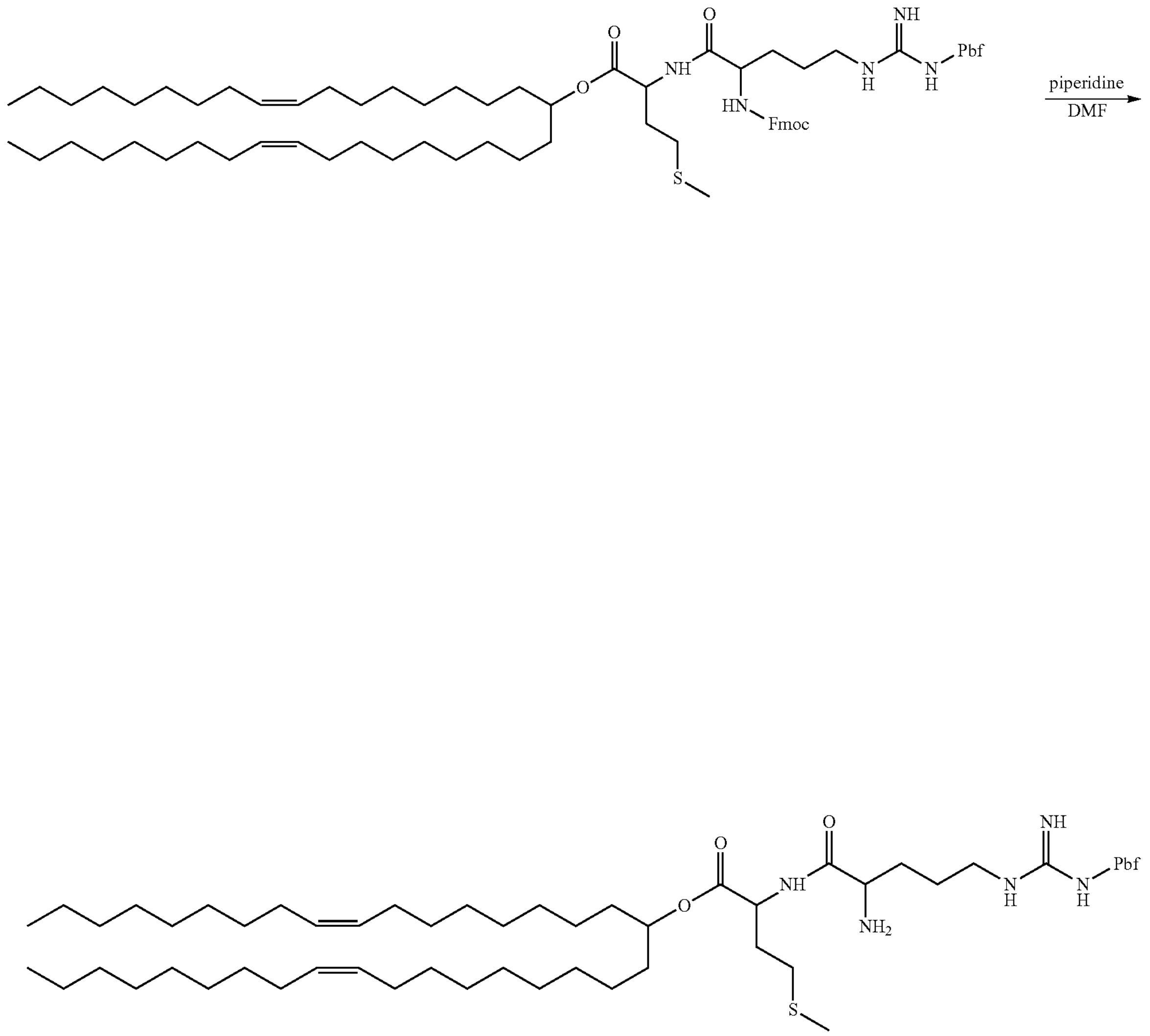

(9Z,27Z)-Hexatriaconta-9,27-dien-18-yl N2-(((9H-fluoren-9-yl)methoxy)carbonyl)-Nw-(2,2,4,6,7-pentamethyl-2,3-dihydrobenzofuran-5-yl)arginylmethioninate (2.6 g, 2.1 mmol) obtained in step (f8) was dissolved in a 20% piperidine/DMF solution (15 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl Nw-(2,2,4,6,7-pentamethyl-2,3-dihydrobenzofuran-5-yl)arginylmethioninate (1.3 g, 1.2 mmol, 58%).

Step (f10): Synthesis of (9Z,27Z)-hexatriaconta-9,27-dien-18-yl N-(2-amino-5-guanidino-1-iminopentyl)—S-ethylhomocysteinate (lipid (If))

[Formula 53]

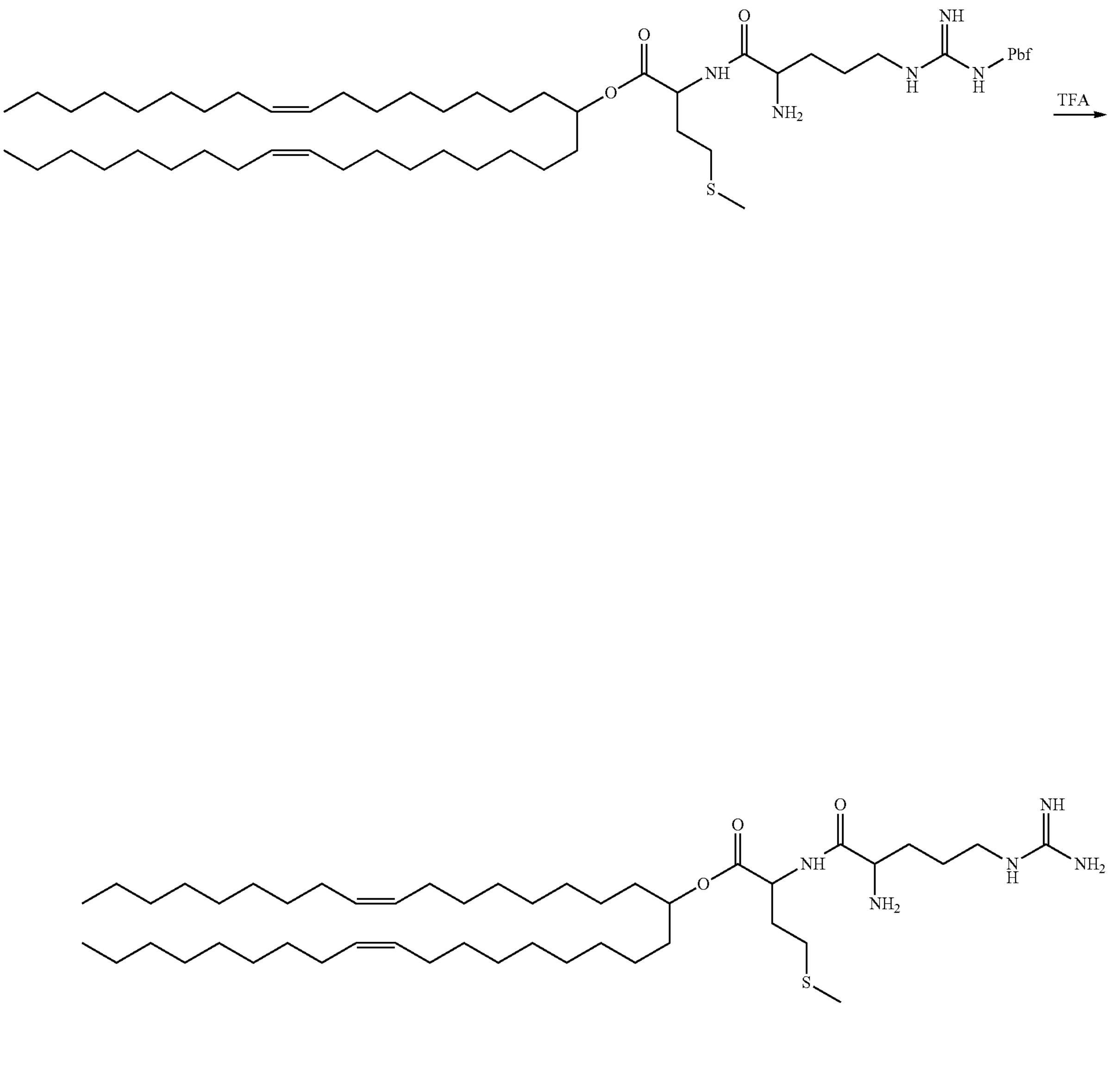

(9Z,27Z)-Hexatriaconta-9,27-dien-18-yl Nw-(2,2,4,6,7-pentamethyl-2,3-dihydrobenzofuran-5-yl)arginylmethioninate (1.3 g, 1.2 mmol) obtained in step (f9) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target (9Z,27Z)-hexatriaconta-9,27-dien-18-yl N-(2-amino-5-guanidino-1-iminopentyl)—S-ethylhomocysteinate (lipid (If)) (0.21 g, 0.26 mmol, 22%).

$^1$H-NMR (400 MHz, CHLOROFORM-D) δ 5.34 (d, 4H), 5.03 (s, 1H), 4.78 (d, 1H), 3.10-2.82 (m, 5H), 2.22-1.72 (m, 13H), 1.70-1.60 (2H), 1.60-1.36 (m, 6H), 1.24 (s, 46H), 0.99-0.76 (m, 6H)

$[C_{47}H_{91}N_5O_3SH]^+$: 806.73

Example 7

Synthesis of 3-(2,6-diaminohexanamido)-4-(((9Z,27Z)-hexatriaconta-9,27-dien-18-yl)oxy)-4-oxobutanoic acid (hereinafter also referred to as lipid (Ig))

Lipid (Ig) is a lipid in which the second amino acid of lipid (Ia) is changed to Lys. Hereinafter, a method for synthesizing lipid (Ig) will be described. The step of synthesizing a lipophilic region and the step of binding the lipophilic region and the first amino acid in the synthesis step is the same as the steps of step (a1) to step (a7) for lipid (Ia), and thus will be omitted.

Step (g8): Synthesis of 4-(tert-butyl) 1-((9Z,27Z)-hexatriaconta-9,27-dien-18-yl) N2-(((9H-fluoren-9-yl)methoxy)carbonyl)-N6-(tert-butoxycarbonyl)lysylaspartate

[Formula 54]

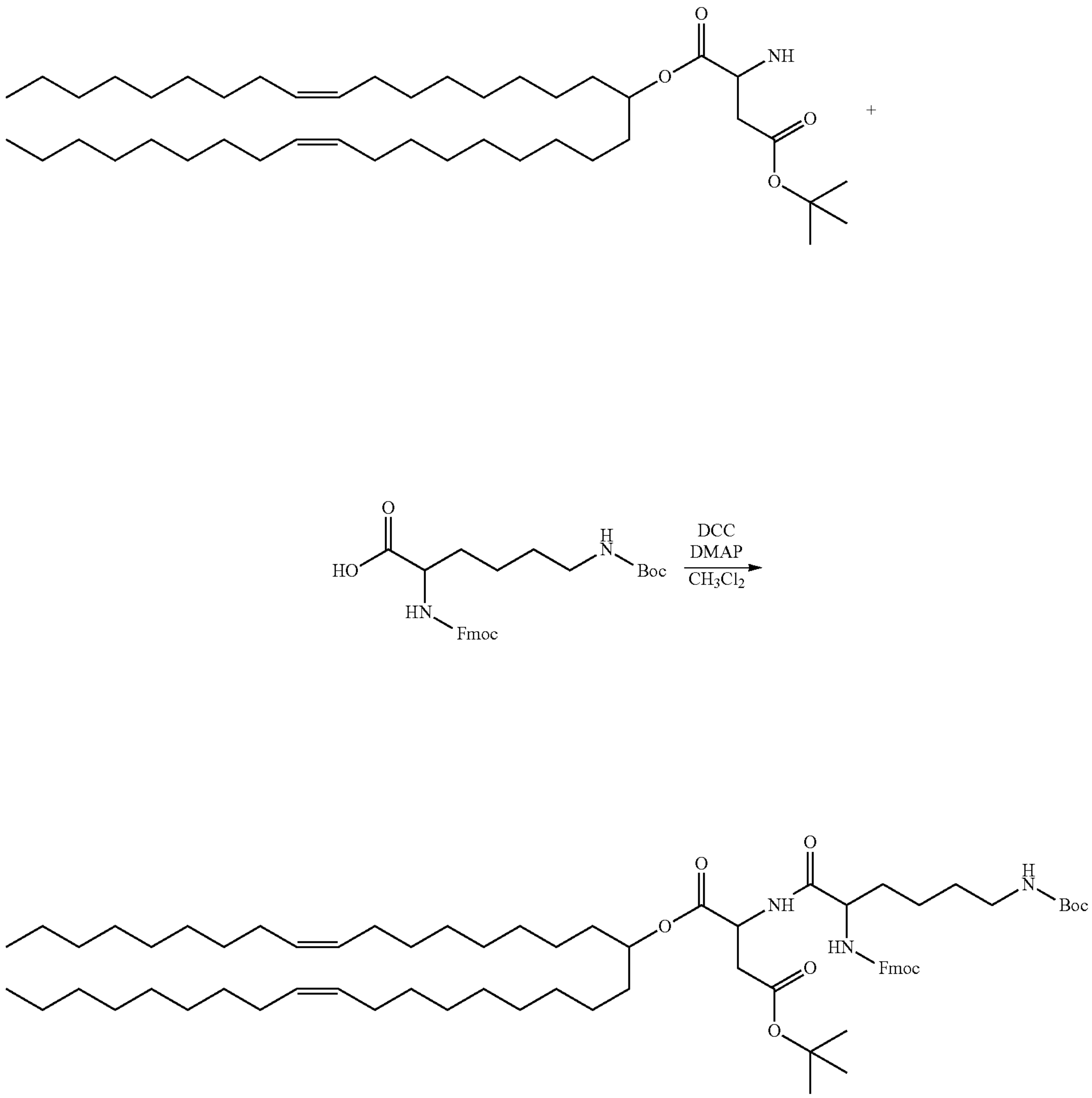

4-(tert-Butyl) 1-((9Z,27Z)-hexatriaconta-9,27-dien-18-yl) aspartic acid (1.5 g, 2.2 mmol) obtained in step (a7), Fmoc-Lys(Boc)-OH (1.2 g, 2.6 mmol) in which to the amino group and the guanidino group of lysine, protective groups (Fmoc group and Boc group, respectively) had been attached in advance, DCC (0.67 g, 3.3 mmol), and DMAP (27 mg, 0.22 mmol) were dissolved in dichloromethane (22 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) N2-(((9H-fluoren-9-yl)methoxy)carbonyl)-N6-(tert-butoxycarbonyl)lysylaspartate (1.7 g, 1.5 mmol, 68%).

Step (g9): Synthesis of 4-(tert-butyl) 1-((9Z,27Z)-hexatriaconta-9,27-dien-18-yl) N6-(tert-butoxycarbonyl)lysylaspartate

[Formula 55]

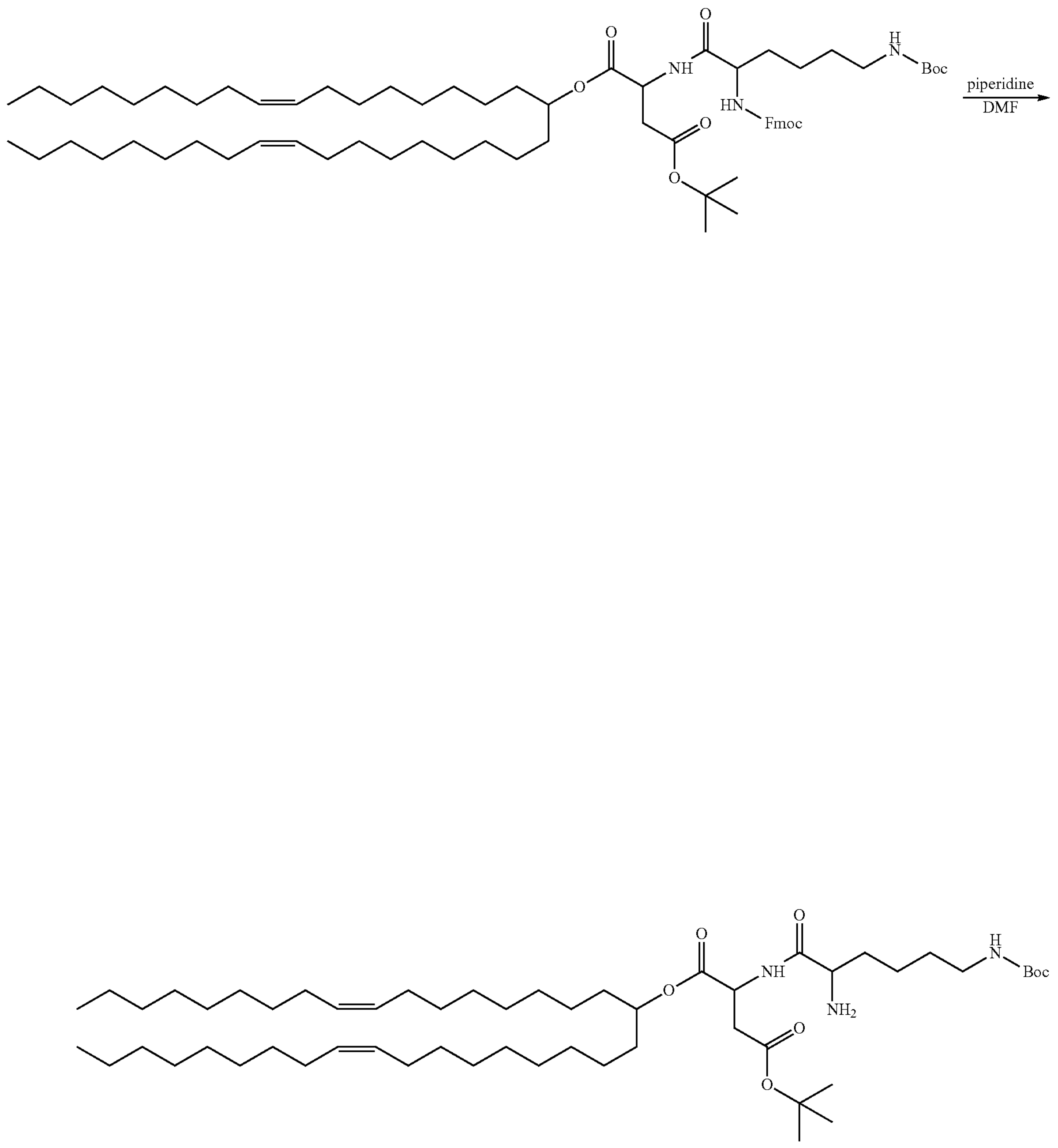

4-(tert-Butyl) 1-((9Z,27Z)-hexatriaconta-9,27-dien-18-yl) N2-(((9H-fluoren-9-yl)methoxy)carbonyl)-N6-(tert-butoxycarbonyl)lysylaspartic acid (1.7 g, 1.5 mmol) obtained in step (g8) was dissolved in a 20% piperidine/DMF solution (15 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) N6-(tert-butoxycarbonyl)lysylaspartate (0.88 g, 0.96 mmol, 65%).

Step (g10): Synthesis of 3-(2,6-Diaminohexanamido)-4-(((9Z,27Z)-Hexatriaconta-9,27-Dien-18-Yl)Oxy)-4-Oxobutanoic Acid

[Formula 56]

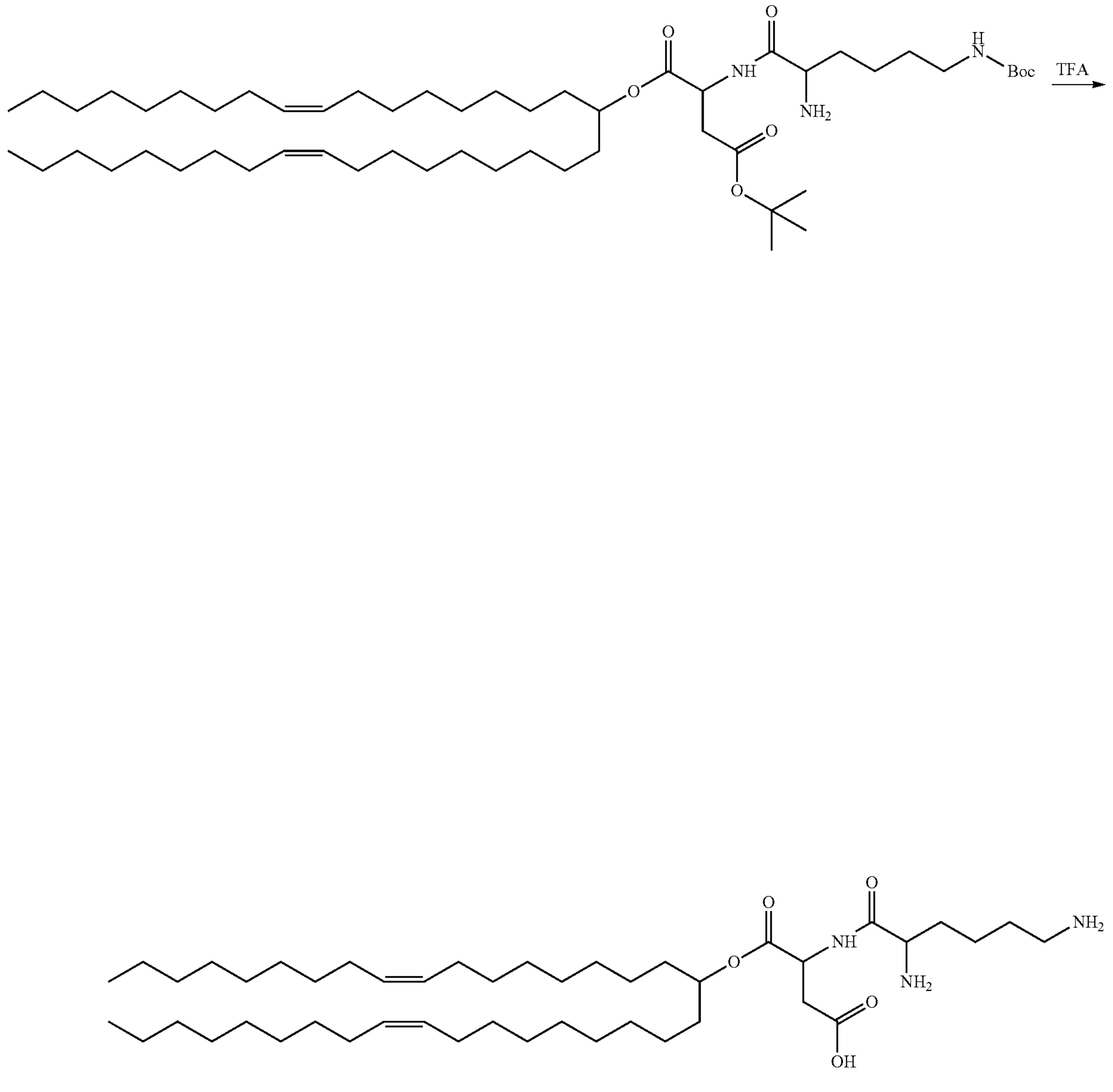

4-(tert-Butyl) 1-((9Z,27Z)-hexatriaconta-9,27-dien-18-yl) N6-(tert-butoxycarbonyl)lysylaspartate (0.88 g, 0.96 mmol) obtained in step (d9) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target 3-(2,6-diaminohexanamido)-4-(((9Z,27Z)-hexatriaconta-9,27-dien-18-yl)oxy)-4-oxobutanoic acid (lipid (Ig)) (0.26 g, 0.34 mmol, 35%).

$^1$H-NMR (400 MHz, CHLOROFORM-D) δ 5.32 (t, 4H), 4.90-4.62 (m, 1H), 4.14 (m, 1H) 3.02 (s, 2H), 2.95-2.60 (m, 1H), 2.12-1.81 (m, 8H), 1.72 (s, 2H), 1.65-1.42 (m, 6H), 1.35-0.98 (m, 48H), 0.86 (t, 6H)

$[C_{46}H_{87}N_3O_5H]^+$: 762.74

Example 8

Synthesis of 4-(2,6-diaminohexanamido)-5-(((9Z,27Z)-hexatriaconta-9,27-dien-18-yl)oxy)-5-oxopentanoic acid (hereinafter also referred to as lipid (Ih))

Lipid (Ih) is a lipid in which the first amino acid of lipid (Ia) is changed to Glu and the second amino acid is changed to Lys. Hereinafter, a method for synthesizing lipid (Ih) will be described. The step of synthesizing a lipophilic region and the step of binding the lipophilic region and the first amino acid in the synthesis step is the same as the steps of step (b1) to step (b7) for lipid (Ib), and thus will be omitted.

Step (h8): Synthesis of 5-(Tert-Butyl) 1-((9Z,27Z)-Hexatriaconta-9,27-Dien-18-Yl) N2-(((9H-Fluoren-9-Yl) Methoxy)Carbonyl)-N6-(Tert-Butoxycarbonyl)Lysylglutamate

[Formula 57]

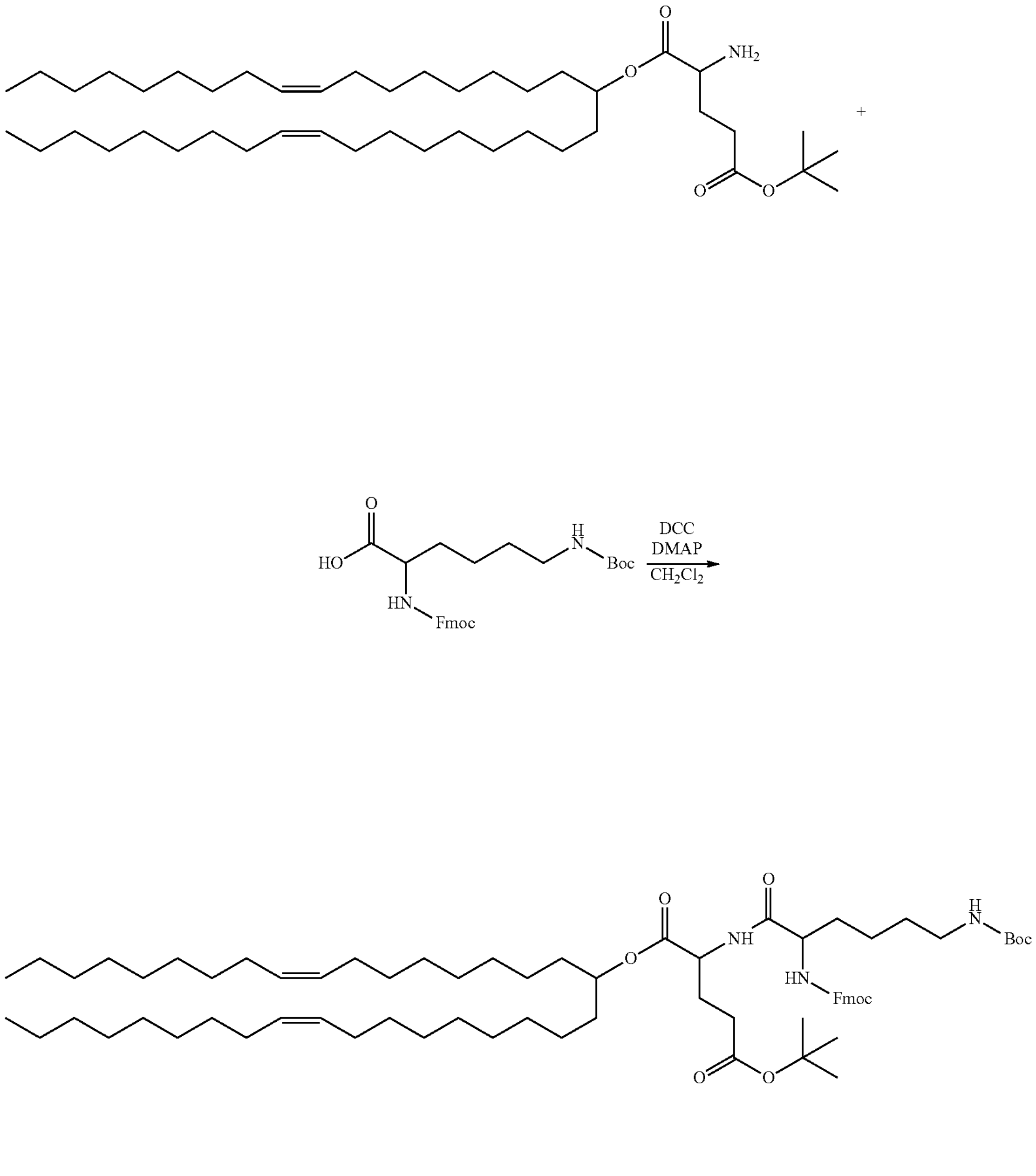

5-(tert-Butyl) 1-((9Z,27Z)-hexatriaconta-9,27-dien-18-yl) glutamic acid (1.5 g, 2.1 mmol) obtained in step (b7), Fmoc-Lys(Boc)-OH (1.2 g, 2.6 mmol) in which to the amino group and the guanidino group of lysine, protective groups (Fmoc group and Boc group, respectively) had been attached in advance, DCC (0.66 g, 3.2 mmol), and DMAP (26 mg, 0.21 mmol) were dissolved in dichloromethane (21 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) N2-(((9H-fluoren-9-yl)methoxy)carbonyl)-N6-(tert-butoxycarbonyl)lysylglutamate (1.7 g, 1.5 mmol, 70%).

Step (h9): Synthesis of 5-(tert-butyl) 1-((9Z,27Z)-hexatriaconta-9,27-dien-18-yl) N6-(tert-butoxycarbonyl)lysylglutamate

[Formula 58]

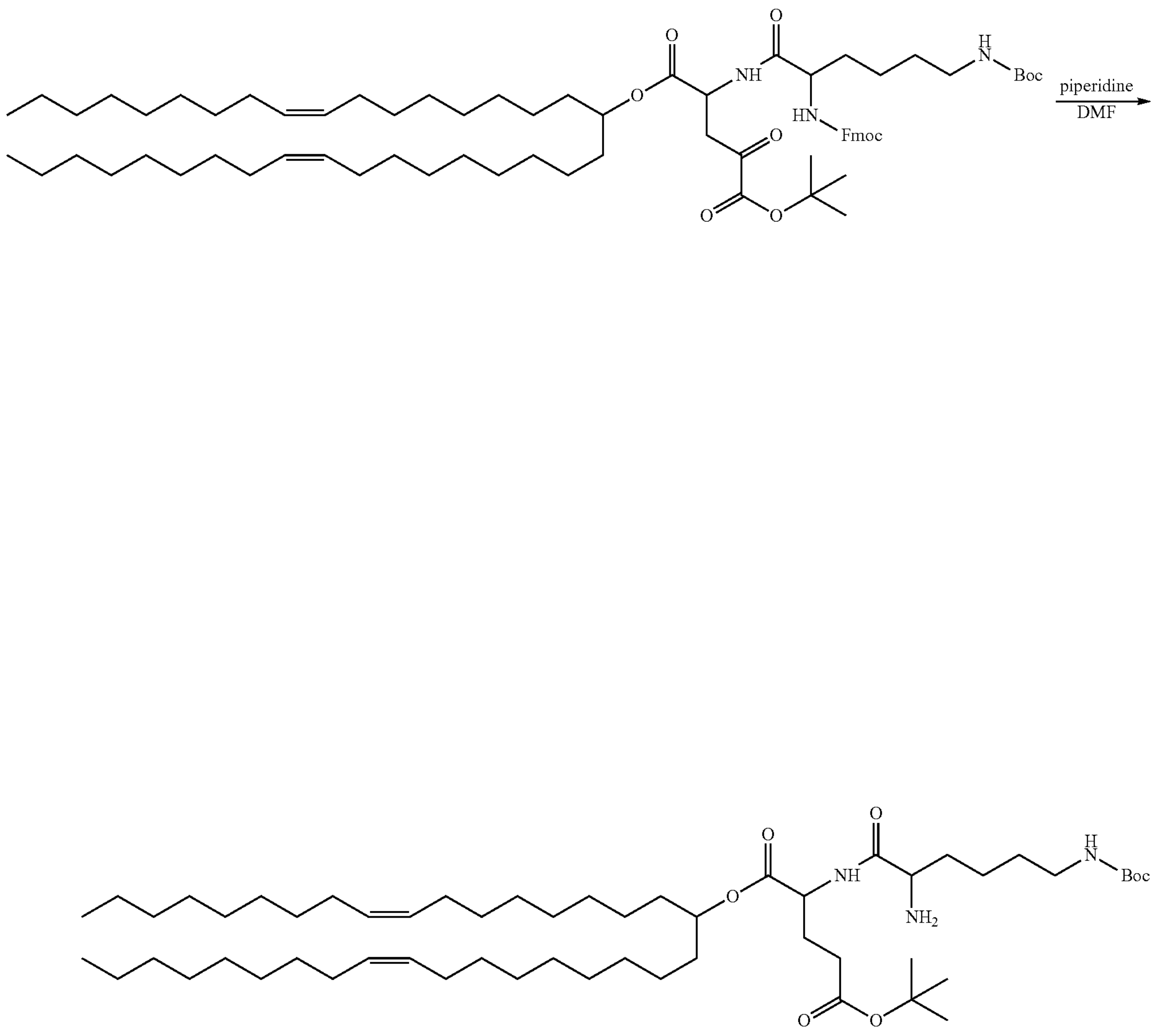

5-(tert-Butyl) 1-((9Z,27Z)-hexatriaconta-9,27-dien-18-yl) N2-(((9H-fluoren-9-yl)methoxy)carbonyl)-N6-(tert-butoxycarbonyl)lysylglutamate (1.7 g, 1.5 mmol) obtained in step (g8) was dissolved in a 20% piperidine/DMF solution (15 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) N6-(tert-butoxycarbonyl)lysylglutamate (1.1 g, 1.2 mmol, 78%).

Step (h10): Synthesis of 4-(2,6-diaminohexanamido)-5-(((9Z,27Z)-hexatriaconta-9,27-dien-18-yl)oxy)-5-oxopentanoic acid

[Formula 59]

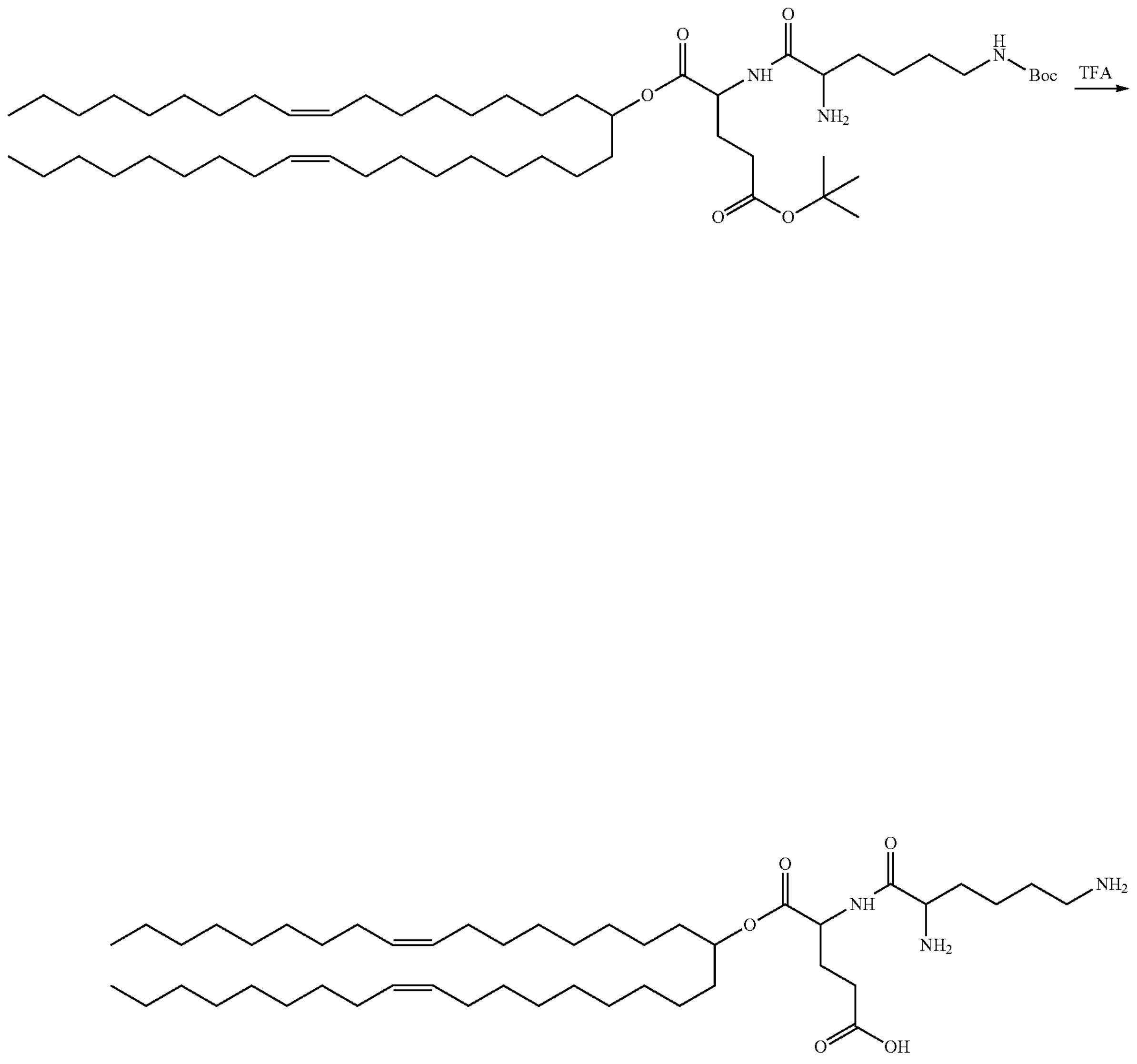

4-(tert-Butyl) 1-((9Z,27Z)-hexatriaconta-9,27-dien-18-yl) N6-(tert-butoxycarbonyl)lysylaspartate (1.1 g, 1.2 mmol) obtained in step (d9) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target 4-(2,6-diaminohexanamido)-5-(((9Z,27Z)-hexatriaconta-9,27-dien-18-yl)oxy)-5-oxopentanoic acid (lipid (Ih)) (0.23 g, 0.29 mmol, 25%).

$^1$H-NMR (400 MHz, CHLOROFORM-D) δ 7.94 (1H), 6.98 (1H), 5.39-5.25 (4H), 4.88-4.78 (1H), 4.60-4.31 (1H), 4.20-4.07 (1H), 3.51-3.43 (1H), 3.36-3.23 (2H), 3.14-2.91 (2H), 2.05-1.81 (8H), 1.82-1.70 (2H), 1.54-1.38 (6H), 1.37-1.13 (48H), 0.89-0.79 (6H)

$[C_{47}H_{89}N_3O_5H]^+$: 776.70

Example 9

Synthesis of 4-(2-amino-3-(1H-imidazol-4-yl)propanamido)-5-(((9Z,27Z)-hexatriaconta-9,27-dien-18-yl)oxy)-5-oxopentanoic acid (hereinafter also referred to as lipid (Ii))

Lipid (Ii) is a lipid in which the first amino acid of lipid (Ia) is changed to Glu and the second amino acid is changed to His. Hereinafter, a method for synthesizing lipid (Ii) will be described. The step of synthesizing a lipophilic region and the step of binding the lipophilic region and the first amino acid in the synthesis step is the same as the steps of step (b1) to step (b7) for lipid (Ib), and thus will be omitted.

Step (i8): Synthesis of 5-(tert-butyl) 1-((9Z,27Z)-hexatriaconta-9,27-dien-18-yl) Na-(((9H-fluoren-9-yl)methoxy)carbonyl) Nt-tritylhistidylglutamate

[Formula 60]

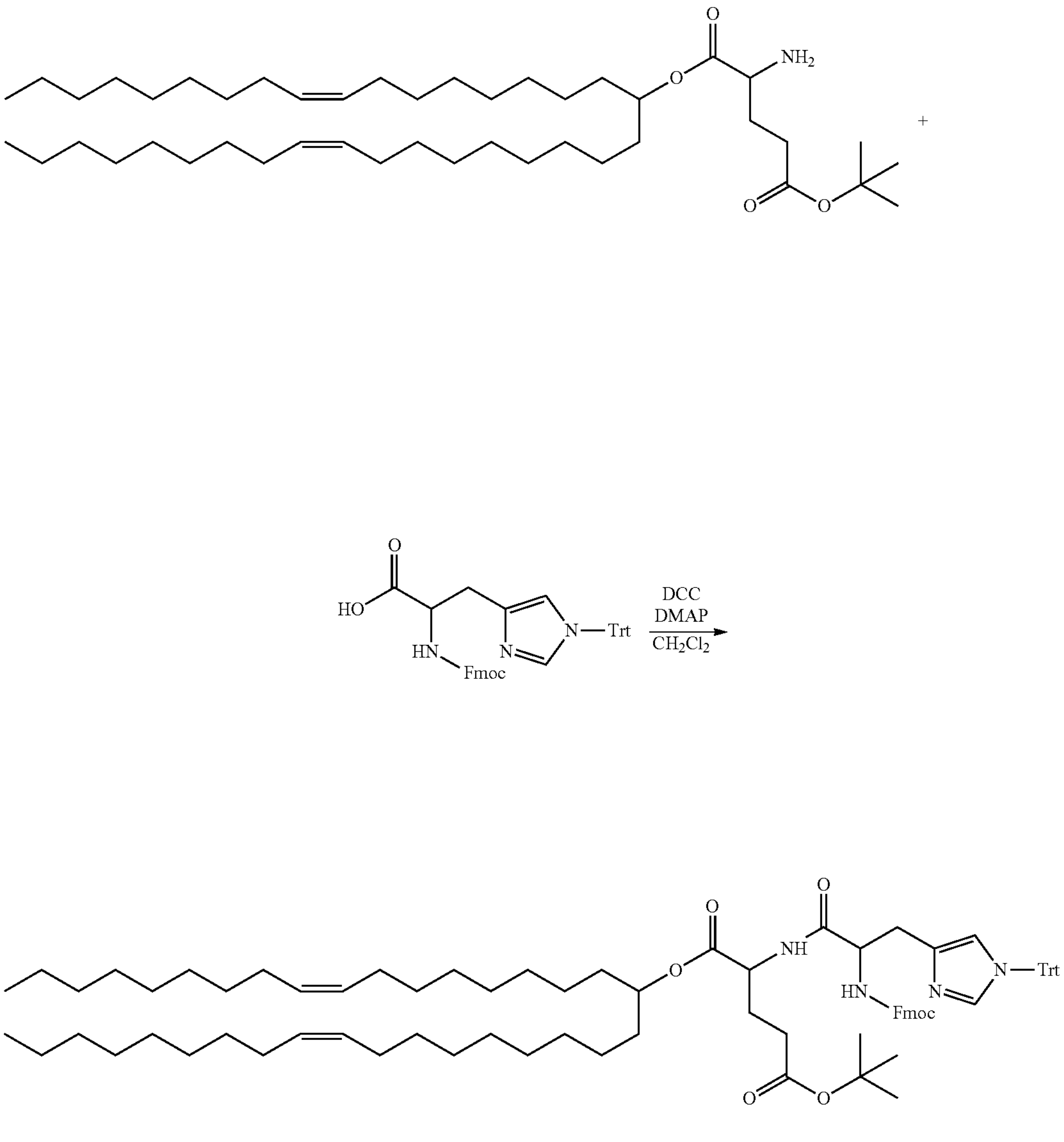

5-(tert-Butyl) 1-((9Z,27Z)-hexatriaconta-9,27-dien-18-yl) glutamate (1.5 g, 2.1 mmol) obtained in step (b7), Fmoc-His(Trt)-OH (1.6 g, 2.6 mmol) in which to the amino group of histidine, protective groups (Fmoc group and Trt group, respectively) had been attached in advance, DCC (0.66 g, 3.2 mmol), and DMAP (26 mg, 0.21 mmol) were dissolved in dichloromethane (21 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) Na-(((9H-fluoren-9-yl)methoxy)carbonyl) Nt-tritylhistidylglutamate (1.8 g, 1.4 mmol, 65%).

Step (i9): Synthesis of 5-(tert-butyl) 1-((9Z,27Z)-hexatriaconta-9,27-dien-18-yl) Nt-tritylhistidylglutamate

[Formula 61]

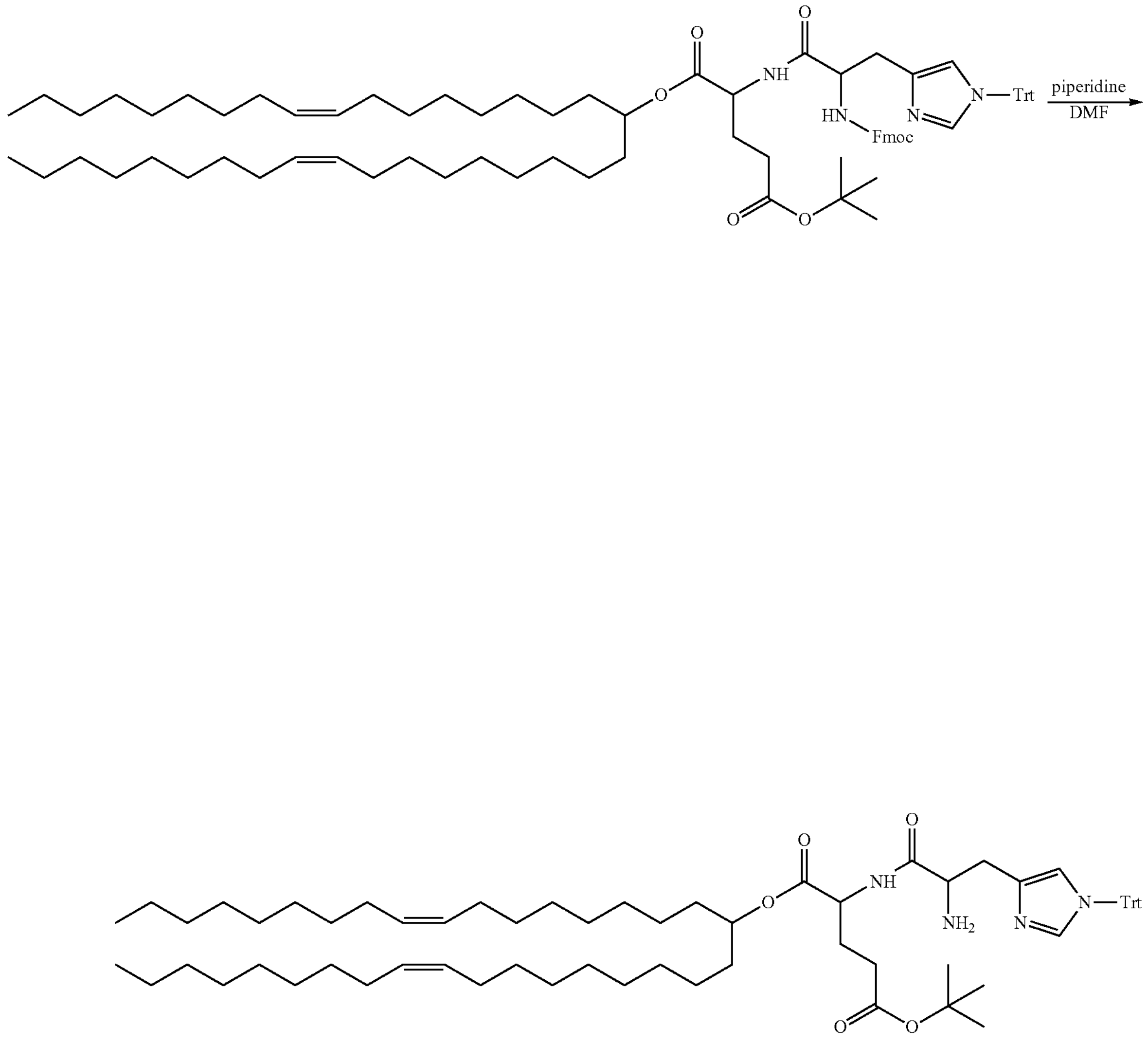

5-(tert-Butyl) 1-((9Z,27Z)-hexatriaconta-9,27-dien-18-yl) N2-(((9H-fluoren-9-yl)methoxy)carbonyl) Nt-tritylhistidylglutamate (1.8 g, 1.4 mmol) obtained in step (i8) was dissolved in a 20% piperidine/DMF solution (15 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) Nt-tritylhistidylglutamate (1.1 g, 1.0 mmol, 73%).

Step (i10): Synthesis of 4-(2-amino-3-(1H-imidazol-4-yl) propanamido)-5-(((9Z,27Z)-hexatriaconta-9,27-dien-18-yl) oxy)-5-oxopentanoic Acid

[Formula 62]

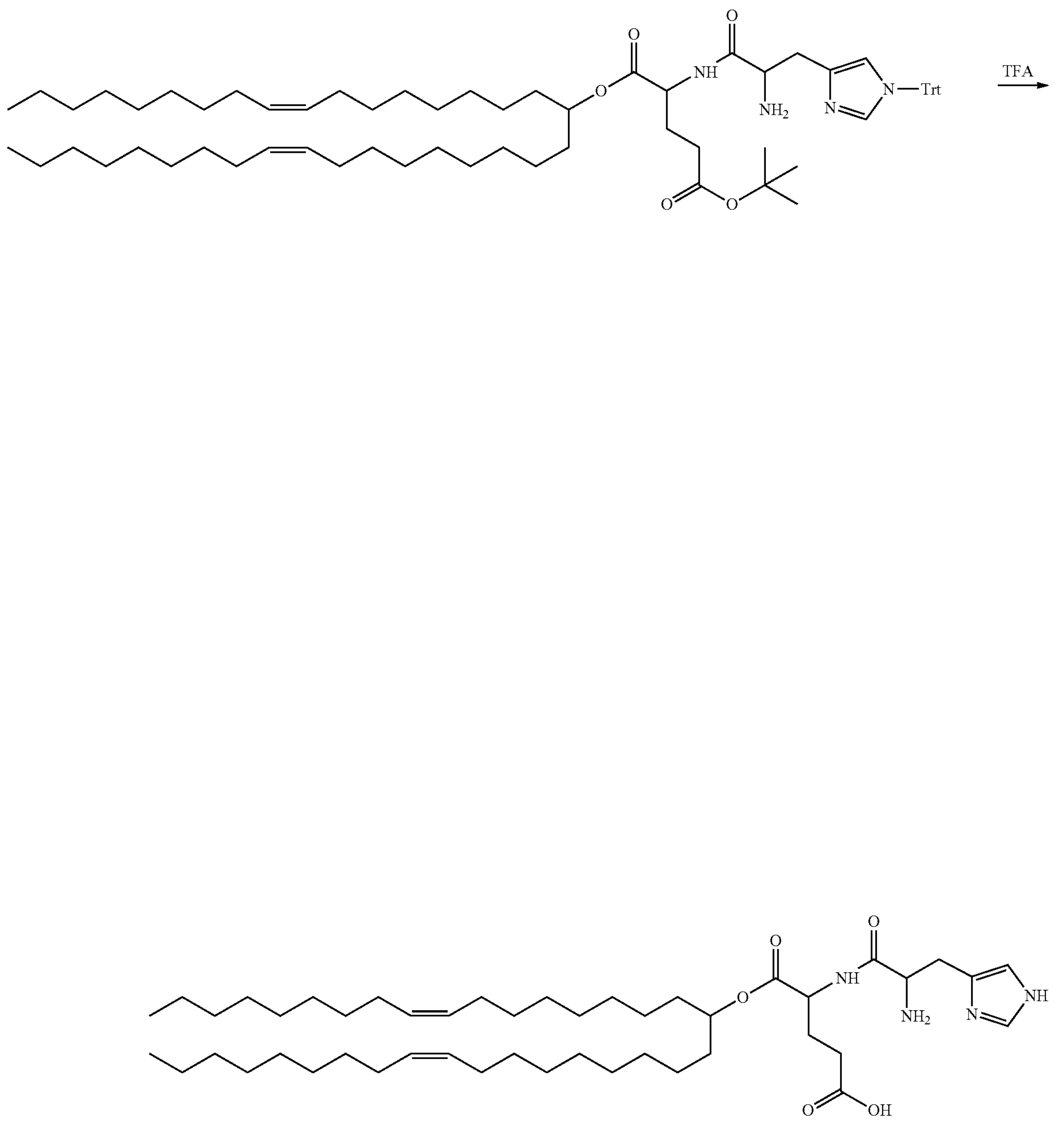

5-(tert-butyl) 1-((9Z,27Z)-hexatriaconta-9,27-dien-18-yl) Nt-tritylhistidylglutamate (1.1 g, 1.0 mmol) obtained in step (19) was dissolved in TFA (10 mL). The resulting solution was stirred at room temperature for 1 hour, and then the solvent was concentrated under reduced pressure. The resulting crude product was purified by silica gel column chromatography (ethyl acetate/methanol) to obtain the target 4-(2-amino-3-(1H-imidazol-4-yl) propanamido)-5-(((9Z,27Z)-hexatriaconta-9,27-dien-18-yl) oxy)-5-oxopentanoic acid (lipid (Ii)) (0.14 g, 0.18 mmol, 18%).

$^1$H-NMR (400 MHz, CHLOROFORM-D) δ 5.34 (d, J=15.1 Hz, 4H), 4.86 (s, 1H), 3.83-3.47 (m, 1H), 3.35-2.83 (m, 3H), 2.29 (s, 2H), 2.03 (d, J=34.8 Hz, 10H), 1.66-1.36 (m, 6H), 1.24 (s, 46H), 0.96-0.74 (m, 6H)

$[C_{47}H_{84}N_4O_5H]^+$: 785.65

Example 10

Synthesis of (6Z,9Z,27Z,30Z)-hexatriaconta-6,9,27,30-tetraen-18-yl 2-(2-amino-5-guanidinopentanamido)-3-hydroxybutanoate (hereinafter also referred to as lipid (Ij))

Lipid (Ij) is a lipid in which the number of unsaturated bonds in the hydrocarbon group of the lipophilic region of lipid (Ie) is changed.

[Formula 63]

(Ij)

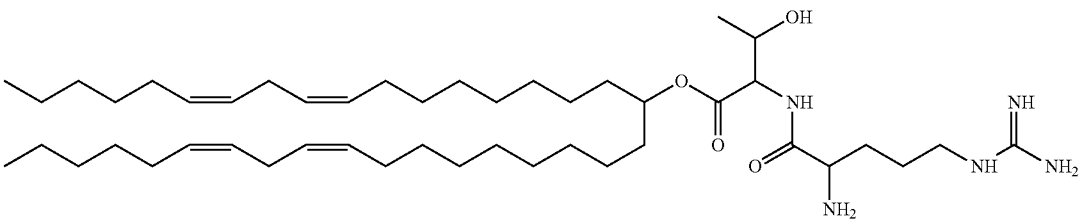

The step of synthesizing a lipophilic region in the synthesis step was carried out by the same procedure as for the steps of step (a1) to step (a5) for lipid (Ia). In addition, the step of binding the first amino acid and the second amino acid to the lipophilic region was carried out by the same procedure as for the step of binding the first amino acid and the second amino acid to the lipophilic region (step (e6) to step (e8)) in the lipid (Ie) synthesis step to obtain (6Z,9Z,27Z,30Z)-hexatriaconta-6,9,27,30-tetraen-18-yl 2-(2-amino-5-guanidinopentanamido)-3-hydroxybutanoate (lipid (Ij)).

$^1$H-NMR (400 MHz, CHLOROFORM-D) δ 5.43-5.18 (8H), 4.88-4.76 (1H), 4.46-4.36 (1H), 4.34-4.18 (2H), 3.30-2.94 (2H), 2.78-2.72 (4H), 2.10-1.82 (10H), 1.81-1.42 (6H), 1.40-0.97 (37H), 0.93-0.69 (6H)

$[C_{46}H_{85}N_5O_4H]^+$: 772.70

Example 11

Synthesis of 4-(2-amino-5-guanidinopentanamido)-5-oxo-5-(((9Z,30Z)-tetraconta-9,30-dien-18-yl)oxy)pentanoic acid (hereinafter also referred to as lipid (Ik))

Lipid (Ik) is a lipid in which the number of carbon atoms in the hydrocarbon group of the lipophilic region of lipid (Ib) is changed.

[Formula 64]

(Ik)

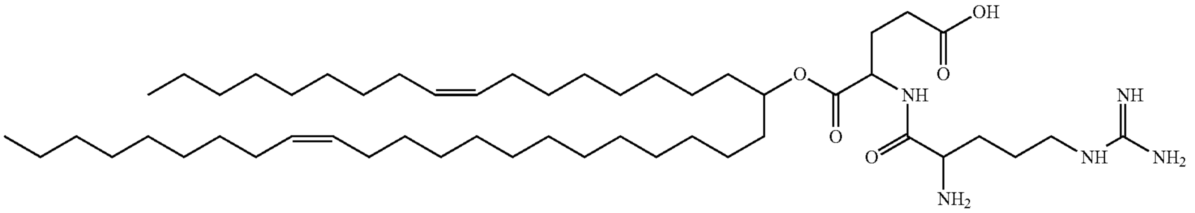

The step of synthesizing a lipophilic region in the synthesis step was carried out by the same procedure as for the steps of step (a1) to step (a5) for lipid (Ia). In addition, the step of binding the first amino acid and the second amino acid to the lipophilic region was carried out by the same procedure as for the step of binding the first amino acid and the second amino acid to the lipophilic region (step (b6) to step (b10)) in the lipid (Ib) synthesis step to obtain 4-(2-amino-5-guanidinopentanamido)-5-oxo-5-(((9Z,30Z)-tetraconta-9,30-dien-18-yl)oxy)pentanoic acid (lipid (Ik)).

$^1$H-NMR (400 MHz, CHLOROFORM-D) δ 5.47-5.18 (4H), 4.88-4.76 (1H), 4.46-4.36 (1H), 4.34-4.18 (1H), 4.16-3.92 (1H), 3.46-2.85 (2H), 2.56-2.10 (3H), 2.09-1.95 (10H), 1.77-1.57 (2H), 1.57-1.42 (4H), 1.41-1.06 (54H), 0.93-0.78 (6H)

$[C_{51}H_{97}N_5O_5H]^+$: 860.74

Example 12

Synthesis of 4-(2-amino-5-guanidinopentanamido)-5-oxo-5-(((10Z,34Z)-tetratetraconta-10,34-dien-22-yl)oxy)pentanoic acid (hereinafter also referred to as lipid (Il))

Lipid (Il) is a lipid in which the number of carbon atoms in the hydrocarbon group of the lipophilic region of lipid (Ib) is changed.

[Formula 65]

(Il)

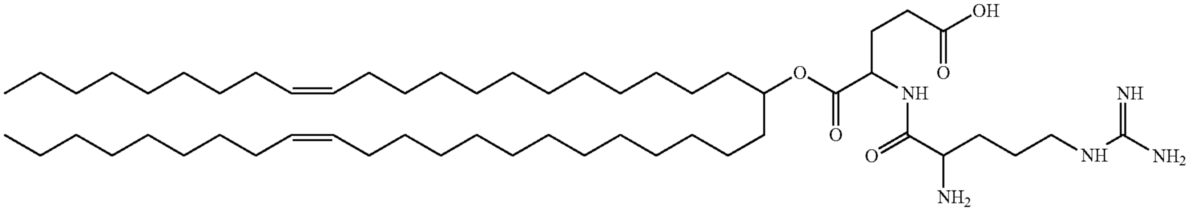

The step of synthesizing a lipophilic region in the synthesis step was carried out by the same procedure as for the steps of step (a1) to step (a5) for lipid (Ia). In addition, the step of binding the first amino acid and the second amino acid to the lipophilic region was carried out by the same procedure as for the step of binding the first amino acid and the second amino acid to the lipophilic region (step (b6) to step (b10)) in the lipid (Ib) synthesis step to obtain 4-(2-amino-5-guanidinopentanamido)-5-oxo-5-(((10Z,34Z)-tetratetraconta-10,34-dien-22-yl)oxy)pentanoic acid (lipid (II)).

$^1$H-NMR (400 MHz, CHLOROFORM-D) δ 5.46-5.18 (4H), 4.95-4.70 (1H), 4.70-4.41 (1H), 4.26-3.81 (1H), 3.40-2.66 (2H), 2.65-2.11 (2H), 2.08-1.81 (10H), 1.81-1.43 (8H), 1.42-0.98 (62H), 0.98-0.78 (7H)

$[C_{55}H_{105}N_5O_5H]^+$: 916.92

Comparative Example 1

Synthesis of (9Z,27Z)-hexatriaconta-9,27-dien-18-yl 2-amino-3-hydroxybutanoate (hereinafter also referred to as lipid (CEa))

[Formula 66]

(CEa)

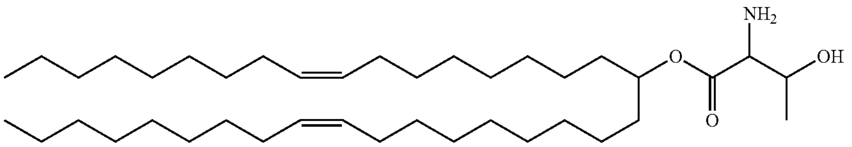

Lipid (CEa) has a lipophilic region that is a hydrocarbon group having 36 carbon atoms and a hydrophilic region that is Thr (first amino acid).

The step of synthesizing a lipophilic region in the method for synthesizing lipid (CEa) is the same as the steps of step (a1) to step (a5) for lipid (Ia). In addition, the step of binding the first amino acid to the lipophilic region was carried out by the same procedure as for the steps of step (e6), step (e7), and step (e9) for lipid (Ie).

$^1$H-NMR (400 MHz, CHLOROFORM-D) δ 5.44-5.25 (m, 4H), 5.12-4.89 (m, 1H), 3.86 (d, J=4.6 Hz, 2H), 1.98 (q, J=6.7 Hz, 8H), 1.72-1.33 (m, 4H), 1.42-1.06 (m, 49H), 0.97-0.76 (m, 6H)

Comparative Example 2

Synthesis of 3-guanidino-4-(((9Z,27Z)-hexatriaconta-9,27-dien-18-yl)oxy)-4-oxobutanoic acid (hereinafter also referred to as lipid (CEb))

[Formula 67]

(CEb)

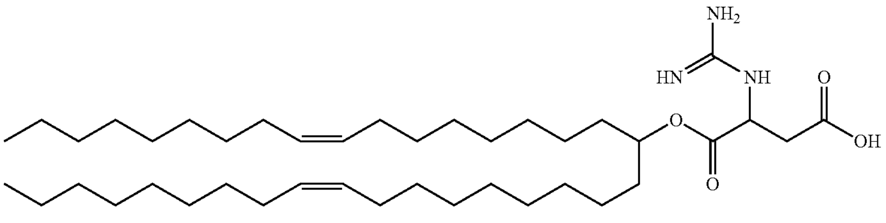

Lipid (CEb) is a lipid in which the first amino acid of lipid (CEa) is changed to a compound having a guanidino group. Hereinafter, a method for synthesizing lipid (CEb) will be described. The step of synthesizing a lipophilic region and some subsequent steps in the synthesis step are the same as the steps of step (a1) to step (a7) for lipid (Ia), and thus will be omitted.

Step: Synthesis of 4-(tert-butyl) 1-((9Z,27Z)-hexatriaconta-9,27-dien-18-yl) ((E)-N,N'-bis(tert-butoxycarbonyl)carbamimidoyl)aspartate

[Formula 68]

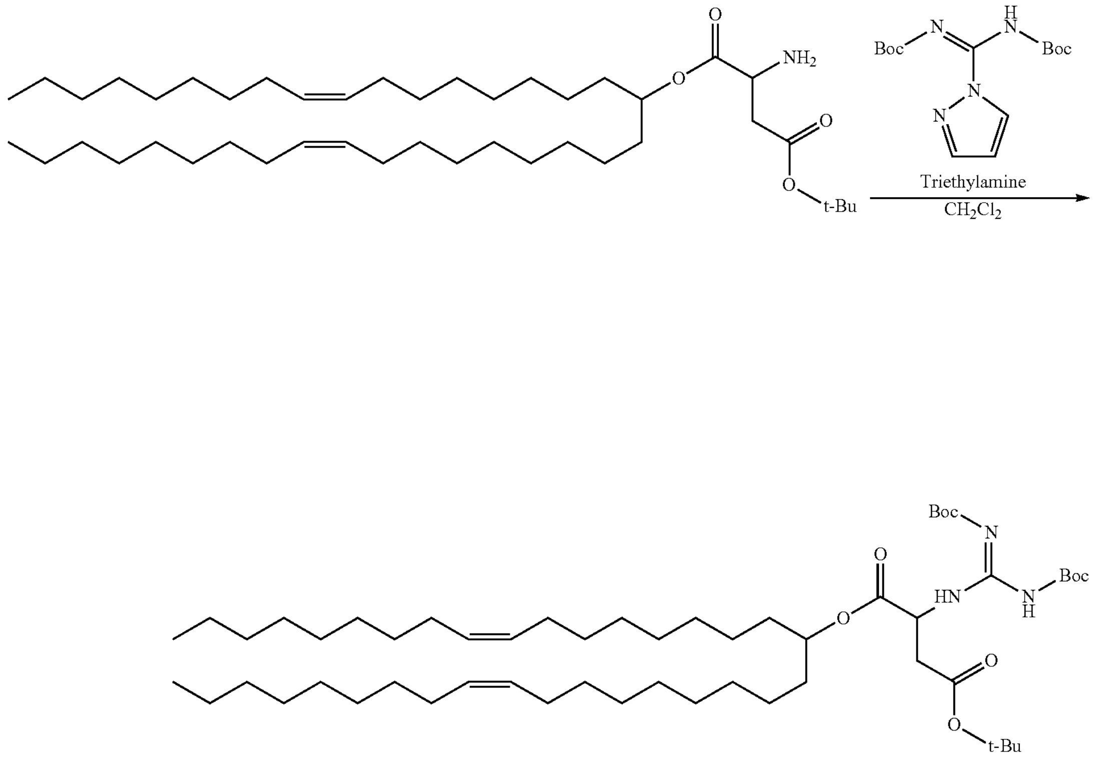

4-(tert-Butyl) 1-((9Z,27Z)-hexatriaconta-9,27-dien-18-yl) aspartate (1.5 g, 2.2 mmol), N,N'-di-BOC-1H-pyrazole-1-carboxamidine (0.74 g, 2.4 mmol), and triethylamine (0.26 g, 2.6 mmol) were dissolved in dichloromethane (5 mL). The resulting solution was stirred at room temperature until the next day, and then quenched with water. The residue obtained by concentrating the organic phase was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 4-(tert-butyl) 1-((9Z,27Z)-hexatriaconta-9,27-dien-18-yl) ((E)-N,N'-bis(tert-butoxycarbonyl)carbamimidoyl)aspartate (1.88 g, 2.0 mmol, 93%).

Step: Synthesis of 3-guanidino-4-(((9Z,27Z)-hexatriaconta-9,27-dien-18-yl)oxy)-4-oxobutanoic acid (lipid (CEb))

[Formula 69]

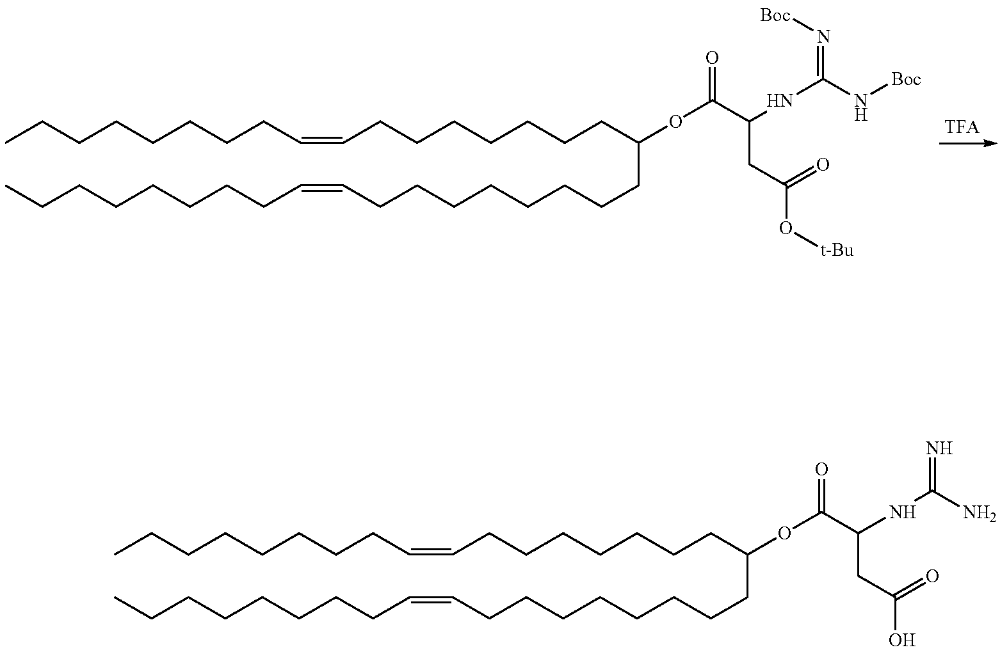

4-(tert-Butyl) 1-((9Z,27Z)-hexatriaconta-9,27-dien-18-yl) ((E)-N,N'-bis(tert-butoxycarbonyl)carbamimidoyl)aspartate (1.88 g, 2.0 mmol) was dissolved in trifluoroacetic acid (hereinafter also referred to as TFA) (5 mL). The resulting solution was stirred at room temperature for 1 hour, and then the solvent was concentrated under reduced pressure. The resulting crude product was purified by silica gel column chromatography (ethyl acetate/methanol) to obtain the target lipid (CEb) (0.66 g, 0.98 mmol, 61%).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.09-1.86 (m, 8H), 1.78-1.52 (m, 4H), 1.38-1.18 (m, 46H), 0.87 (t, J=6.9 Hz, 6H)

Comparative Example 3

Synthesis of 4-guanidino-5-(((9Z,27Z)-hexatriaconta-9,27-dien-18-yl)oxy)-5-oxopentanoic acid (hereinafter also referred to as lipid (CEc))

[Formula 70]

(CEc)

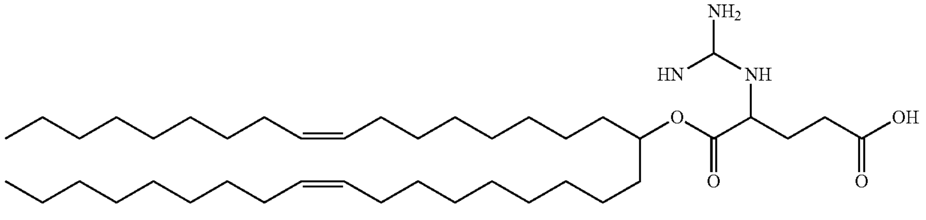

Lipid (CEc) is a lipid in which the first amino acid of lipid (CEa) is changed to a compound having a guanidino group. Hereinafter, a method for synthesizing lipid (CEc) will be described. The step of synthesizing a lipophilic region and some subsequent steps in the synthesis step are the same as the steps of step (a1) to step (a5) for lipid (Ia) and steps (b6) and (b7), and thus will be omitted.

Step: Synthesis of 5-(tert-butyl) 1-((9Z,27Z)-hexatriaconta-9,27-dien-18-yl) ((Z)—N,N'-bis(tert-butoxycarbonyl)carbamimidoyl)glutamate

[Formula 71]

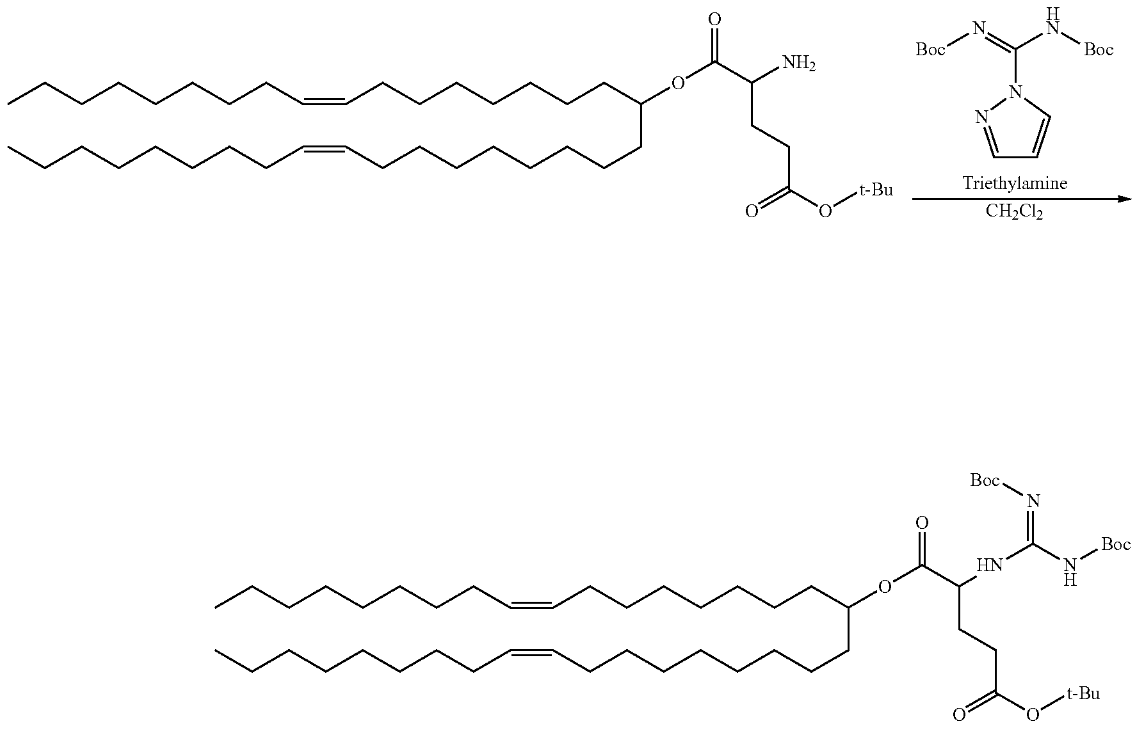

5-(tert-butyl) 1-((9Z,27Z)-hexatriaconta-9,27-dien-18-yl) glutamate (1.0 g, 1.4 mmol), N,N'-di-BOC-1H-pyrazole-1-carboxamidine (0.48 g, 1.6 mmol), and triethylamine (0.17 g, 1.7 mmol) were dissolved in dichloromethane (5 mL). The resulting solution was stirred at room temperature until the next day, and then quenched with water. The residue obtained by concentrating the organic phase was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 5-(tert-butyl) 1-((9Z,27Z)-hexatriaconta-9,27-dien-18-yl) ((Z)—N,N'-bis (tert-butoxycarbonyl)carbamimidoyl)glutamate (1.34 g, 1.4 mmol, 100%).

Step: Synthesis of 4-guanidino-5-(((9Z,27Z)-hexatriaconta-9,27-dien-18-yl)oxy)-5-oxopentanoic acid (lipid (CEc))

[Formula 72]

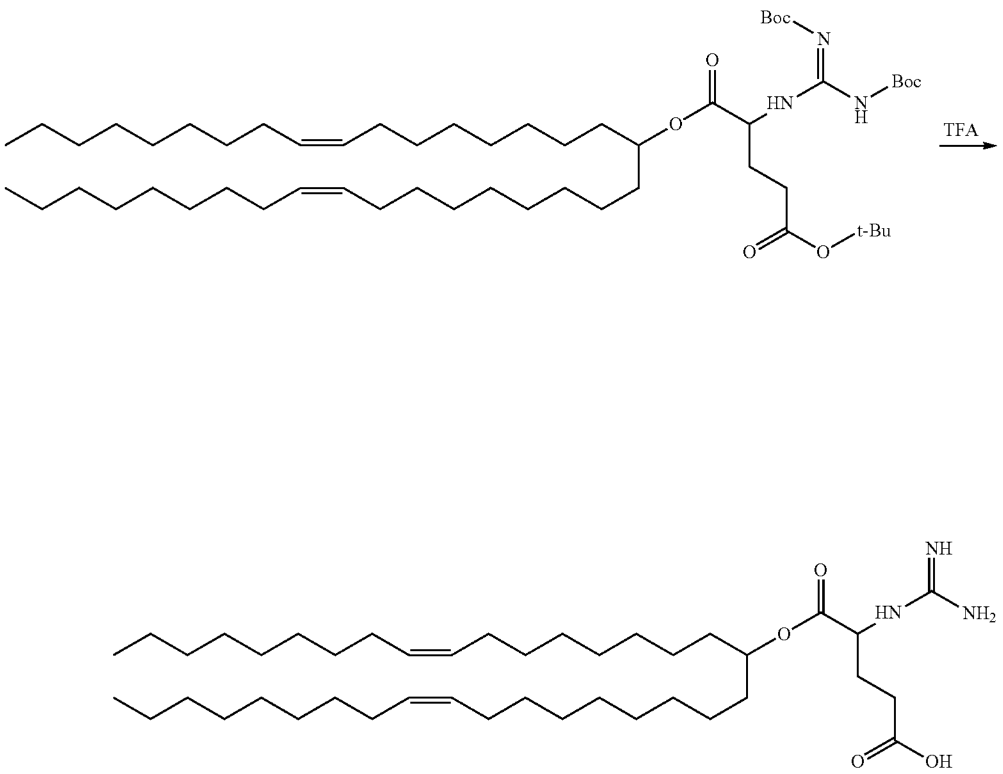

5-(tert-Butyl) 1-((9Z,27Z)-hexatriaconta-9,27-dien-18-yl) ((Z)—N,N'-bis(tert-butoxycarbonyl)carbamimidoyl)glutamate (1.34 g, 1.4 mmol) was dissolved in trifluoroacetic acid (hereinafter also referred to as TFA) (5 mL). The resulting solution was stirred at room temperature for 1 hour, and then the solvent was concentrated under reduced pressure. The resulting crude product was purified by silica gel column chromatography (ethyl acetate/methanol) to obtain the target lipid (CEc) (0.45 g, 0.67 mmol, 44%).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (m, 2H), 2.09-1.86 (m, 10H), 1.78-1.52 (m, 4H), 1.38-1.18 (m, 46H), 0.87 (t, J=6.9 Hz, 6H)

Comparative Example 4

Synthesis of (9Z,27Z)-hexatriaconta-9,27-dien-18-yl lysinate (hereinafter also referred to as lipid (CEd))

[Formula 73]

(CEd)

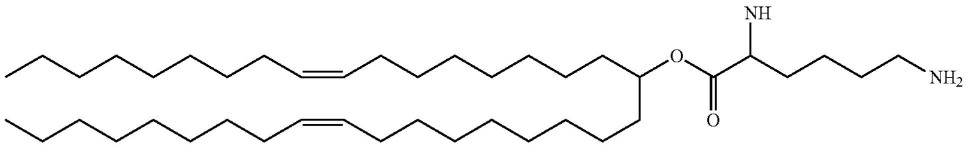

Lipid (CEd) is a lipid in which the first amino acid of lipid (CEa) is changed to Lys. Hereinafter, a method for synthesizing lipid (CEd) will be described. The step of synthesizing a lipophilic region in the synthesis step is the same as the steps of step (a1) to step (a5) for lipid (Ia), and thus will be omitted.

Step (CEd1): Synthesis of (9Z,27Z)-hexatriaconta-9,27-dien-18-yl N2, N6-bis(((9H-fluoren-9-yl)methoxy)carbonyl)lysinate

[Formula 74]

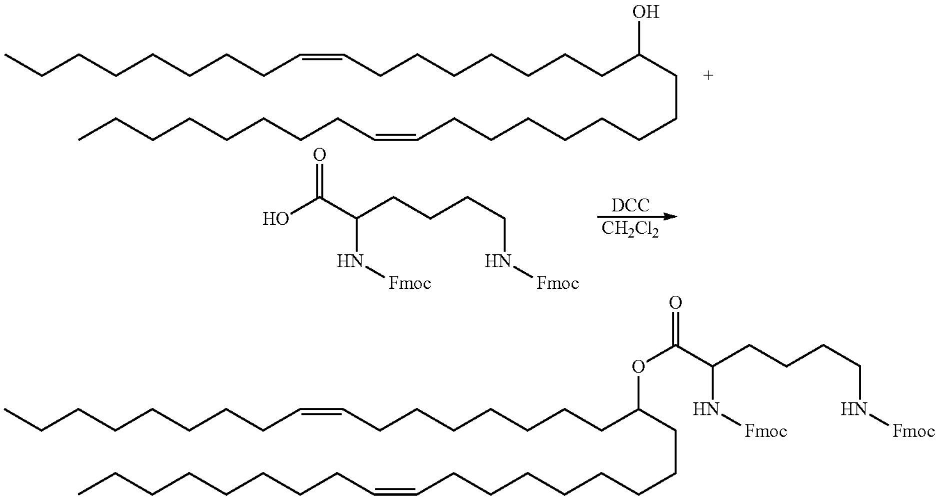

(9Z,27Z)-Hexatriaconta-9,27-dien-18-ol (2.0 g, 3.9 mmol) obtained in step (a5), $N^{\alpha}$,$N^{\varepsilon}$-bis[(9H-fluoren-9-yl-methoxy)carbonyl]-L-lysine (Fmoc-Lys(Fmoc)-OH) (4.55 g, 7.7 mmol), and DCC (2.0 g, 7.7 mmol) were dissolved in dichloromethane (15 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target (9Z,27Z)-hexatriaconta-9,27-dien-18-yl N2,N6-bis(((9H-fluoren-9-yl)methoxy)carbonyl)lysinate (3.8 g, 3.5 mmol, 90%).

Step (CEd2): Synthesis of (9Z,27Z)-hexatriaconta-9,27-dien-18-yl lysinate

[Formula 75]

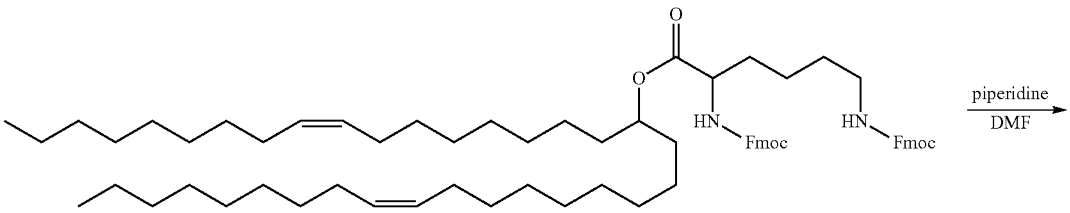

-continued

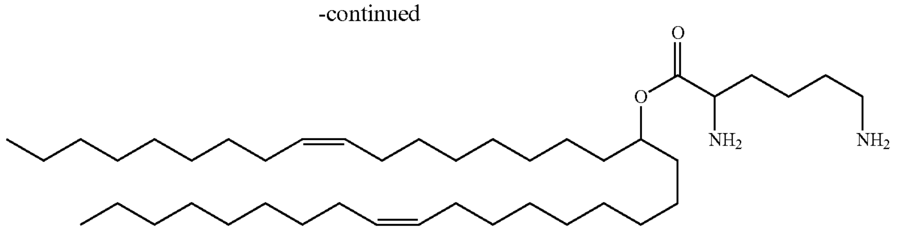

(9Z,27Z)-Hexatriaconta-9,27-dien-18-yl N2,N6-bis(((9H-fluoren-9-yl)methoxy)carbonyl)lysinate (3.5 g, 3.5 mmol) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target lipid (CEd) (1.5 g, 2.3 mmol, 72%).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.09-1.86 (m, 10H), 1.78-1.52 (m, 4H), 1.38-1.18 (m, 50H), 0.87 (t, J=6.9 Hz, 6H)

Comparative Example 5

Synthesis of (6Z,14Z)-icosa-6,14-dien-10-yl lysinate (hereinafter also referred to as lipid (CEe))

[Formula 76]

(CEe)

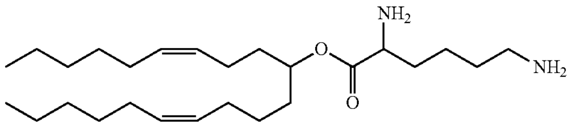

Lipid (CEe) is a lipid in which the number of carbon atoms in the hydrocarbon group of the lipophilic region of lipid (CEd) is changed. In the method for synthesizing lipid (CEe), the step of synthesizing a lipophilic region in the synthesis step was carried out by the same procedure as for the steps of step (a1) to step (a5) for lipid (Ia). In addition, the step of attaching the first amino acid to the lipophilic region was carried out in the same manner as for step (CEd1) and step (CEd2) for lipid (CEd) to obtain lipid (CEe).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.09-1.86 (m, 24H), 1.38-1.18 (m, 8H), 0.87 (t, J=6.9 Hz, 6H)

Comparative Example 6

Synthesis of (7Z,25Z)-dotriaconta-7,25-dien-16-yl lysinate (hereinafter also referred to as lipid (CEf))

[Formula 77]

(CEf)

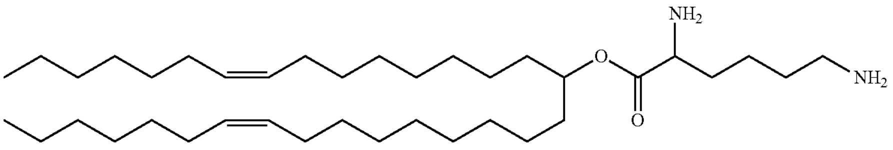

Lipid (CEf) is a lipid in which the number of carbon atoms in the hydrocarbon group of the lipophilic region of lipid (CEd) is changed. In the method for synthesizing lipid (CEf), the step of synthesizing a lipophilic region in the synthesis step was carried out by the same procedure as for the steps of step (a1) to step (a5) for lipid (Ia). In addition, the step of attaching the first amino acid to the lipophilic region was carried out in the same manner as for step (CEd1) and step (CEd2) for lipid (CEd) to obtain lipid (CEf).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.09-1.86 (m, 8H), 1.54-1.66 (4H,), 1.38-1.18 (m, 42H), 0.87 (t, J=6.9 Hz, 6H)

Comparative Example 7

Synthesis of (9Z,35Z)-tetratetraconta-9,35-dien-22-yl lysinate (hereinafter also referred to as lipid (CEg))

[Formula 78]

(CEg)

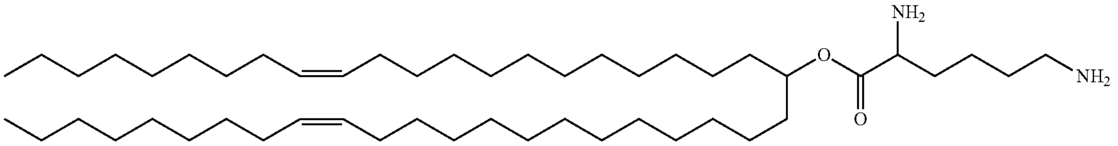

Lipid (CEg) is a lipid in which the number of carbon atoms in the hydrocarbon group of the lipophilic region of lipid (CEd) is changed. In the method for synthesizing lipid (CEg), the step of synthesizing a lipophilic region in the synthesis step was carried out by the same procedure as for the steps of step (a1) to step (a5) for lipid (Ia). In addition, the step of attaching the first amino acid to the lipophilic region was carried out in the same manner as for step (CEd1) and step (CEd2) for lipid (CEd) to obtain lipid (CEg).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.09-1.86 (m, 10H), 1.54-1.66 (4H,), 1.38-1.18 (m, 58H), 0.87 (t, J=6.9 Hz, 6H)

Comparative Example 8

Synthesis of (3Z,15Z)-docosa-3,15-dien-7-yl lysinate (hereinafter also referred to as lipid (CEh))

[Formula 79]

(CEh)

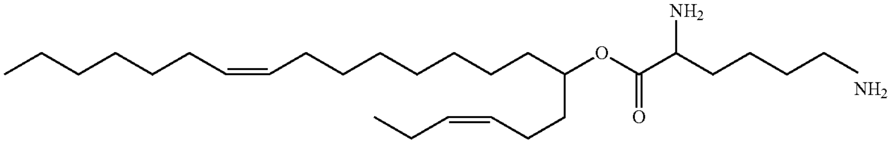

Lipid (CEh) is a lipid in which the number of carbon atoms in the hydrocarbon group of the lipophilic region of lipid (CEd) is changed. In the method for synthesizing lipid (CEh), the step of synthesizing a lipophilic region was carried out by the same procedure as for the steps of step (a1) to step (a5) for lipid (Ia). In addition, the step of attaching the first amino acid to the lipophilic region was carried out in the same manner as for step (CEd1) and step (CEd2) for lipid (CEd) to obtain lipid (CEh).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.09-1.86 (m, 8H), 1.54-1.66 (6H), 1.38-1.18 (m, 22H), 1.09 (3H, t, J=7.5 Hz), 0.87 (t, J=6.9 Hz, 3H)

Comparative Example 9

Synthesis of (3Z,19Z)-octacosa-3,19-dien-7-yl lysinate (hereinafter also referred to as lipid (CEi))

[Formula 80]

(CEi)

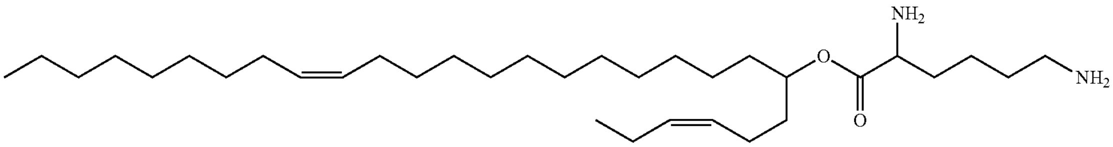

Lipid (CEi) is a lipid in which the number of carbon atoms in the hydrocarbon group of the lipophilic region of lipid (CEd) is changed. In the method for synthesizing lipid (CEi), the step of synthesizing a lipophilic region was carried out by the same procedure as for the steps of step (a1) to step (a5) for lipid (Ia). In addition, the step of attaching the first amino acid to the lipophilic region was carried out in the same manner as for step (CEd1) and step (CEd2) for lipid (CEd) to obtain lipid (CEi).

$^1$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.09-1.86 (m, 14H), 1.54-1.66 (14H), 1.38-1.18 (m, 30H), 1.09 (3H, t, J=7.5 Hz), 0.87 (t, J=6.9 Hz, 3H)

Comparative Example 10

Synthesis of 3-(2-amino-5-guanidinopentanamido)-4-(2,3-bis(((Z)-heptadec-8-enoyl)oxy)propoxy)-4-oxobutanoic acid (hereinafter referred to as lipid (CEj))

[Formula 81]

(CEj)

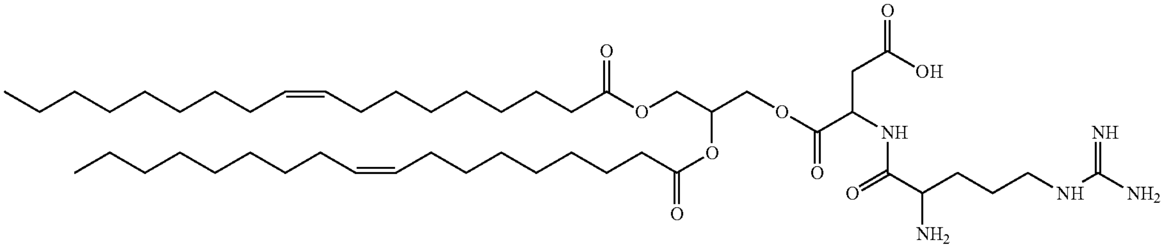

Lipid (CEj) is a lipid in which the hydrocarbon group of the lipophilic region of lipid (Ia) is changed. Hereinafter, a method for synthesizing lipid (CEj) will be described.

[Formula 82]

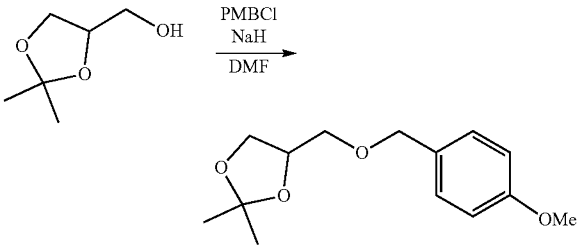

(2,2-Dimethyl-1,3-dioxolan-4-yl)methanol (5.0 g, 37.8 mmol) was dissolved in DMF (250 mL), the resulting solution was cooled to 0° C., and sodium hydride (1.2 g, 50.3 mmol) was added thereto. The resulting mixture was stirred at room temperature until the next day and cooled to 0° C., and 4-methoxybenzyl chloride (7.1 g, 45.4 mmol) was added dropwise. The resulting mixture was stirred at room temperature for 1 hour, then quenched with water, and extracted with heptane, the organic phase was washed with ion exchanged water, and then the organic phase was concentrated under reduced pressure. The resulting crude product was purified by silica gel column chromatography (ethyl acetate/heptane) to obtain the target 4-(((4-methoxybenzyl)oxy)methyl)-2,2-dimethyl-1,3-dioxolane (8.6 g, 34.1 mmol, 90%).

[Formula 83]

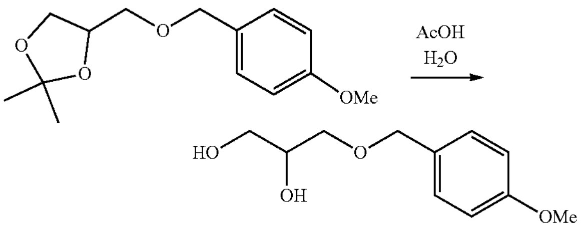

4-(((4-Methoxybenzyl)oxy)methyl)-2,2-dimethyl-1,3-dioxolane (8.6 g, 34.1 mmol) was dissolved in water (40 mL) and acetic acid (160 mL), and the resulting solution was heated to a temperature of 50° C. and allowed to react for 1 hour. After completion of the reaction, the crude product obtained by concentration under reduced pressure was purified by silica gel column chromatography (ethyl acetate/heptane) to obtain the target 3-((4-methoxybenzyl)oxy)propane-1,2-diol (6.4 g, 30.0 mmol, 88%).

[Formula 84]

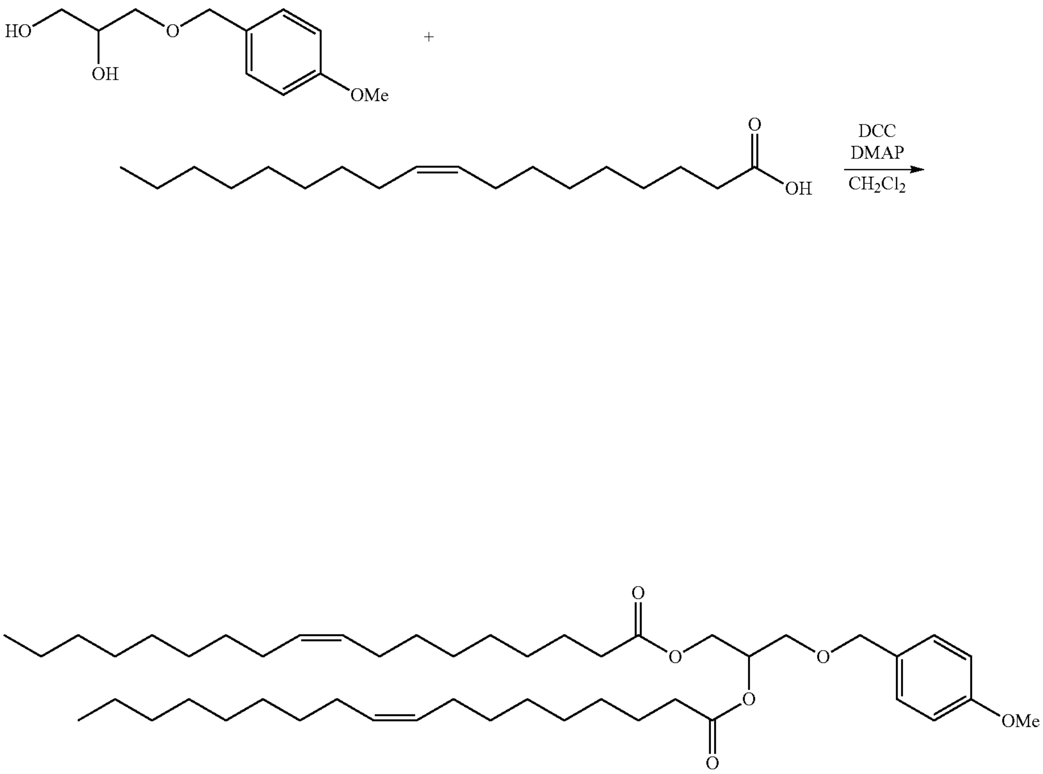

3-((4-Methoxybenzyl)oxy)propane-1,2-diol (6.4 g, 30.0 mmol), oleic acid (10.2 g, 36.0 mmol), DCC (7.4 g, 36.0 mmol), and DMAP (0.37 g, 3.0 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 3-((4-methoxybenzyl)oxy)propane-1,2-diyl dioleate (10.2 g, 13.8 mmol, 46%).

[Formula 85]

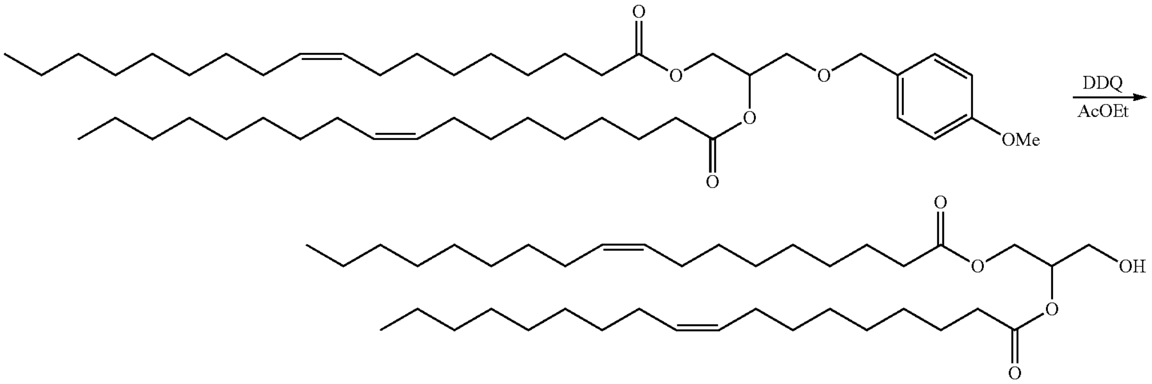

3-((4-Methoxybenzyl)oxy)propane-1,2-diyl dioleate (10.2 g, 13.8 mmol) was dissolved in ethyl acetate (120 mL) and water (12 mL), 2,3-dichloro-5,6-dicyano-p-benzoquinone (DDQ) (6.0 g, 49.2 mmol) was added thereto, and the resulting mixture was stirred at room temperature until the next day. After completion of the reaction, a crystal was removed by filtration, and the filtrate was concentrated. The resulting crude product was purified by silica gel column chromatography (ethyl acetate/heptane) to obtain the target 3-hydroxypropane-1,2-diyl dioleate (6.5 g, 10.5 mmol, 76%).

[Formula 86]

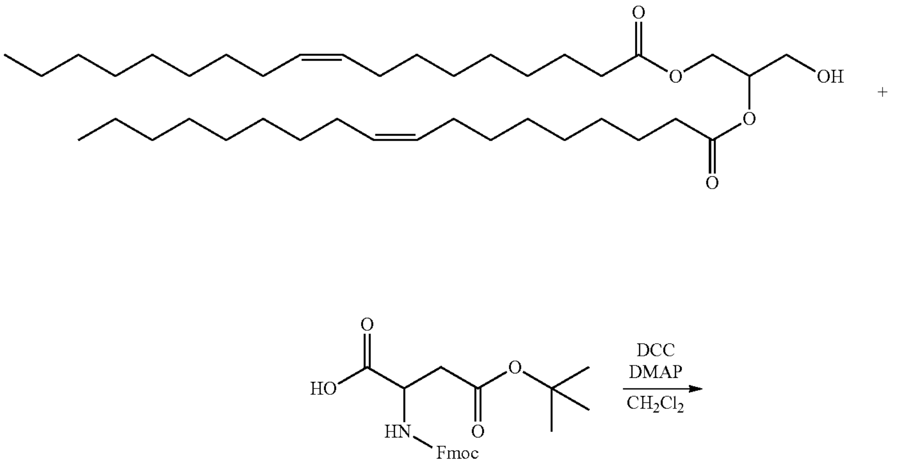

-continued

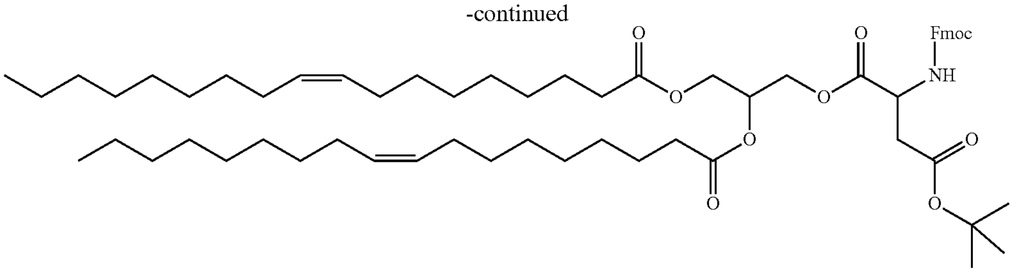

3-Hydroxypropane-1,2-diyl dioleate (2.0 g, 3.2 mmol), Fmoc-Asp(tBu)-OH (1.59 g, 3.8 mmol), in which to the amino group and the carbonyl group of aspartic acid, protective groups (Fmoc group and tBu group, respectively) had been attached in advance, DCC (1.33 g, 6.4 mmol), and DMAP (0.2 g, 1.6 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 1-(2,3-bis (oleoyloxy)propyl) 4-(tert-butyl) (((9H-fluoren-9-yl) methoxy)carbonyl)aspartate (3.1 g, 3.0 mmol, 95%).

[Formula 87]

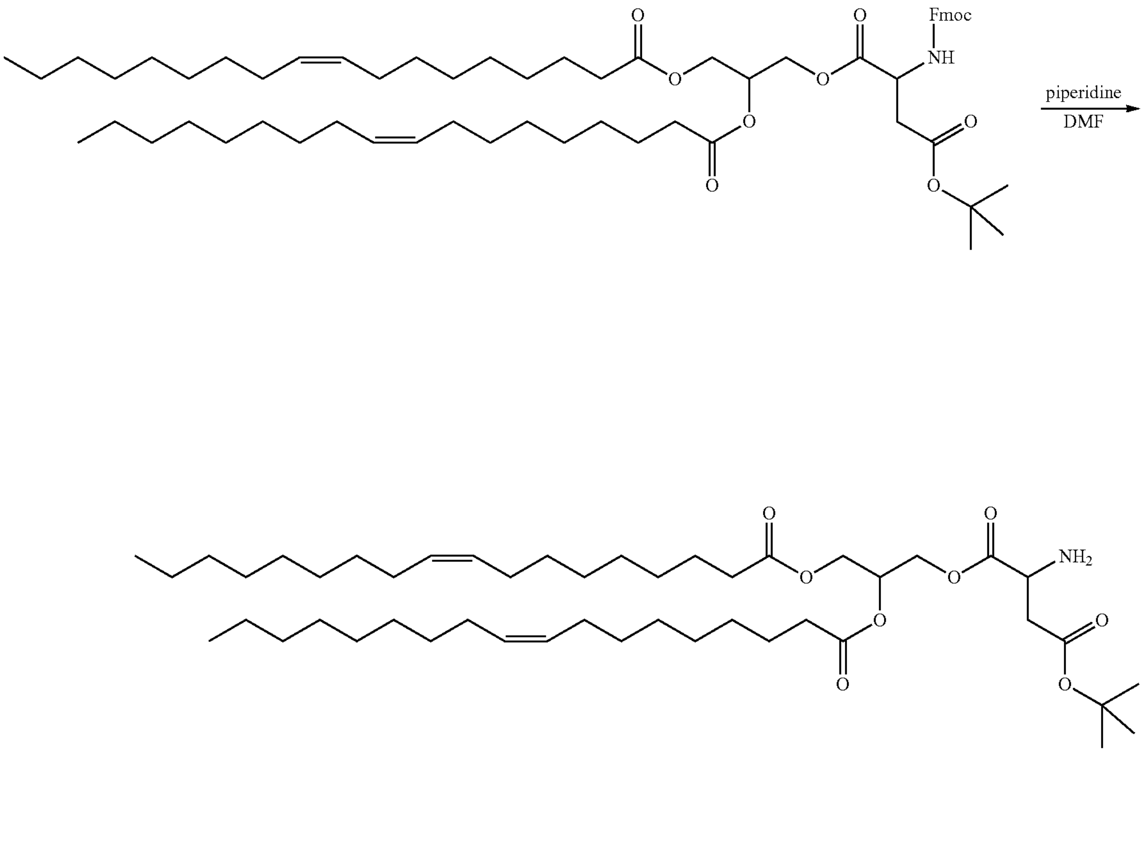

1-(2,3-Bis(oleoyloxy)propyl) 4-(tert-butyl) (((9H-fluoren-9-yl)methoxy)carbonyl)aspartate (3.1 g, 3.0 mmol) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 1-(2,3-bis(oleoyloxy)propyl) 4-(tert-butyl) aspartate (1.75 g, 2.2 mmol, 72%).

[Formula 88]

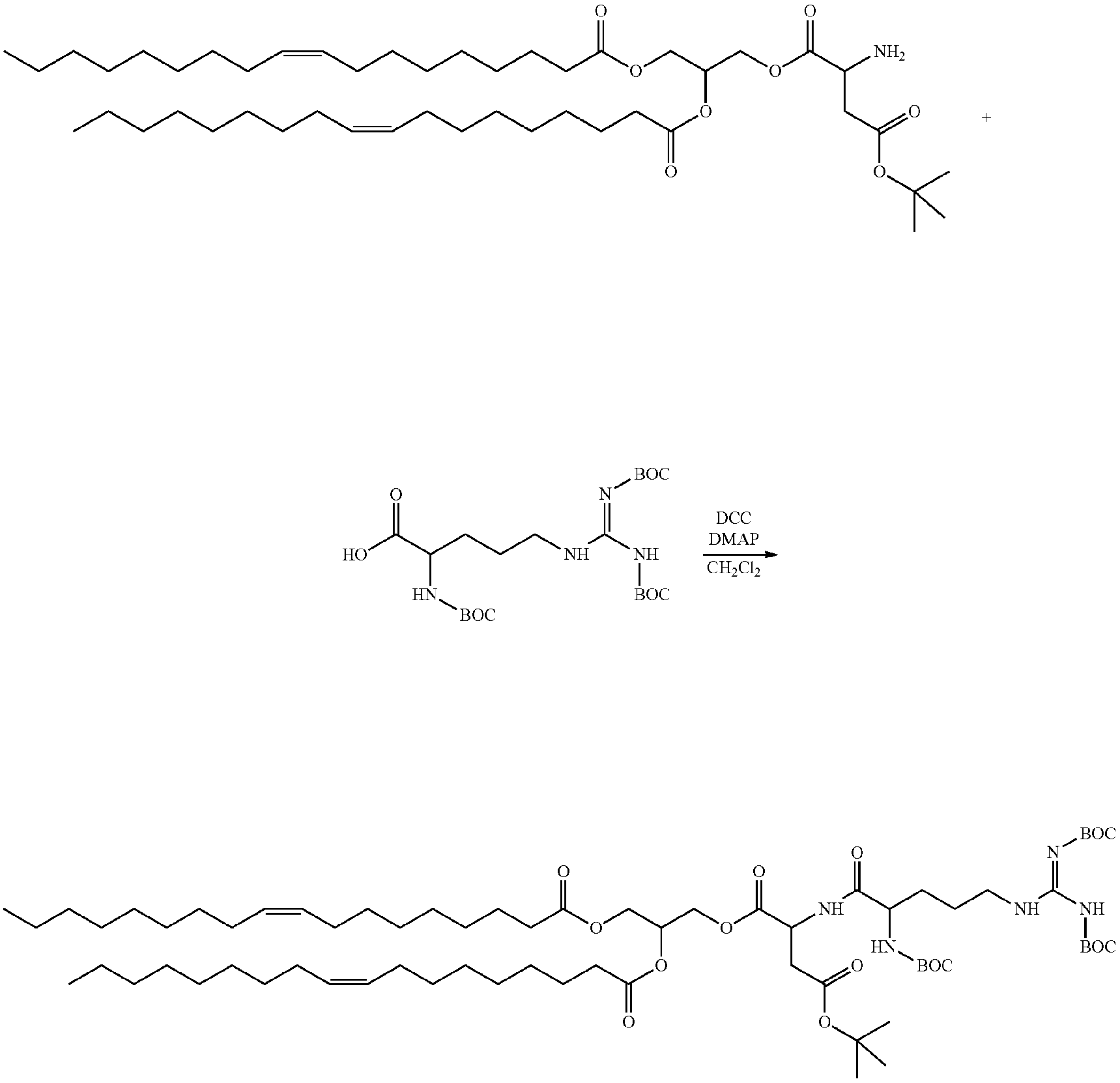

1-(2,3-Bis(oleoyloxy)propyl) 4-(tert-butyl) aspartate (1.75 g, 2.2 mmol), Boc-Arg(Boc)2-OH (1.72 g, 2.6 mmol) in which to the amino group and the guanidino group of arginine, protective group(s) (Boc group(s)) had been attached in advance, DCC (0.55 g, 2.6 mmol), and DMAP (27 mg, 0.22 mmol) were dissolved in dichloromethane (13 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 1-(2,3-bis(oleoyloxy)propyl) 4-(tert-butyl) N2,Nw,Nw'-tris(tert-butoxycarbonyl)arginylaspartate was obtained (1.6 g, 1.2 mmol, 58%).

[Formula 89]

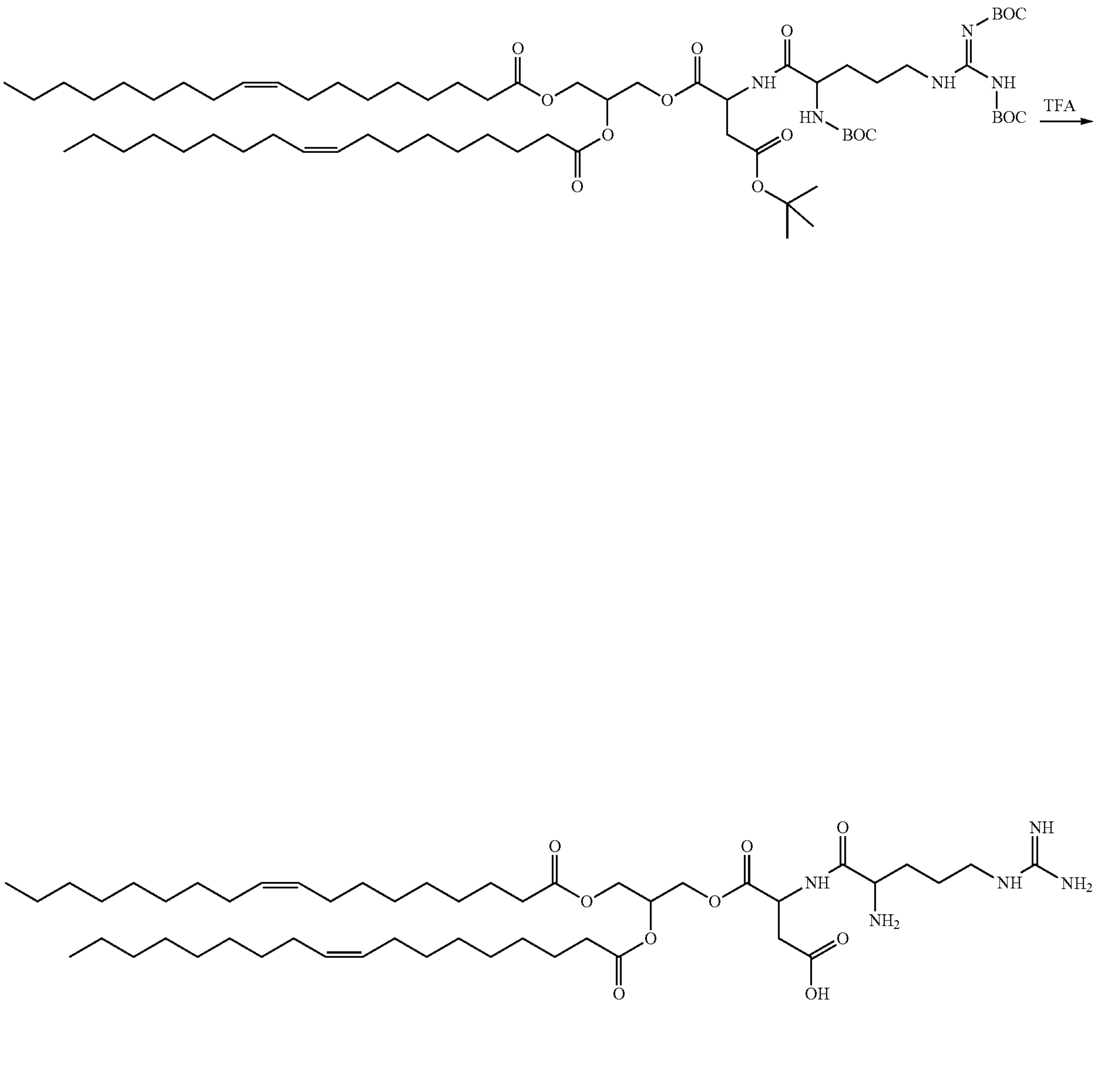

1-(2,3-Bis(oleoyloxy)propyl) 4-(tert-butyl) N2,Nw,Nw'-tris(tert-butoxycarbonyl)arginylaspartate (1.6 g, 1.2 mmol) was dissolved in TFA (4 mL). The resulting solution was stirred at room temperature for 1 hour, and then the solvent was concentrated under reduced pressure. The resulting crude product was purified by silica gel column chromatography (ethyl acetate/methanol) to obtain the target 1-(2,3-bis(oleoyloxy)propyl) 4-(tert-butyl) arginylaspartate (0.30 g, 0.33 mmol, 26%).

$^1$H-NMR (400 MHz, CHLOROFORM-D) δ 5.32 (m, 4H), 5.30-5.18 (m, 1H), 4.90-4.75 (m, 1H), 4.35-4.05 (m, 4H), 3.15-3.02 (4H), 2.95-2.20 (m, 4H), 2.12-1.81 (m, 10H), 1.65-1.42 (m, 12H), 1.35-0.98 (m, 28H), 0.86 (t, 6H)

Comparative Example 11

Synthesis of 3-(2-amino-5-guanidinopentanamido)-4-((2,3-bis(((Z)-heptadec-8-enoyl)oxy)propyl)amino)-4-oxobutanoic acid (hereinafter also referred to as lipid (CEk))

[Formula 90]

(CEk)

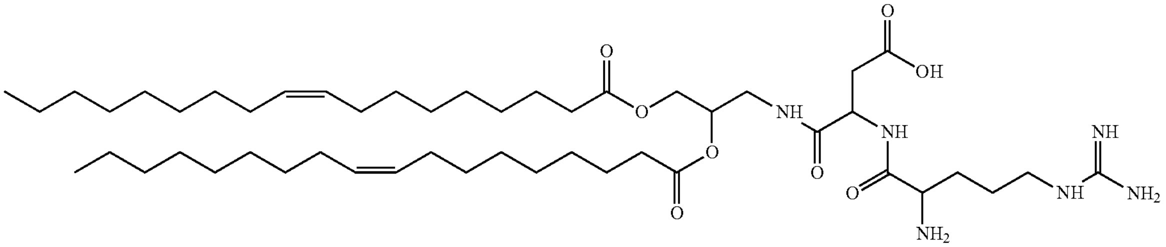

Lipid (CEk) is a lipid in which the hydrocarbon group of the lipophilic region of lipid (Ia) is changed. Hereinafter, a method for synthesizing lipid (CEk) will be described.

[Formula 91]

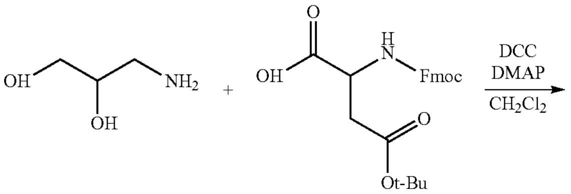

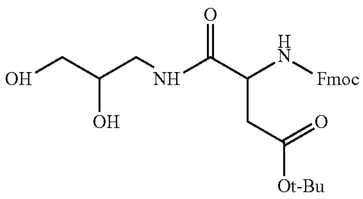

Fmoc-Asp(tBu)-OH (3.4 g, 8.3 mmol), DCC (2.3 g, 10.8 mmol), and DMAP (0.10 g, 8.3 mmol) were dissolved in dichloromethane (105 mL), and the resulting mixed solution was stirred at room temperature for 2 hours. To this solution, 3-amino-1,2-propanediol (4.0 g, 7.7 mmol) dissolved in DMF (55 mL) was added, the resulting mixture was stirred at room temperature until the next day and then quenched with water, and the precipitated dicyclohexylurea was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target tert-butyl 3-((((9H-fluoren-9-yl)methoxy)carbonyl)amino)-4-((2,3-dihydroxypropyl)amino)-4-oxobutanoate (3.5 g, 7.2 mmol, 87%).

[Formula 92]

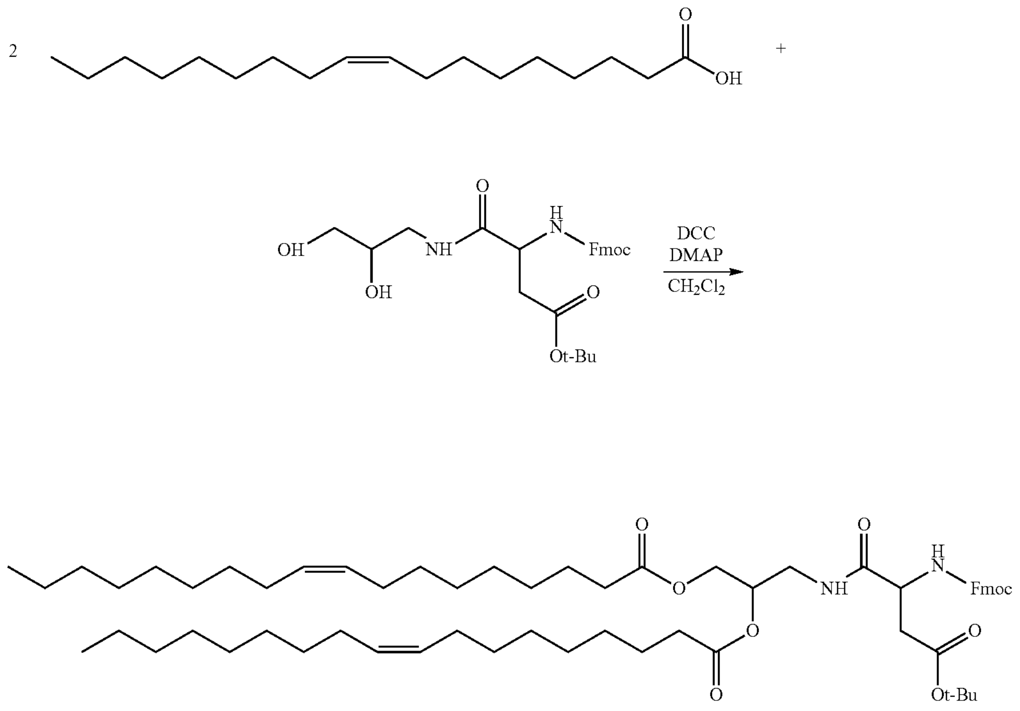

tert-Butyl 3-((((9H-fluoren-9-yl)methoxy)carbonyl)amino)-4-((2,3-dihydroxypropyl)amino)-4-oxobutanoate (3.5 g, 7.5 mmol), oleic acid (4.47 g, 15.8 mmol), DCC (3.89 g, 18.8 mmol), and DMAP (0.09 g, 0.8 mmol) were dissolved in dichloromethane (30 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 3-(2-((((9H-fluoren-9-yl)methoxy)carbonyl)amino)-4-(tert-butoxy)-4-oxobutanamido)propane-1,2-diyl dioleate (3.4 g, 3.4 mmol, 45%).

[Formula 93]

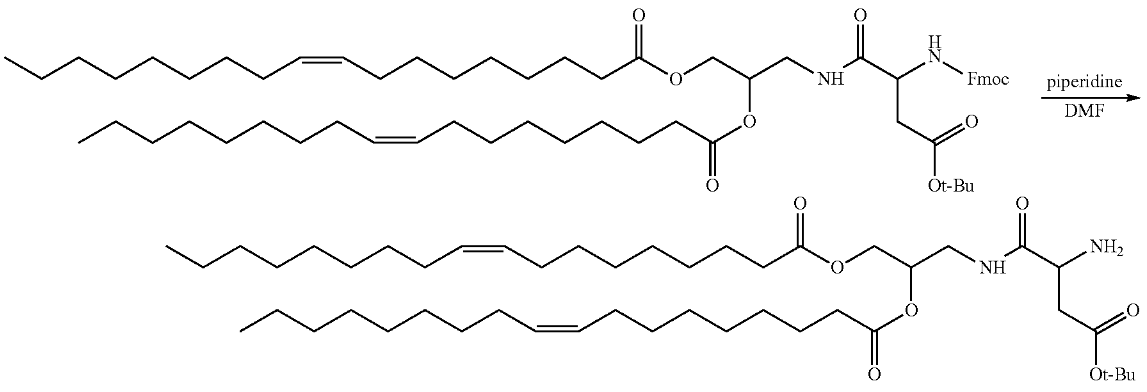

3-(2-((((9H-Fluoren-9-yl)methoxy)carbonyl)amino)-4-(tert-butoxy)-4-oxobutanamido)propane-1,2-diyl dioleate (3.5 g, 3.5 mmol) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 3-(2-amino-4-(tert-butoxy)-4-oxobutanamido)propane-1,2-diyl dioleate (3.2 g, 3.2 mmol, 91%).

[Formula 94]

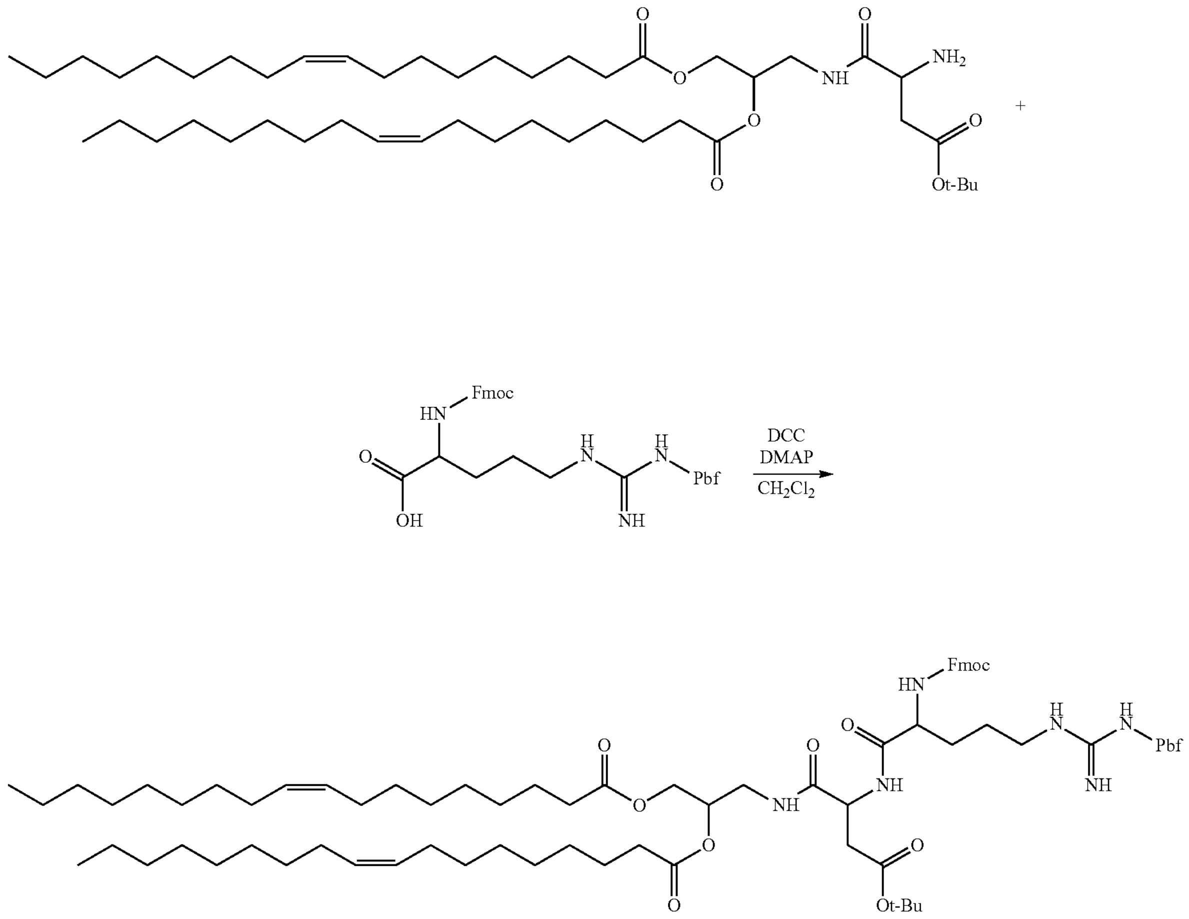

3-(2-Amino-4-(tert-butoxy)-4-oxobutanamido)propane-1,2-diyl dioleate (1.0 g, 1.3 mmol), Fmoc-Arg(Pbf)-OH (0.9 g, 1.4 mmol) (manufactured by TCI), DCC (0.31 g, 1.5 mmol), and DMAP (0.03 g, 0.3 mmol) were dissolved in dichloromethane (13 mL). The resulting solution was stirred at room temperature until the next day, and then quenched with water, and dicyclohexylurea precipitated was removed by filtration. The residue obtained by concentrating the filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 8-(2-(tert-butoxy)-2-oxoethyl)-1-(9H-fluoren-9-yl)-3,6,9-trioxo-5-(3-(3-((2,2,4,6,7-pentamethyl-2,3-dihydrobenzofuran-5-yl)sulfonyl)granidino)propyl)-2-oxa-4,7,10-triazatridecane-12,13-diol diureate (1.68 g, 1.2 mmol, 93%).

[Formula 95]

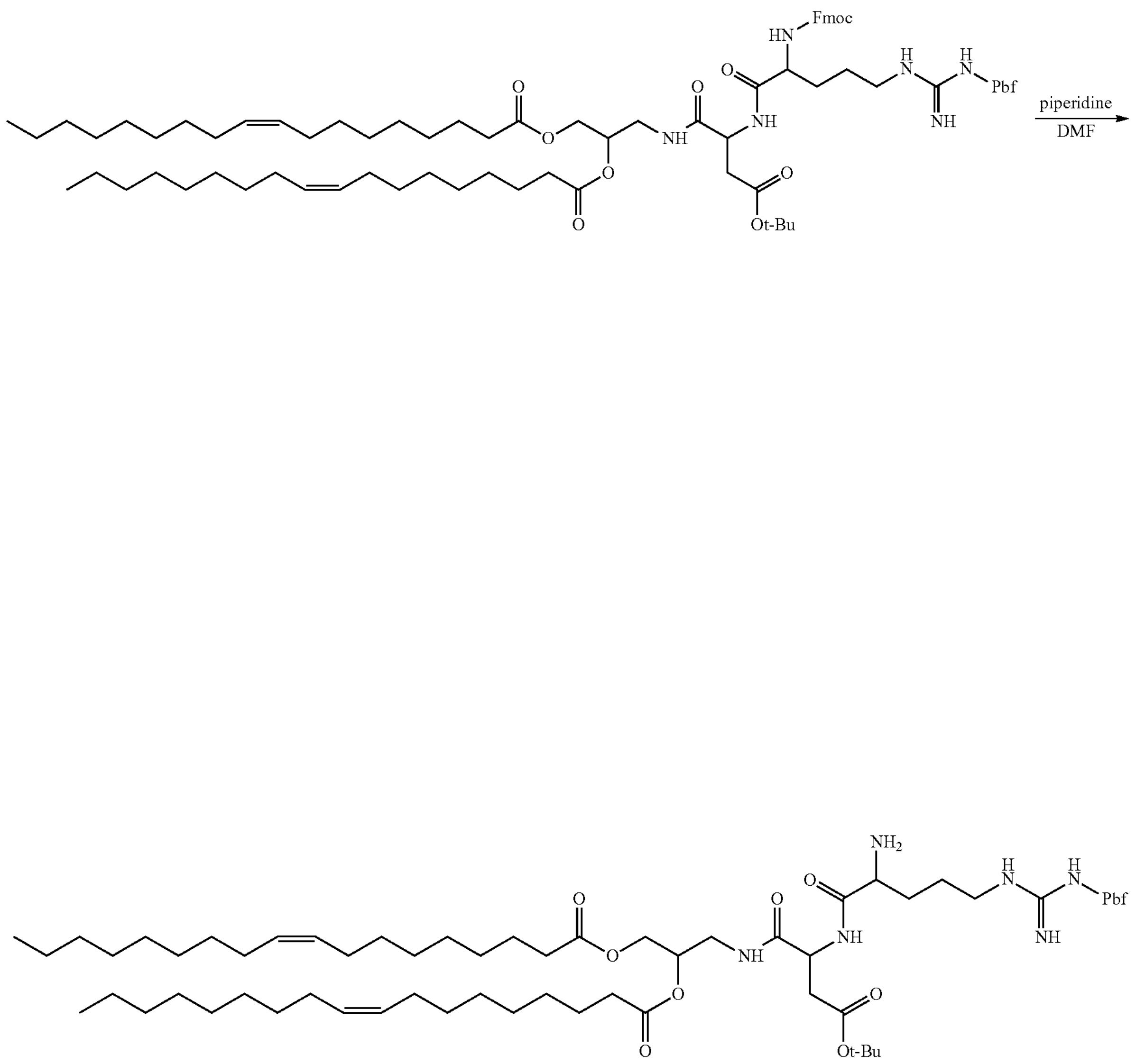

8-(2-(tert-Butoxy)-2-oxoethyl)-1-(9H-fluoren-9-yl)-3,6,9-trioxo-5-(3-(3-((2,2,4,6,7-pentamethyl-2,3-dihydrobenzofuran-5-yl)sulfonyl)granidino)propyl)-2-oxa-4,7,10-triazatridecane-12,13-diol diureate (1.68 g, 1.2 mmol) was dissolved in a 20% piperidine/DMF solution (6 mL). The resulting solution was stirred at room temperature until the next day, and then the solvent was concentrated under reduced pressure. The residue was dispersed in ethyl acetate, and the precipitate was removed by filtration. The filtrate was dissolved in ethyl acetate, the organic phase was washed with 10% hydrochloric acid, saturated aqueous sodium bicarbonate, and ion exchanged water, and then the organic phase was concentrated under reduced pressure. The resulting crude product was purified by silica gel column chromatography (ethyl acetate/heptane) to obtain the target 3-(2-(2-amino-5-(3-((2,2,4,6,7-pentamethyl-2.3-dihydrobenzofuran-5-yl)sulfonyl)guanidino)pentanamido)-4-(tert-butoxy)-4-oxobutanamido)propane-1,2-diethyl diolein (1.2 g, 1.0 mmol, 85%).

[Formula 96]

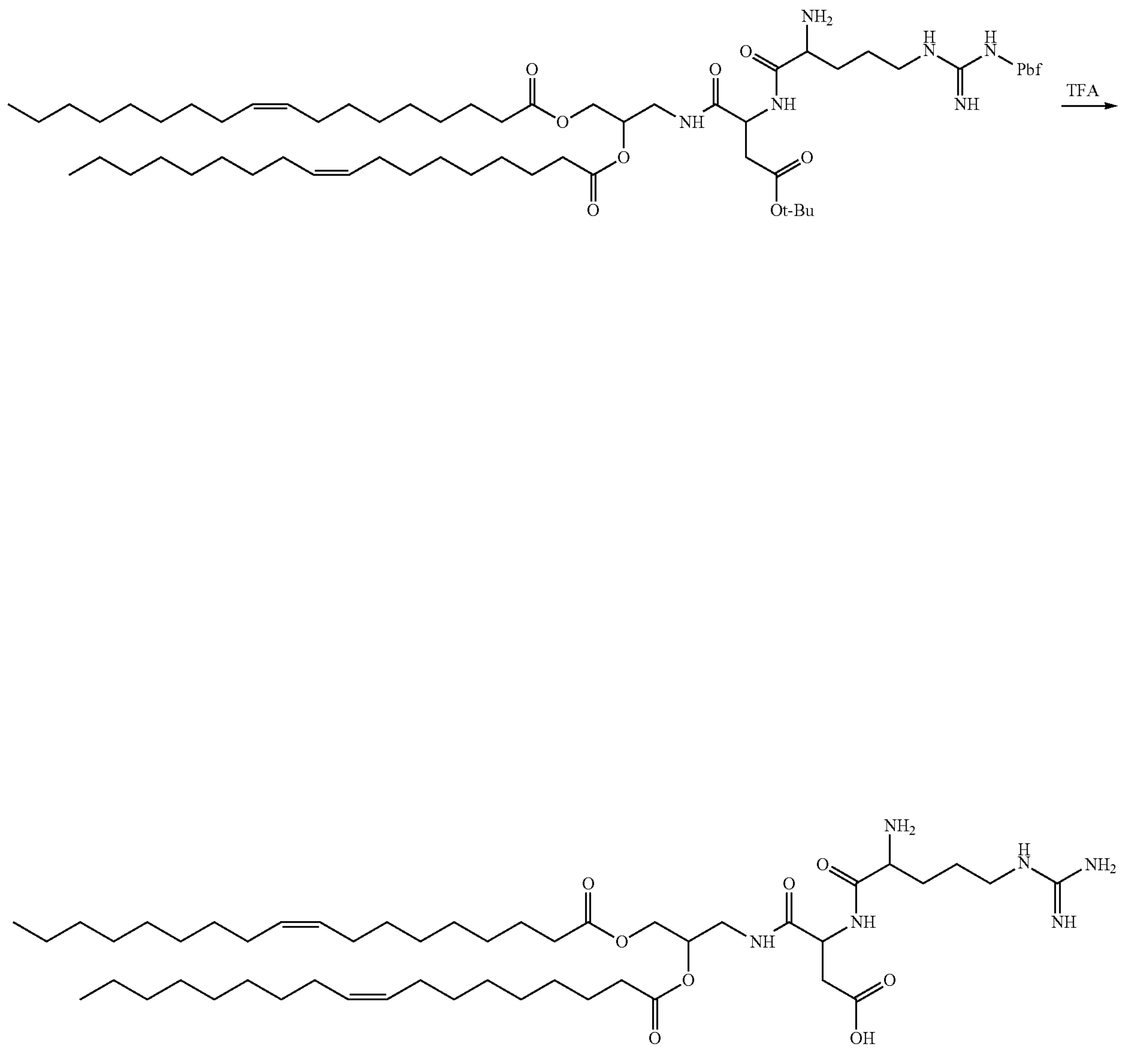

3-(2-(2-Amino-5-(3-((2,2,4,6,7-pentamethyl-2,3-dihydrobenzofuran-5-yl)sulfonyl)guanidino)pentanamido)-4-(tert-butoxy)-4-oxobutanamido)propane-1,2-diethyl diolein (1.2 g, 1.0 mmol) was dissolved in TFA (4 mL). The resulting solution was stirred at room temperature for 1 hour, and then the solvent was concentrated under reduced pressure. The resulting crude product was purified by silica gel column chromatography (ethyl acetate/methanol) to obtain the target lipid (CEk) (0.24 g, 0.27 mmol, 27%).

$^{1}$H-NMR (400 MHz, CHLOROFORM-D) δ 5.34 (d, J=17.4 Hz, 4H), 5.08 (s, 1H), 4.94-4.64 (1H), 4.21 (s, 1H), 4.02 (s, 1H), 3.39 (s, 1H), 3.01 (s, 1H), 2.43-2.14 (m, 4H), 1.99-1.70 (m, 10H), 1.55 (s, 5H), 1.26 (m, 46H), 0.86 (t, J=6.6 Hz, 6H)

Comparative Example 12

Synthesis of (9Z,27Z)-hexatriaconta-9,27-dien-18-yl methioninate (hereinafter also referred to as lipid (CEl))

[Formula 97]

(CEj)

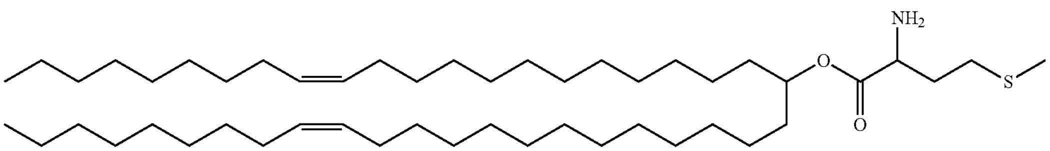

Lipid (CEl) is a lipid in which the first amino acid of lipid (CEa) is changed to Met.

The step of synthesizing a lipophilic region in the method for synthesizing lipid (CEl) is the same as the steps of step (a1) to step (a5) for lipid (Ia). In addition, the step of binding the first amino acid to the lipophilic region was carried out by the same procedure as for the steps of step (f6) and step (f7) for lipid (If).

$^{1}$H-NMR (400 MHz, CHLOROFORM-D) δ 5.44-5.25 (m, 4H), 4.87 (t, J=5.9 Hz, 1H), 3.48-3.31 (m, 1H), 3.20-3.16 (t, 1H), 2.70-2.66 (t, 1H), 2.19 (s, 3H), 2.09-1.86 (m, 10H), 1.78-1.52 (m, 4H), 1.38-1.18 (m, 46H), 0.87 (t, J=6.9 Hz, 6H)

Reference Example 1

Lipid (r1) (manufactured by Cayman Chemical Company, SM102-33474) was used as a reference lipid for comparison of each evaluation.

[Formula 98]

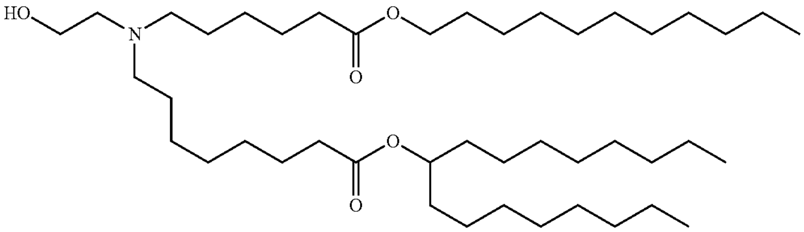

<Evaluations>

Subsequently, by using the lipids of the above Examples and Comparative Examples, compositions including lipid nanoparticles encapsulating an siRNA and an mRNA were produced, and each evaluation thereof was carried out.

[Production of Lipid Nanoparticle (LNP)]

A. Preparation of Lipid Solution and Citrate Buffer

First, a lipid solution was prepared by using any of the lipids of the Examples and the Comparative Examples. The preparation was carried out according to the following procedure.

(i) An ethanol solution of a predetermined lipid (10 mM, hereinafter also referred to as the main lipid) of the Examples and the Comparative Examples, an ethanol solution of a helper lipid (DPPC (dipalmitoylphosphatidylcholine): 10 mM) different from the main lipid, and an ethanol solution of cholesterol (10 mM) was produced.

(ii) Each of the solutions prepared in (i) above was mixed in such a way as to provide main lipid/helper lipid/cholesterol=45/10/45 (molar ratio), to obtain a lipid solution.

Next, a citrate buffer was prepared. Specifically, 50 mL of a 1 mM citric acid aqueous solution and 50 mL of a 1 mM sodium citrate aqueous solution were each produced. The citric acid aqueous solution and the sodium citrate aqueous solution were mixed while checking with a pH meter, to prepare a 1 mM citrate buffer with pH=4.5.

B. Production of Lipid Nanoparticle

Subsequently, a lipid nanoparticle was produced by using a microchannel. The microfluidic method is a method for producing a lipid nanoparticle by mixing a lipid solution with an siRNA solution or an mRNA solution by using a microreactor. As the siRNA solution, a solution obtained by dissolving a 21 base-pair siRNA in RFW (RNase Free Water) was used, and as the mRNA solution, CleanCap FLuc mRNA (catalog number L-7602-100) from TriLink BioTechnologies (manufacturer) was used.

First, a procedure of a method for producing a lipid nanoparticle containing an siRNA will be described below.

(i) The lipid solution, the 1 mM citrate buffer, and ethanol for washing were kept in an incubator set at 25° C.

(ii) A microchannel (manufactured by YMC Co., Ltd., KC-M-S-SUS) was washed by flowing ethanol on the lipid solution side and RFW on the siRNA solution side.

(iii) Required amounts of the 1 mM citrate buffer and the siRNA solution were mixed to produce an siRNA citrate buffer solution.

(iv) 0.33 mL of the lipid solution and 1.66 mL of the siRNA citrate buffer solution were taken in separate syringes and set in respective pumps. The lipid solution and the siRNA citrate buffer solution were set such that the total flow rate was 3.3 mL/min and such that the molar ratio of the total lipid to the siRNA was 7000:1, the lipid concentration was 1.7 mM, and the solvent ratio (alcohol concentration) was 24.1%.

(v) The apparatus was started to vigorously mix the lipid solution and the siRNA citrate buffer solution in the channel. The first about 750 μL was discarded, and the rest of the solution was collected in an Eppendorf tube.

Next, a procedure of a method for producing a lipid nanoparticle containing an mRNA will be described below.

(i) The lipid solution and the 1 mM citrate buffer were kept in an incubator set at 25° C.

(ii) A microchannel (manufactured by YMC Co., Ltd., KC-M-S-SUS) was washed by flowing ethanol of a lipid solution on the lipid solution side and RFW on the mRNA solution side.

(iii) Required amounts of a 1 mM citrate buffer and the mRNA solution were mixed to produce an mRNA citrate buffer solution. As the 1 mM citrate buffer here, one adjusted to pH 4.5 by using an acidic 1 mM citrate buffer was used.

(iv) 0.522 mL of the lipid solution and 1.478 mL of the mRNA citrate buffer solution were taken in separate syringes and set in respective pumps. The amounts of the lipid solution and the mRNA citrate buffer solution were adjusted such that the weight ratio of the lipid and the mRNA was 30:1.

(v) The apparatus was started with the flow rate of the lipid solution set at 685.7 μL/min and the flow rate of the mRNA citrate buffer solution set at 2.914 mL/min, and the lipid solution and the mRNA citrate buffer solution were vigorously mixed in the channel. The first about 13.75 seconds was discarded, and the rest of the solution was collected in an Eppendorf tube.

A method for producing a lipid nanoparticle containing an mRNA using lipid (r1) of Reference Example 1 will be described below.

Production of a lipid nanoparticle containing an mRNA using lipid (r1) was carried out in the same manner as in the method for producing a lipid nanoparticle containing an mRNA using the lipid of each Example, except for the following changes.

Production of a lipid solution was carried out as follows. (i) An ethanol solution of lipid (r1) (10 mM), an ethanol solution of a helper lipid (DSPC (1,2-distearoyl-sn-glycero-3-phosphocholine): 10 mM), an ethanol solution of cholesterol (10 mM), and an ethanol solution of PEG2000-DMG (10 mM) was produced. (ii) Each of the solutions prepared in (i) above was mixed in such a way as to provide main lipid/helper lipid/cholesterol/PEG2000-DMG=50/10/38.5/1.5 (molar ratio), to obtain a lipid solution.

Subsequently, the method for producing a lipid nanoparticle containing an mRNA was carried out in the same manner as in the method for producing a lipid nanoparticle containing an mRNA using the lipid of each Example, except that (iv) the amounts of the lipid solution and the mRNA citrate buffer solution were adjusted such that the weight ratio of lipid (r1) to the mRNA was 19.35:1.

Subsequently, the lipid nanoparticle-containing solution including an siRNA or an mRNA obtained as described above was dialyzed by using a dialysis membrane (manufactured by REPLIGEN Corporation, Spectra/Por 2 Membrane) to remove an organic solvent such as ethanol used, a salt included in the buffer, and the like. The procedure will be shown below.

(i) The dialysis membrane was cut to the required length and soaked in water to activate the same.

(ii) The activated dialysis membrane was drained and clipped at the bottom to prevent the lipid nanoparticle-containing solution from leaking from the bottom.

(iii) The lipid nanoparticle-containing solution was placed in the dialysis membrane while metered with a pipette, and after completion thereof, the dialysis membrane was clipped at the top.

(iv) The dialysis membrane was placed in a container (beaker or the like) filled with a large amount of water, and the water was stirred with a stirrer at a speed at which the dialysis membrane was gently rotated. The water was stirred overnight while exchanging the water several times during the stirring.

(v) After completion of dialysis, the dialysis membrane was taken out from the water. The dialysis membrane was opened by using scissors, and the contents thereof were transferred to another container while metered with a pipette.

[Measurement of Particle Size, Polydispersity Index, and Zeta Potential of Lipid Nanoparticle]

30 μL of each of the dialyzed lipid nanoparticle-containing solutions obtained by the above operation was measured out, 800 μL of ultrapure water was added to dilute the lipid nanoparticle-containing solution, and the diluted preparation solution was used to measure the particle size (nm) and the polydispersity index (PDI) by using a Zetasizer (manufactured by Malvern Panalytical, Zetasizer nano Ultra). The particle size was evaluated by Z-average in ultrapure water. The zeta potential was measured by using pH 7.4 Tris-HCl as a dilute solution.

[Evaluation of siRNA Encapsulation Rate and mRNA Encapsulation Rate of Lipid Nanoparticle]

The siRNA encapsulation rate and the mRNA encapsulation rate of the lipid nanoparticle were obtained as follows. First, a surfactant (Sigma-Aldrich, Triton (registered trademark), X-100 (reducing type)) was added to the lipid nanoparticle-containing solution to disrupt the lipid nanoparticle to release the encapsulated siRNA or mRNA. The amounts of the lipid nanoparticle-containing solution and the surfactant were adjusted such that the siRNA or the mRNA was 2 pmol and the surfactant was 1% in 40 μL of the solution after adding the surfactant to the lipid nanoparticle-containing solution. Next, the RiboGreen reagent (reagent that reacts with siRNA to emit fluorescence, manufactured by Thermo Fisher Scientific, Quant-iT (registered trademark) RiboGreen (registered trademark) RNA Assay Kit) was added to the solution, and the fluorescence intensity was measured under conditions of an excitation wavelength of 480 nm and a fluorescence wavelength of 520 nm with a fluorescence intensity meter (manufactured by TECAN, Infinite M200). Specifically, 75 μL of the RiboGreen reagent diluted to 1/2000 was added to a diluted solution obtained by adding 65 μL of citrate buffer to 10 μL of the solution, and the fluorescence intensity was measured. This makes it possible to relatively measure the total amount of the siRNA or the total amount of the mRNA present in the solution.

Subsequently, the RiboGreen reagent was added to the lipid nanoparticle-containing solution without adding a surfactant, and the fluorescence intensity was measured in the same manner with a fluorescence intensity meter. By not adding a surfactant, it is possible to relatively measure the amount of the siRNA or the mRNA free in the solution without being encapsulated in the lipid nanoparticle.

Then, the fluorescence intensity obtained from the solution to which the surfactant was added obtained as described above was fluorescence intensity a, and the fluorescence intensity thus obtained from the solution to which no surfactant was added obtained as described above was fluorescence intensity b, and according to the expression $(a-b)/a\times 100$, the siRNA encapsulation rate (%) or the mRNA encapsulation rate (%) of the lipid nanoparticle was obtained. Each of fluorescence intensity a and fluorescence intensity b is a value obtained by subtracting a blank from the arithmetic average value of the results of three measurements for each solution. The blank was measured by carrying out the same operation on a well containing water containing no cell or lipid nanoparticle.

[Cell Experiment 1]

A cell experiment was carried out by using HT1080-EGFP (human/fibrosarcoma) cells in order to evaluate lipid nanoparticles encapsulating an siRNA produced by using the lipids of the Examples and the Comparative Examples. These cells are cells provided with a green fluorescent protein gene (EGFP). The expression of EGFP can be easily confirmed by measuring the fluorescence intensity of a solution in which the cells are lysed, and thus by acting lipid nanoparticles encapsulating an siRNA that suppresses the expression of EGFP and observing any decrease in fluorescence intensity, the performance of the lipid nanoparticles used can be evaluated. Hereinafter, the procedure of the cell experiment will be shown.

A. Provision of Cells (i) A liquid medium (DMEM/Ham's F12, FBS+, P/S+) (FBS: fetal bovine serum, P/S: antibiotic) was taken out from a refrigerator and temperature-controlled in an incubator set at 37° C.

(ii) A cryotube containing the cells was taken out from a −80° C. freezer and thawed at once in an incubator set at 37° C.

(iii) A stock solution of the thawed cells was collected in a capped test tube.

(iv) The tube containing the cells was washed with the liquid medium, and the wash was also collected in the test tube.

(v) The tube was subjected to a centrifuge to precipitate the cells.

(vi) The supernatant was aspirated, and the liquid medium was added and gently tapped to disperse the cells.

(vii) A small amount of the cells-dispersed liquid medium was collected, and the number of cells was observed and counted under a microscope.

(viii) The cells were seeded in a 24-well plate such that the number of cells was $2\times10^4$ cells per well. For the plate for an LDH assay described later, the cells were seeded in a 96-well plate such that the number of cells was $4\times10^3$ cells per well.

(ix) The 24-well plate or the 96-well plate was placed in an incubator, and the cells were cultured for 24 hours under conditions of 37° C. and 5% $CO_2$.

B. Transfection

The produced lipid nanoparticles were introduced into cells.

(i) Fetal bovine serum (FBS) was added to a liquid medium (FBS-, P/S-) temperature-controlled as in (i) of A above, in such a way as to reach 10%.

(ii) A 24-well plate was taken out from an incubator, and the liquid medium supernatant in the 24-well plate was aspirated and washed with phosphate buffered saline (PBS).

(iii) 400 μL of the liquid medium produced in (i) above was added to the washed 24-well plate. In addition, 100 μL of an LNP solution having an adjusted concentration was added.

(iv) The 24-well plate was placed in the incubator, and the cells were cultured (for 24 hours).

(v) After 24 hours, the liquid medium supernatant in the 24-well plate was aspirated, and 500 μL of a liquid medium containing 10% FBS (FBS+/P/S+) was added.

(vi) The 24-well plate was placed in the incubator, and the cells were cultured for 24 hours under conditions of 37° C. and 5% $CO_2$.

The introduction of lipid nanoparticles into cells for an LDH assay described later was carried out as follows.

(i) A 96-well plate was taken out from an incubator.

(ii) The liquid medium supernatant in the 96-well plate was aspirated and washed with phosphate buffered saline (PBS).

(iii) 160 μL of a liquid medium containing 10% FBS (FBS+/P/S+) was added to the washed 96-well plate. In addition, 40 μL of an LNP solution having an adjusted concentration was added.

(iv) The 96-well plate was placed in the incubator, and the cells were cultured for 24 hours under conditions of 37° C. and 5% $CO_2$.

C. Evaluation of Toxicity (CCK-8 Assay, LDH Assay)

For Examples 1 to 9, a CCK-8 assay or an LDH assay was carried out to measure the metabolic activity of viable cells and relatively quantify the number of surviving cells to evaluate the toxicity of lipid nanoparticles.

(a) CCK-8 Assay (i) Fetal bovine serum (FBS) and a viable cell counting kit (manufactured by DOJINDO LABORATORIES, Cell Count Kit-8) was added to a liquid medium (FBS-, P/S-) temperature-controlled as in (i) of A above, such that FBS was 10% and the kit was 10%.

(ii) A 24-well plate was taken out from an incubator. The liquid medium was removed, and 315 μL of the liquid medium containing the viable cell counting kit produced in (i) above was added.

(iii) The liquid medium was aged for 1 hour in the incubator.

(iv) The 24-well plate was taken out, and the absorbance was measured under conditions of a measurement wavelength of 450 nm and a target wavelength of 630 nm with a plate reader (manufactured by TECAN, Infinite M200). The absorbance was calculated with the absorbance of control cells to which no lipid nanoparticle was added set at 1.00. When the obtained value was 0.80 or more and 1.00 or less, a rating of double-circle (excellent) was given, when the obtained value was 0.50 or more and less than 0.80, a rating of circle (good) was given, when the obtained value was 0.20 or more and less than 0.50, a rating of triangle (fair) was given, and when the obtained value was less than 0.20, a rating of X-mark (poor) was given.

(b) LDH Assay

An LDH assay was carried out by using a viable cell counting kit (DOJINDO LABORATORIES, Cytotoxicity LDH Assay Kit-WST) as follows.

(i) 20 μL of a lysis buffer was added to each of positive control wells and incubated at 37° C. for 30 minutes in an incubator.

(ii) 100 μL of the supernatant was taken from each well and transferred to a 96-well plate for measurement.

(iii) 100 μL of the reagent mixture attached to the kit was added to all the wells, and a color reaction was carried out for 30 minutes at room temperature with exclusion of light.

(iv) 50 μL of the stop solution reagent attached to the kit was added to all the wells.

(v) The 96-well plate was measured under conditions of a measurement wavelength of 490 nm and a target wavelength of 630 nm with a plate reader (manufactured by TECAN, Infinite M200) to calculate the absorbance. The absorbance was calculated with the absorbance of control cells to which no lipid nanoparticle was added set at 1.00. When the obtained value was 0.50 or less, a rating of double-circle (excellent) was given, when the obtained value was more than 0.50 and 1.0 or less, a rating of circle (good) was given, when the obtained value was more than 1.0 and less than 6.0, a rating of triangle (fair) was given, and when the obtained value was 6.0 or more, a rating of X-mark (poor) was given.

D. Evaluation of Knockdown Effect (GFP Assay)

By carrying out a GFP assay, the EGFP expression level in cells was measured to evaluate the effect of knocking down the green fluorescent protein gene (EGFP) by lipid nanoparticles.

(i) A 24-well plate was taken out from an incubator and washed with PBS.

(ii) A 1% octylglucoside solution to which a protease inhibitor was added was added in order to disrupt cells. Stirring with a pipette lysed the cells.

(iii) The cell lysate was transferred to an Eppendorf tube and subjected to a centrifuge.

(iv) 150 μL of the supernatant was collected and added to a plate for fluorescence measurement.

(v) The fluorescence intensity was measured under conditions of an excitation wavelength of 485 nm and a fluorescence wavelength of 535 nm with a plate reader (manufactured by TECAN, Infinite M200). The fluorescence intensity was calculated with the fluorescence intensity of control cells to which no lipid nanoparticle was added set at 100.

[Cell Experiment 2]

For lipids (Ia), (Ib), and (Ie) of Examples 1, 2, and 5, a cell experiment was carried out by using HEK293T cells and NIH3T3 cells in order to evaluate lipid nanoparticles encapsulating an mRNA. By transfecting the cells with lipid nanoparticles and measuring the amount of a predetermined protein produced, the performance of the lipid nanoparticles used can be evaluated. Hereinafter, the procedure of the cell experiment will be shown.

A. Seeding of Cells (i) A liquid medium (DMEM High glucose, FBS+, P/S+) was temperature-controlled in an incubator set at 37° C.

(ii) A cryotube containing cells was taken out from a −80° C. freezer and thawed at once in the incubator set at 37° C.

(iii) A test tube was subjected to a centrifuge to precipitate the cells.

(iv) The supernatant was aspirated, and the liquid medium was added and gently tapped to disperse the cells.

(v) A small amount of the cells-dispersed liquid medium was collected, and the number of cells was observed and counted under a microscope.

(vi) The cells were seeded in three 24-well black plates such that the number of cells was $1\times10^4$ cells per well. The 24-well black plates were placed in an incubator, and the cells were cultured for 24 hours under conditions of 37° C. and 5% $CO_2$.

B. Transfection (i) A lipid nanoparticle-containing solution including an mRNA was concentrated such that the mRNA concentration was 100 ng/20 μL (=0.005 μg/μL).

(ii) A liquid medium (DMEM High glucose, FBS-, P/S-) and FBS were warmed to 37° C., required amounts of the liquid medium and FBS were mixed (FBS concentration of liquid medium at this time: 12.5%), and the prepared liquid medium was filter-sterilized through a 0.22 μm filter.

(iii) The liquid medium supernatant in the 24-well black plates in which the cells were cultured was aspirated and 80 μL per well of the prepared liquid medium was added.

(iv) 20 μL per well of RFW and the lipid nanoparticle-containing solution adjusted to the above concentration was added.

(v) The 24-well black plates were placed in an incubator, and the cells were cultured for 24 hours under conditions of 37° C. and 5% $CO_2$.

C. Evaluation of Protein Expression Effect (Detection of *Gaussia* Luciferase (GLuc))

Evaluation of the protein expression effect was carried out by using *Gaussia* Luciferase Assay Kit manufactured by Thermo Scientific.

(i) The cells cultured in B. (v) above were taken out from the incubator and allowed to stand at room temperature.

(ii) 20 μL of the supernatant in the plates was collected and added to a fresh 96-well white plate.

(iii) 100× Coelenterazine and *Gaussia* Glow Assay Buffer attached to the kit were returned to room temperature and mixed at 1:100 to prepare a solution. The prepared solution was added to the supernatant at 50 μL per well by using a multipipette.

(iv) The plate was shielded from light with aluminum foil, allowed to stand for 10 minutes, and then measured for the amount of luminescence with a plate reader (manufactured by TECAN, Infinite M200) (measurement time: 2 seconds), and the protein expression level was calculated by using the resulting amount of luminescence as an index.

D. Evaluation of Toxicity (CellTiter-Fluor (Registered Trademark) Cell Viability Assay)

(i) The CellTiter-Fluor (registered trademark) Cell Viability (CTF) Assay Reagent was completely thawed in a 37° C. water bath.

(ii) GF-AFC Substrate was uniformly mixed by using a vortex mixer.

(iii) The required amounts of Buffer and GF-AFC Substrate attached to the CTF Assay Reagent (Kit) were mixed at a mixing ratio of 10 mL:10 μL.

(iv) 100 μL per well of the mixed CTF Reagent mixture was added to a 24-well black plate containing the cells cultured in B. (v) above, and the plate was quickly shielded from light with aluminum foil, and then shaken on a plate shaker for 30 seconds.

(v) The plate was placed in an incubator, the 24-well black plate was placed in an incubator, and the cells were cultured for 30 minutes under conditions of 37° C. and 5% $CO_2$.

(vi) The fluorescence intensity was measured with a plate reader (excitation wavelength of 380 nm, fluorescence wavelength of 505 nm). Based on the obtained measurement results, the number of surviving cells was calculated with the fluorescence intensity of cells to which no lipid nanoparticle was added set at 1. When the number of surviving cells was more than 0.80 and 1.00 or less, a rating of double-circle (excellent) was given, when the number was more than 0.50 and 0.80 or less, a rating of circle (good) was given, when the number was more than 0.20 and 0.50 or less, a rating of triangle (fair) was given, and when the number was 0.20 or less, a rating of X-mark (poor) was given.

[In Vivo Animal Experiment]

An experiment was carried out in mice in order to evaluate lipid nanoparticles encapsulating an mRNA. By injecting mice with a solution including lipid nanoparticles to transfect the mice and measuring the amount of a predetermined protein produced, the performance of the lipid nanoparticles used can be evaluated. Hereinafter, the procedure of the experiment will be shown.

A. Preparation of Lipid Nanoparticle-Containing Solution

By using lipids (Ib), (Ik), and (Il) of Examples 2, 11, and 12, lipid nanoparticle-containing solutions for the in vivo animal experiment were prepared. Lipid nanoparticle-containing solutions were prepared by the same method as in the above [Production of lipid nanoparticle (LNP)] except that in (ii) of the lipid solution preparation method described in the above [Production of lipid nanoparticle (LNP)], a lipid solution was produced by mixing in such a way as to provide main lipid/helper lipid/cholesterol=45/10/45 and further adding a polyethylene glycol-modified lipid (PEG2000-DMG) to the resulting mixed solution in such a way as to reach 1.5 mol %.

In addition, for the lipid nanoparticle-containing solution formed from lipid (Ib) of Example 2, a lipid nanoparticle-containing solution produced without adding a polyethylene glycol-modified lipid was also used for in vivo animal experiment for comparison.

B. Preparation of Solution for Administration

The lipid nanoparticle-containing solutions formed from lipids (Ib), (Ik), and (Il) of Examples 2, 11, and 12 were concentrated to the target concentration (0.03125 μg/μL, in terms of mRNA) by using a centrifugal ultrafiltration filter unit (Amicon Ultra-2, 10 k) (6,000×g). Next, a 1.5 M sucrose solution was added to the concentrated lipid nanoparticle-containing solution such that the final sucrose concentration was 0.3 M, to obtain a solution for administration.

C. Administration and Measurement

50 μL (1.25 μg/mouse, in terms of amount of mRNA) of the solution for administration was intramuscularly administered to the left hind leg of mice. Then, 10 minutes before the predetermined time (2, 4, 6, 8, or 24 hours) elapsed after administration, a 30 mg/mL luciferin solution/PBS(−) was intraperitoneally administered to the mice at a dose of 150 mg/kg body. 10 Minutes after administration of the luciferin solution, the amount of luminescence at a predetermined time after administration was measured under isoflurane anesthesia with an in vivo imaging system (manufactured by Xenogen, IVIS) to calculate the protein expression level.

<Evaluation Results>

(1) Evaluation Results of Lipid Nanoparticles Containing siRNA

Evaluation results of lipid nanoparticles containing an siRNA PP 9T obtained by using the lipids of the Examples and the Comparative Examples are shown in Tables 1 and 2.

TABLE 1

| | First amino acid-second amino acid | Lipid | Particle size (nm) | PDI | Zeta potential (mV) | GFP Assay | Encapsulation rate (%) | CCK Assay | LDH Assay |
|---|---|---|---|---|---|---|---|---|---|
| Example 1 | Asp-Arg | 1a | 116.5 | 0.169 | 6.98 | 28 | 99 | ◎ | ◎ |
| Example 2 | Glu-Arg | 1b | 119.7 | 0.099 | 9.59 | 24 | 99 | ◎ | ◎ |

TABLE 1-continued

| | First amino acid-second amino acid | Lipid | Particle size (nm) | PDI | Zeta potential (mV) | GFP Assay | Encapsulation rate (%) | CCK Assay | LDH Assay |
|---|---|---|---|---|---|---|---|---|---|
| Example 3 | His-Arg | 1c | 96.0 | 0.157 | 15.4 | 22 | 100 | — | ○ |
| Example 4 | Ser-Arg | 1d | 103.6 | 0.101 | 15.7 | 7 | 100 | ○ | Δ |
| Example 5 | Thr-Arg | 1e | 109.2 | 0.084 | 15.2 | 22 | 100 | — | ◎ |
| Example 6 | Met-Arg | 1f | 125.9 | 0.118 | 21.9 | 40 | 100 | — | ○ |
| Example 7 | Asp-Lys | 1g | 94.2 | 0.159 | 8.28 | 28 | 100 | ○ | — |
| Example 8 | Glu-Lys | 1h | 162.5 | 0.147 | 19.1 | 47 | 100 | ◎ | — |
| Example 9 | Glu-His | 1i | 107.6 | 0.093 | 24.6 | 56 | 84 | ◎ | — |
| Example 10 | Thr-Arg | 1j | 103.6 | 0.095 | 36.8 | 11 | 98 | — | — |
| Example 11 | Glu-Arg | 1k | 108.1 | 0.078 | 19.5 | 32 | 99 | — | — |
| Example 12 | Glu-Arg | 1l | 105.9 | 0.034 | 22.4 | 28 | 99 | — | — |

*: "—" in the table indicates not measured.

TABLE 2

| | First amino acid-second amino acid | Lipid | Particle size (nm) | PDI | Zeta potential (mV) | GFP Assay | Encapsulation rate (%) | CCK Assay | LDH Assay |
|---|---|---|---|---|---|---|---|---|---|
| Comparative Example 1 | Thr | CEa | 288.0 | 0.106 | 27.8 | — | — | — | — |
| Comparative Example 2 | Guanidino group-containing compound | CEb | 117.1 | 0.085 | −7.75 | 97 | 95 | — | ◎ |
| Comparative Example 3 | Guanidino group-containing compound | CEc | 137.0 | 0.329 | −7.66 | 102 | 95 | — | Δ |
| Comparative Example 4 | Lys | CEd | 147.5 | 0.063 | 26.5 | 86 | 99 | — | — |
| Comparative Example 5 | Lys | CEe | 324.5 | 0.731 | 50.8 | — | 100 | — | — |
| Comparative Example 6 | Lys | CEf | 212.1 | 0.022 | 27.5 | — | 99 | — | — |
| Comparative Example 7 | Lys | CEg | 149.8 | 0.021 | 21.0 | — | 99 | — | — |
| Comparative Example 8 | Lys | CEh | 233.1 | 0.187 | 29.7 | — | 100 | — | — |
| Comparative Example 9 | Lys | CEi | 759.4 | 0.508 | 32.7 | — | 100 | — | — |
| Comparative Example 10 | Asp-Arg | CEj | 109.9 | 0.225 | 14.8 | 70 | — | ◎ | — |
| Comparative Example 11 | Asp-Arg | CEk | 94.4 | 0.202 | 17.6 | 95 | — | ◎ | — |
| Comparative Example 12 | Met | CEl | 310.6 | 0.132 | 28.1 | — | — | — | — |

*: "—" in the table indicates not measured.

As shown in Table 1, the lipid nanoparticles obtained from the lipids of Examples 1 to 12 have a lower particle size and PDI. When the particle size and PDI of a lipid nanoparticle is low as described above, the lipid nanoparticle can be easily delivered to a target cell or tissue. Specifically, because the particle size and PDI are low, for example, when the target tissue is a tumor, the lipid nanoparticle tends to be smaller than the pore size of the blood vessels of the tumor, making it possible for the lipid nanoparticle to easily reach the tissue.

In addition, the lipid nanoparticles obtained from the lipids of Examples 1 to 12 have a low electric charge as measured in Tris-HCl at pH 7.4. The blood of the living body is in an environment of about pH 7.4, and in such an environment, when the lipid nanoparticles are strongly cationic (have high electric charge), non-specific adsorption or immune reaction easily occurs, or the lipid nanoparticle particles easily have toxicity or are easily metabolized before reaching a target cell or tissue. The lipid nanoparticles obtained from the lipids of Examples 1 to 12 have a low electric charge (close to 0 mV) at pH 7.4, and thus can suppress concern about toxicity and metabolism.

In addition, as shown in Table 1, the lipid nanoparticles obtained from the lipids of Examples 1 to 12 have a high siRNA encapsulation rate. Therefore, a lipid nanoparticle encapsulating an siRNA can be efficiently obtained.

Further, as shown in the results of the GFP assay and the cell experiment on toxicity in Table 1, the lipid nanoparticles obtained from the lipids of Examples 1 to 12 have a low value as the GFP assay result. Therefore, it can be seen that the green fluorescent protein gene (EGFP) in HT1080-EGFP (human/fibrosarcoma) cells is effectively knocked down, that is, the lipid nanoparticles reach the inside of the cells and the siRNA inhibits the expression of the gene. Therefore, by using the lipids of Examples 1 to 12, an siRNA can be effectively delivered into a cell.

In addition, as shown in Examples 1 to 6 in Table 1, it can be seen that the lipids whose first amino acid is a hydrophilic amino acid (Examples 1 to 5) have a better GFP assay result than the lipid whose first amino acid is not hydrophilic (Example 6). Therefore, the lipids whose first amino acid is a hydrophilic amino acid can more effectively deliver an introduction compound such as a nucleic acid to a target cell, tissue, or the like in vivo.

In addition, the CCK assay and the LDH assay shown in Table 1 are evaluations of cytotoxicity, and it can be seen that the lipids of Examples 1 to 3, 5, and 6 also have low cytotoxicity. In order to introduce an siRNA into a cell, a relatively larger amount of a lipid is used than in the case of introducing an mRNA into a cell, and the lipids of Examples 1 to 3, 5, and 6 can reduce the toxicity even when a relatively larger amount of the lipid is applied to a cell.

In addition, the lipids of Examples 10 to 12 are lipids that are different in the lipophilic region from the lipids of Examples 1 to 9. From the results of Examples 5 and 10, it can be seen that even when the number of unsaturated bonds in the hydrocarbon group in the lipophilic region is changed, good results can be obtained. Further, from the results of Examples 2, 11, and 12, it can be seen that even when the number of carbon atoms in the hydrocarbon group in the lipophilic region is changed, if the number is in a desired range (specifically, the number of carbon atoms in the hydrocarbon group of $R^1$ in formula (I) is 32 to 48), good results can be obtained.

Subsequently, Comparative Examples 1 to 4 and 12 in Table 2 show results of using lipids each having the same lipophilic region and a hydrophilic region consisting of one amino acid different thereamong. As shown in Comparative Example 1 in Table 2, the lipid nanoparticles obtained from the lipids of Comparative Examples 1 and 12 have large particle diameter and PDI values. Therefore, it can be seen that it is difficult for a lipid having one amino acid as the hydrophilic region as in Comparative Examples 1 and 12 to allow an introduction compound to reach a target cell or tissue. On the other hand, as shown in Comparative Examples 2 to 4 in Table 2, the lipid nanoparticles obtained from the lipids of Comparative Examples 2 to 4 do not have larger particle diameter and PDI values than the lipid nanoparticle obtained from the lipid of Comparative Example 1, but has a larger value as the GFP assay result. Therefore, the lipids in which the hydrophilic region is one amino acid, but a side chain of the amino acid is basic as in Comparative Examples 2 to 4 can be improved in particle size and PDI as compared with the lipids in which a side chain of the amino acid is not basic (Comparative Examples 1 and 12), but it can be seen that it is difficult for the former lipids to efficiently introduce an introduction compound into a cell. In addition, it can be seen that a lipid having a hydrophilic region consisting of two amino acids, as shown in each Example, is effective.

In addition, Comparative Examples 5 to 10 in Table 2 show results of lipids in which the number of carbon atoms in the hydrocarbon group in the lipophilic region was changed from that in the lipid of Comparative Example 4. Specifically, the lipid of Comparative Example 5, in which the number of carbon atoms in the hydrocarbon group in the lipophilic region is 20, the lipid of Comparative Example 8, in which the number of carbon atoms therein is 22, and the lipid of Comparative Example 9, in which the number of carbon atoms therein is 28, are much worse in one or both of particle size and PDI than the lipid of Comparative Example 4, in which the number of carbon atoms therein is 36. On the other hand, it is recognized that the lipid of Comparative Example 6, in which the number of carbon atoms therein is 32, and the lipid of Comparative Example 7, in which the number of carbon atoms therein is 44, are comparable in particle size and PDI to the lipid of Comparative Example 4. Therefore, from the results of Comparative Examples 4 to 9 in Table 2, it can be seen that when the number of carbon atoms in the hydrocarbon group in the lipophilic region is outside the range of 32 to 48, either one or both of the particle size and PDI are much worse.

Further, the lipids of Comparative Examples 8 and 9 are lipids in which there is a difference (10 or 16) in the number of carbon atoms between the branched chains of the branched hydrocarbon groups in the lipophilic region. The lipids of Comparative Examples 8 and 9 are worse in particle size and PDI than the lipids in which there is no difference in the number of carbon atoms between the branched chains as in the lipids of Comparative Examples 6 and 7. Therefore, when the hydrocarbon group in the lipophilic region is branched, it can be seen that better results can be obtained when the difference in the number of carbon atoms between the branched hydrocarbon groups is smaller.

Further, from the results of using the lipid of Example 1 in Table 1 and the lipids of Comparative Examples 10 and 11 in Table 2, it can be seen that in the binding portion between the lipophilic region and the hydrophilic region, direct binding between the lipophilic region, which is a hydrocarbon group, and the hydrophilic region, which is an amino acid moiety, yields a better result than forming binding via an ester group or an amide group.

(2) Evaluation Results of Lipid Nanoparticles Containing mRNA

Evaluation results of lipid nanoparticles containing an mRNA produced by using the lipids of Examples 1, 2, and 5 are shown in Table 3.

TABLE 3

| | First amino acid-second amino acid | Lipid | Cell species | Particle size (nm) | PDI | Zeta potential (mV) | Protein expression level | Encapsulation rate (%) | CTF Assay |
|---|---|---|---|---|---|---|---|---|---|
| Example 1 | Asp-Arg | 1a | HEK293T<br>NIH3T3 | 97.8 | 0.114 | 4.2 | 100,000<br>5,000 | 98 | ◎ |
| Example 2 | Glu-Arg | 1b | HEK293T<br>NIH3T3 | 122.3 | 0.159 | 5.0 | 800,000<br>25,000 | 97 | ◎ |
| Example 5 | Thr-Arg | 1e | HEK293T<br>NIH3T3 | 91.0 | 0.069 | 14.3 | 100,000<br>60,000 | 100 | ◎ |
| Reference Example 1 | — | r1 | HEK293T<br>NIH3T3 | 64.4 | 0.232 | −4.3 | 320,000<br>7,000 | 93 | ◎ |

The lipid nanoparticles containing an mRNA obtained by using the lipids of Examples 1, 2, and 5 have a low particle size and PDI, as do the lipid nanoparticles containing an siRNA described above, and this allows the lipid nanoparticles to easily reach a target cell or tissue.

In addition, the lipid nanoparticles obtained from the lipids of Examples 1, 2, and 5 had a low electric charge as measured in Tris-HCl at pH 7.4, and this can suppress the occurrence of non-specific adsorption and immune reaction in vivo.

In addition, as shown in Table 3, the lipid nanoparticles obtained from the lipids of Examples 1, 2, and 5 have a high mRNA encapsulation rate. Therefore, a lipid nanoparticle encapsulating an mRNA can be efficiently obtained.

Further, as shown in the results of the protein expression level and the CTF assay (evaluation of toxicity) in Table 3, it can be seen that the lipid nanoparticles obtained from the lipids of Examples 1, 2, and 5 expressed the desired protein at a certain level, that is, the lipid nanoparticles reach the inside of the cell and the protein is expressed by the mRNA contained in the lipid nanoparticles. Therefore, the lipids of Examples 1, 2, and 5 can effectively deliver an mRNA into a cell.

In addition, as shown in Table 3, the lipids of Examples 1, 2, and 5 have a large number of surviving cells in the cell experiment. Therefore, it can be seen that the lipids of Examples 1, 2, and 5 also have low cytotoxicity when used to deliver an mRNA to a target cell or tissue.

Table 3 also shows an example using lipid (r1) of Reference Example 1, which is used as a lipid for an mRNA vaccine, and it can be seen that the results of using the lipids of Examples 1, 2, and 5 are better than the result of using the lipid of Reference Example 1.

(3) Evaluation Results of In Vivo Animal Experiment

Subsequently, evaluation results of lipid nanoparticles for an in vivo animal experiment produced by using the lipids of Examples 2, 11, and 12 are shown in Table 4.

TABLE 4

| | First amino acid-second amino acid | Lipid | Presence or absence of PEG-modified lipid | Particle size (nm) | PDI | Zeta potential (mV) | Protein expression level | Encapsulation rate (%) |
|---|---|---|---|---|---|---|---|---|
| Example 2 | Glu-Arg | 1b | Absent | 119.7 | 0.10 | 3.92 | 13,000 | 91.3 |
| | | | Present | 92.8 | 0.19 | 16.71 | 130,000 | 93.2 |
| Example 11 | Glu-Arg | 1k | Present | 73.5 | 0.21 | 10.89 | 80,000 | 93.7 |
| Example 12 | Glu-Arg | 1l | Present | 79.6 | 0.16 | 4.69 | 1,700,000 | 93.5 |

From the results of Example 2, it can be seen that the presence of a polyethylene glycol-modified lipid when preparing the lipid nanoparticle-containing solution can greatly improve the protein expression level. In addition, as can be seen from the results of Examples 11 and 12, it can be seen that even when the lipid nanoparticle-containing solutions produced from the lipids of Examples 11 and 12 are used, the protein expression level can be greatly improved.

Therefore, it is assumed that the lipid of the present embodiment can obtain a better property by allowing a molecule other than the lipid of the present embodiment to be present when preparing a lipid nanoparticle-containing solution.

INDUSTRIAL APPLICABILITY

According to the present invention, it is possible to provide a lipid and a composition that can effectively deliver an introduction compound such as a nucleic acid to the cytoplasm.

The invention claimed is:

1. A lipid represented by the following formula (I):

(I)

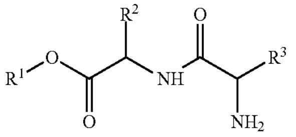

wherein $R^1$ is a hydrocarbon group having 32 to 48 carbon atoms, $R^2$ is a side chain of one arbitrary amino acid or a side chain of a derivative of the arbitrary amino acid, and $R^3$ is a side chain of a basic amino acid or a side chain of a derivative of the basic amino acid, wherein $R^1$ is represented by the following formula (II):

(II)

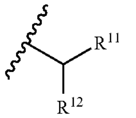

wherein $R^{11}$ is a hydrocarbon group having a carbon atoms, and $R^{12}$ is a hydrocarbon group having b carbon atoms, where a and b satisfy $31 \leq a + b \leq 47$ and $1 \leq b - a \leq 18$.

2. The lipid according to claim 1, wherein $R^2$ is a side chain of a hydrophilic amino acid or a side chain of a derivative of the hydrophilic amino acid.

3. The lipid according to claim 1, wherein $R^2$ is a side chain of an amino acid of aspartic acid, glutamic acid, histidine, serine, threonine, or derivatives thereof.

4. The lipid according to claim 1, wherein $R^2$ is a side chain of an amino acid of aspartic acid, glutamic acid, histidine, threonine, or derivatives thereof.

5. The lipid according to claim 1, wherein $R^3$ is a side chain of an amino acid of lysine, histidine, arginine, or derivatives thereof.

6. The lipid according to claim 5, wherein $R^3$ is a side chain of arginine or a side chain of a derivative of arginine.

7. The lipid according to claim 1, wherein $R^{11}$ is a linear hydrocarbon group, and $R^{12}$ is a linear hydrocarbon group.

8. The lipid according to claim 1, wherein the lipid is represented by any one of the following formulas (Ia) to (II):

(Ia)
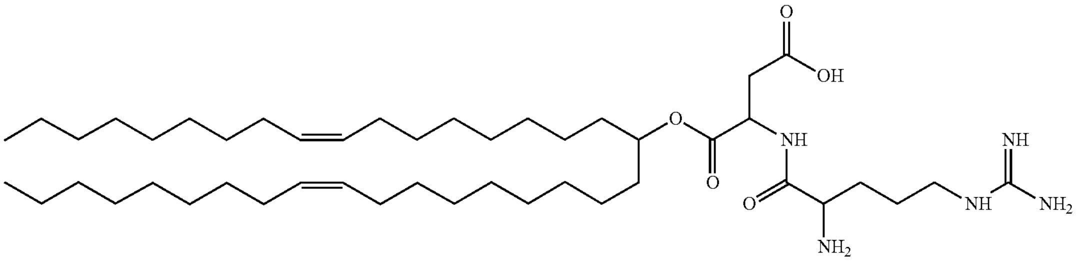
(Ib)
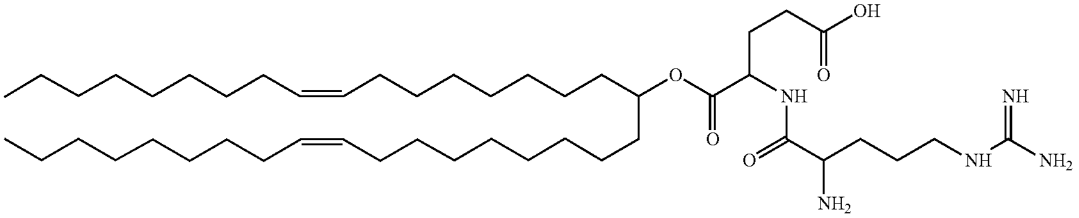
(Ic)
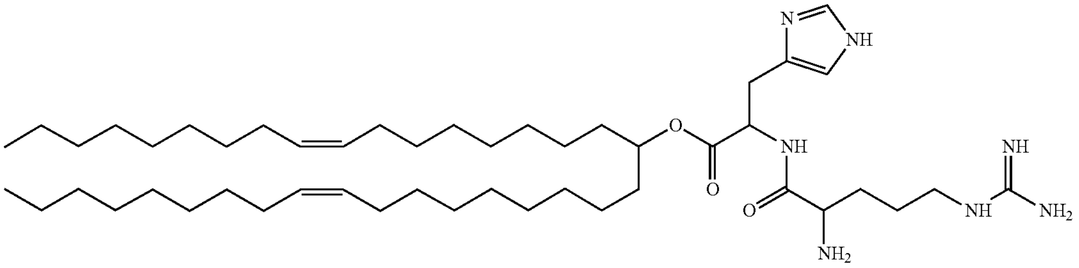
(Id)
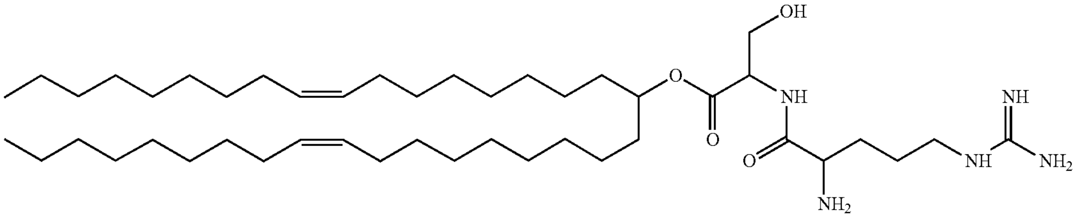
(Ie)
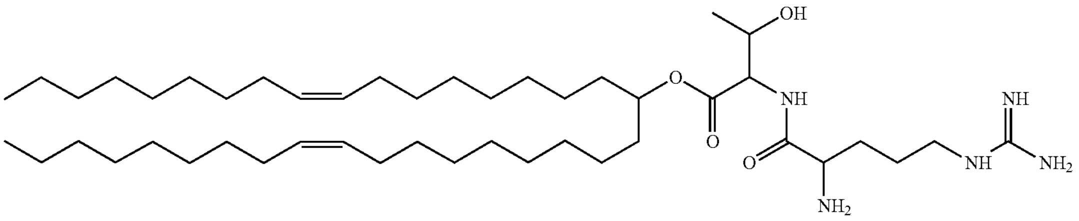
(If)
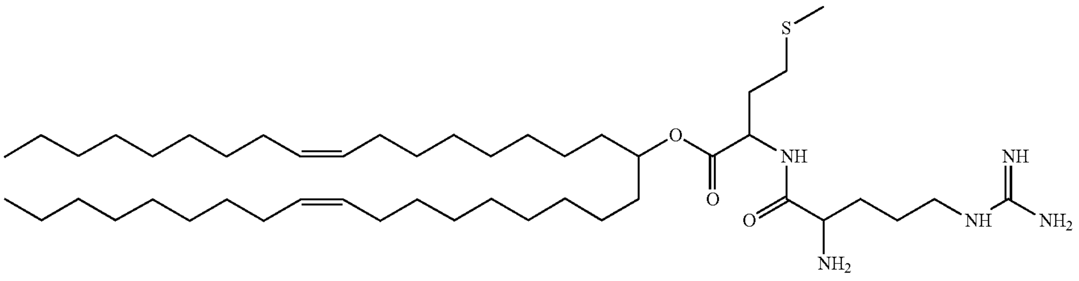

-continued
(Ig)
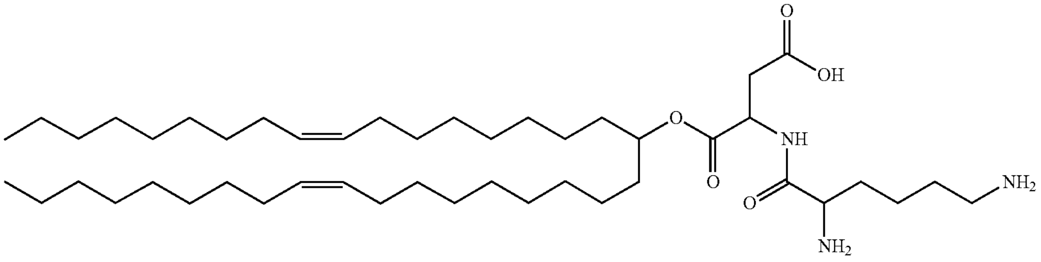
(Ih)
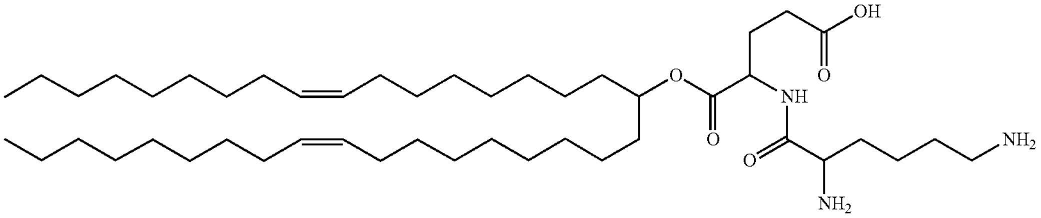
(Ii)
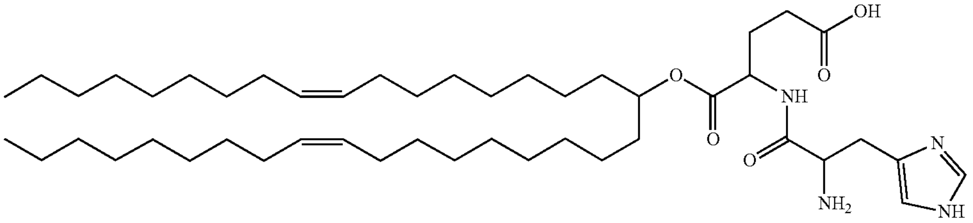
(Ij)
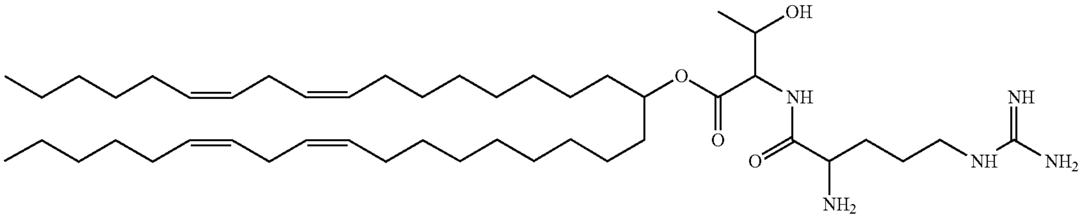
(Ik)
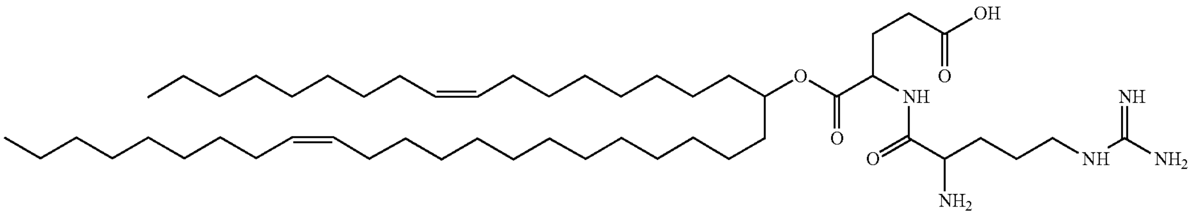
(Il)
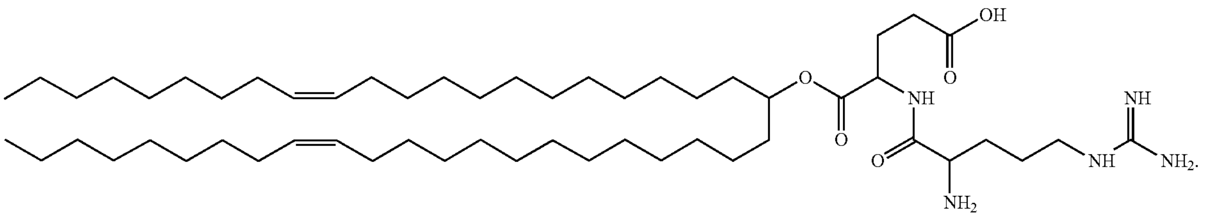

9. The lipid according to claim 1, wherein the lipid is for intracellular introduction of an introduction compound.

10. The lipid according to claim 9, wherein the introduction compound is a nucleic acid.

11. The lipid according to claim 10, wherein the nucleic acid is a nucleic acid having a target gene expression-suppressing action using RNA interference (RNAi) or is an mRNA.

12. The lipid according to claim 11, wherein the nucleic acid is an siRNA or an mRNA.

13. A composition of the lipid according to claim 1 and an introduction compound.

14. The composition according to claim 13, wherein a plurality of the lipids assemble to form a lipid nanoparticle, and the introduction compound is encapsulated in the lipid nanoparticle.

15. The lipid according to claim 2, wherein $R^3$ is a side chain of an amino acid of lysine, histidine, arginine, or derivatives thereof.

16. The lipid according to claim 3, wherein $R^3$ is a side chain of an amino acid of lysine, histidine, arginine, or derivatives thereof.

17. The lipid according to claim 4, wherein $R^3$ is a side chain of an amino acid of lysine, histidine, arginine, or derivatives thereof.

18. The lipid according to claim 2, wherein the lipid is represented by any one of the following formulas (Ia) to (II):

(Ia)

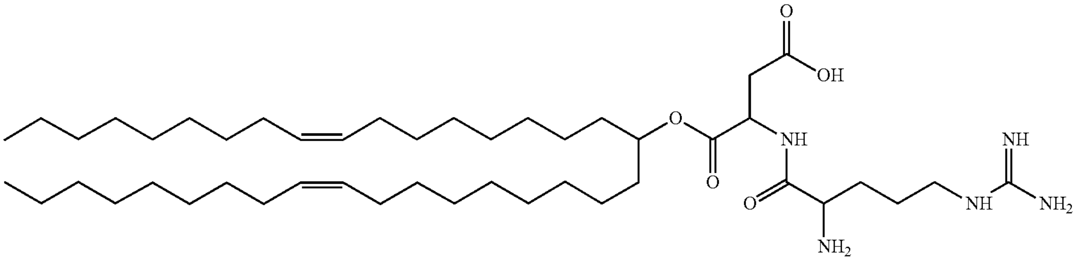

(Ib)

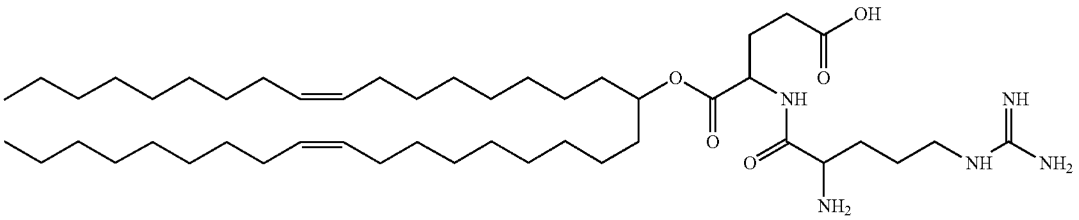

(Ic)

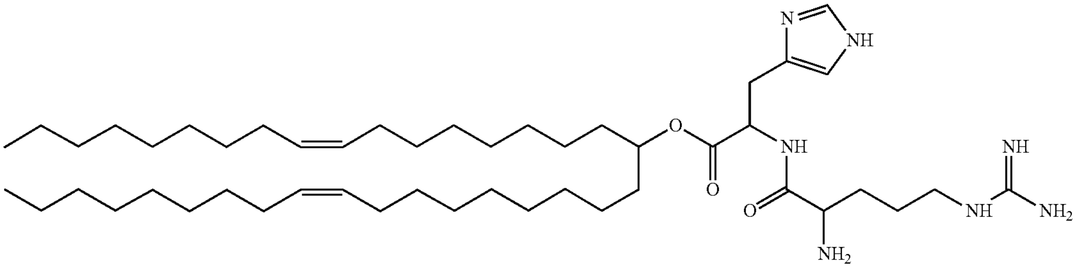

(Id)

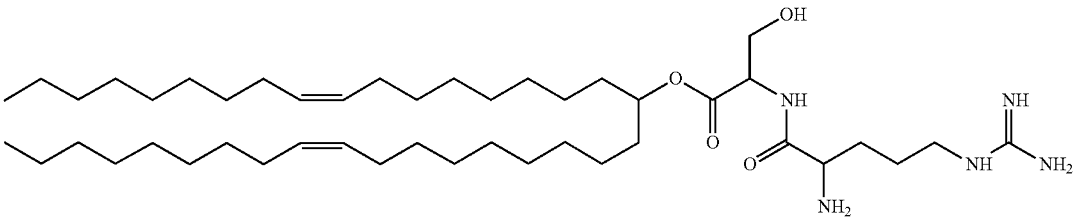

(Ie)

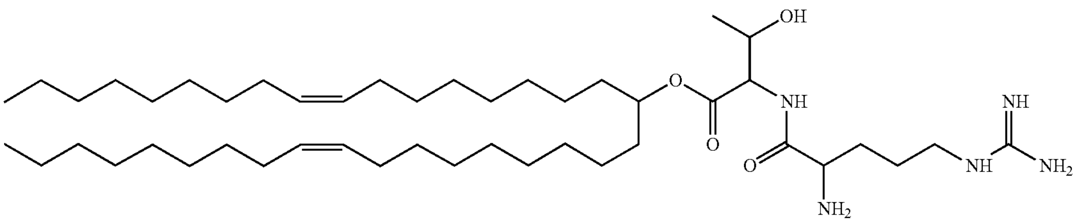

-continued
(If)
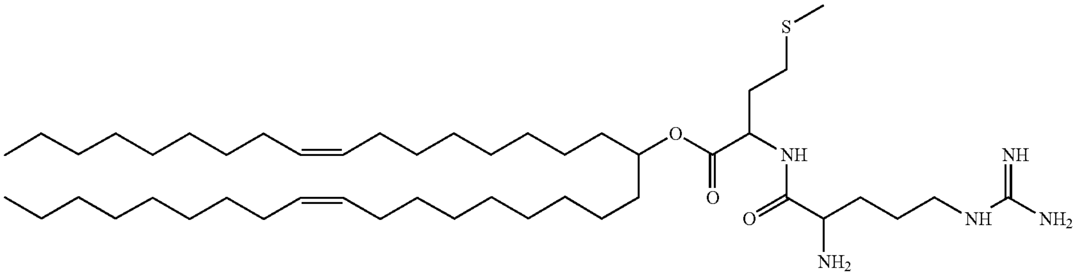
(Ig)
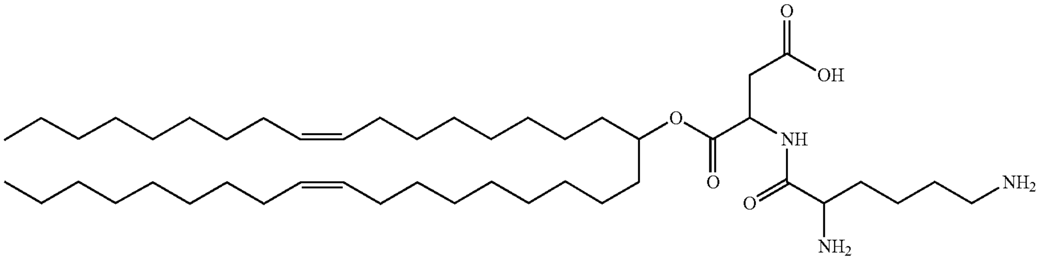
(Ih)
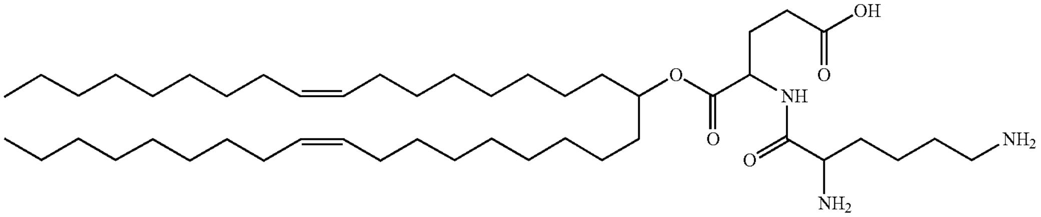
(Ii)
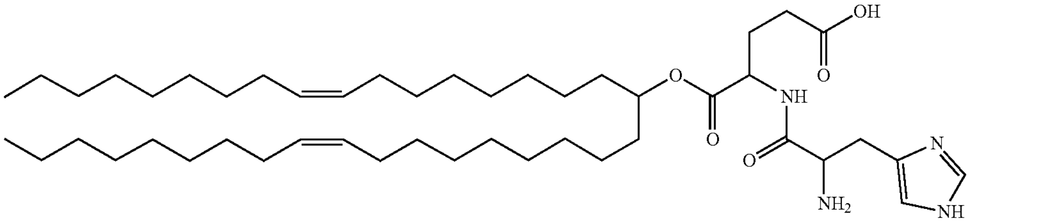
(Ij)
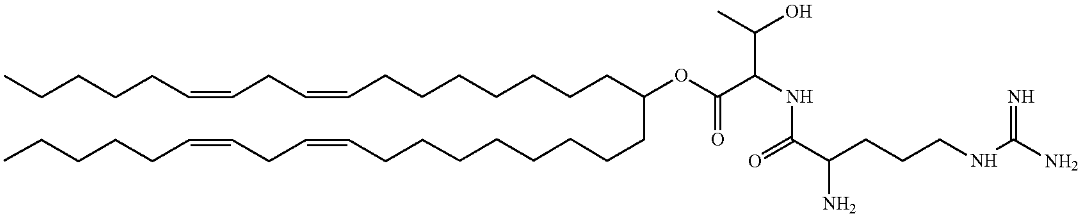
(Ik)
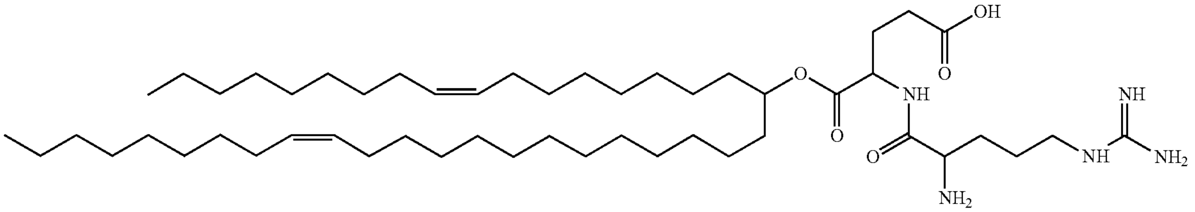

-continued
(II)
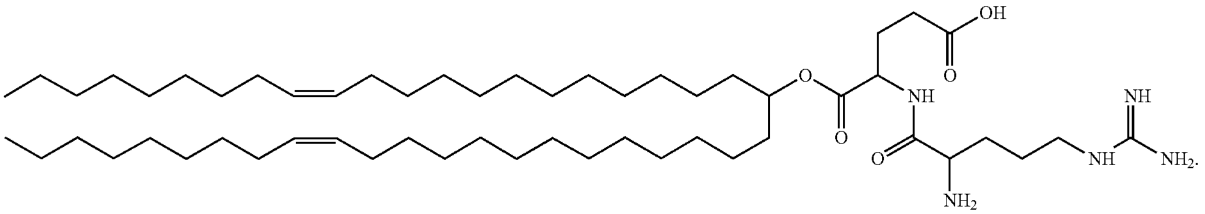
19. The lipid according to claim 3, wherein the lipid is represented by any one of the following formulas (Ia) to (II):
(Ia)
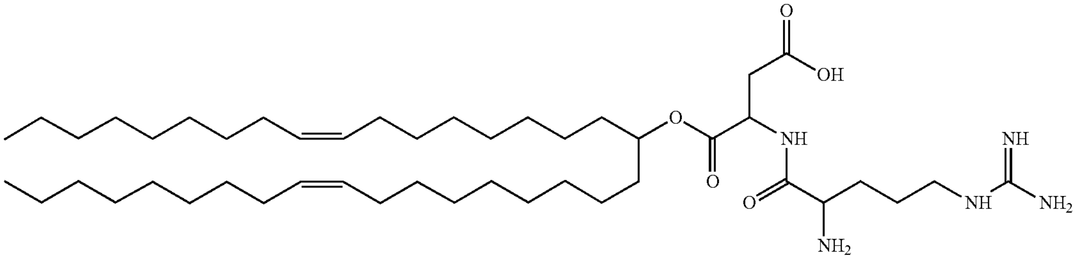
(Ib)
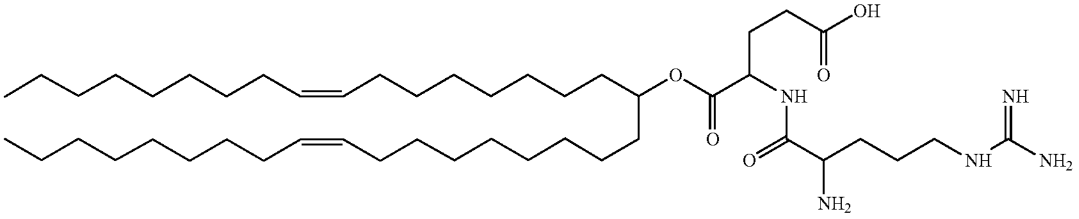
(Ic)
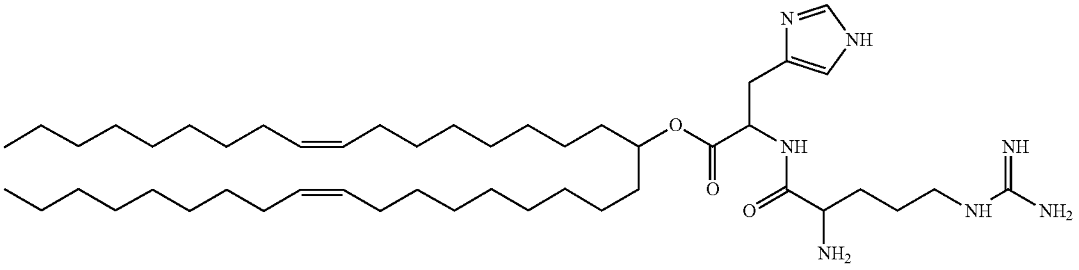
(Id)
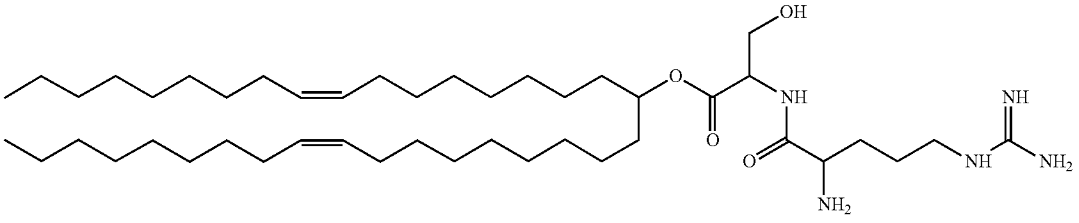
(Ie)
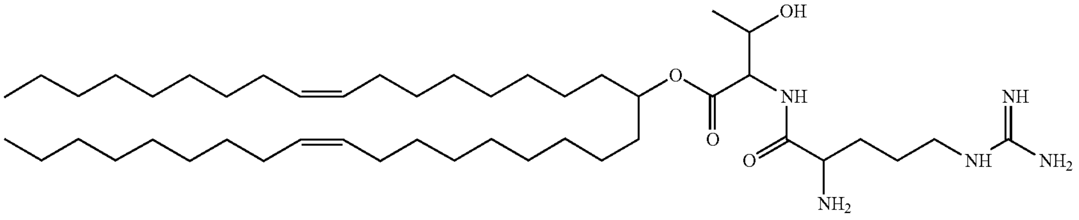

-continued
(If)
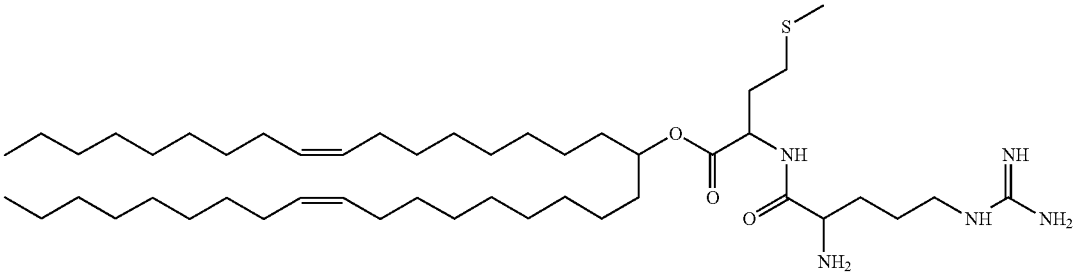
(Ig)
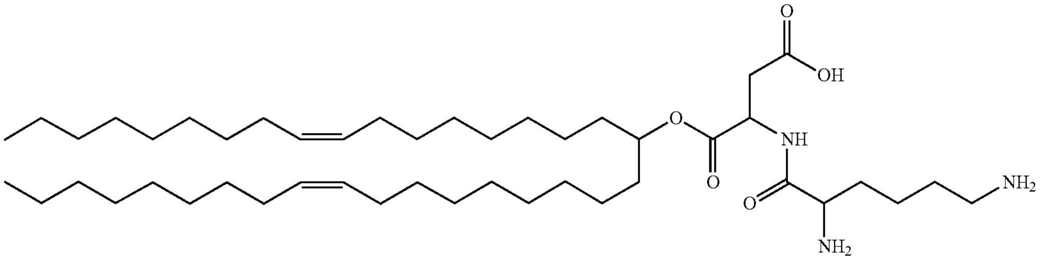
(Ih)
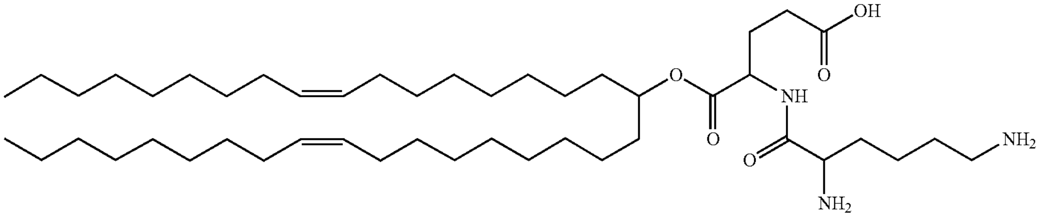
(Ii)
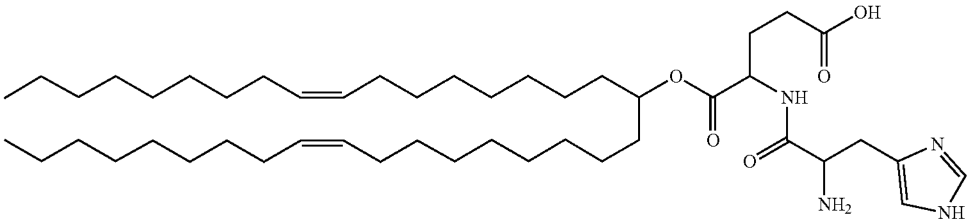
(Ij)
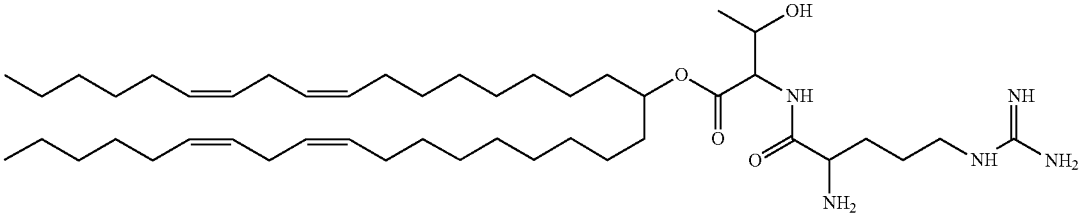
(Ik)
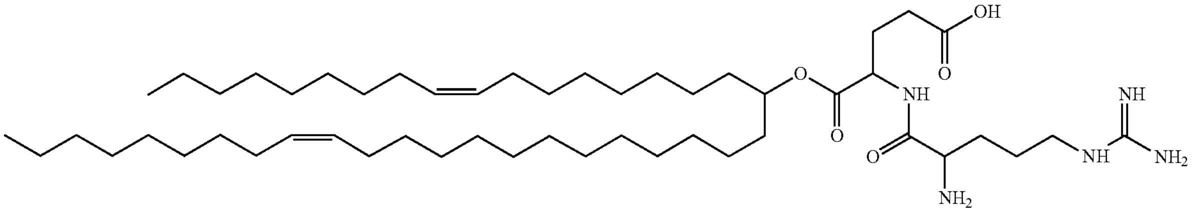

-continued
(Il)
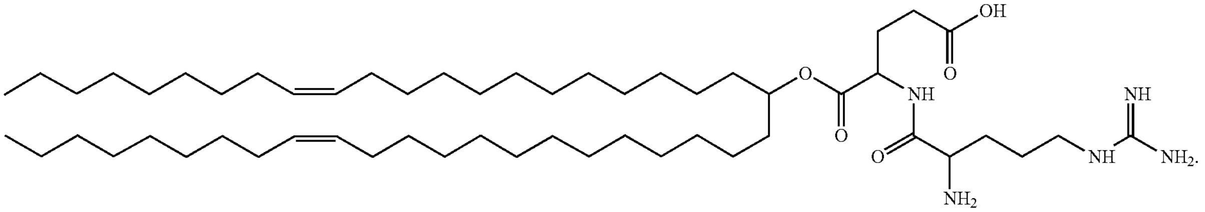
20. The lipid according to claim 4, wherein the lipid is represented by any one of the following formulas (Ia) to (Il):
(Ia)
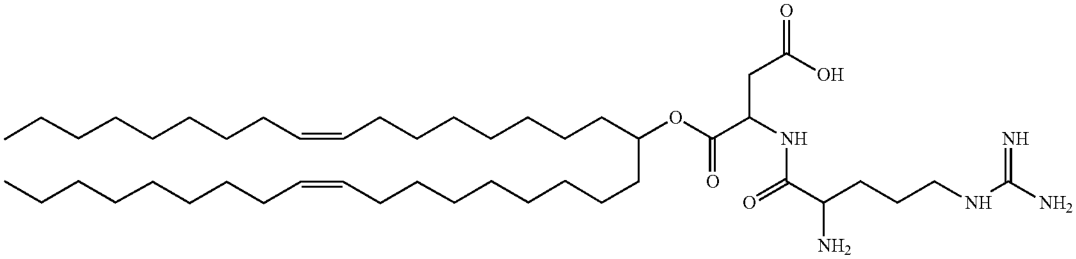
(Ib)
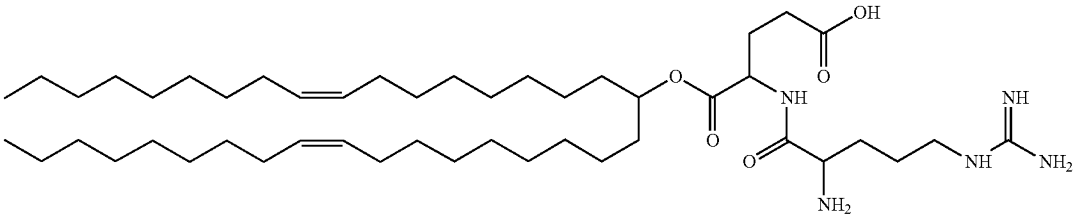
(Ic)
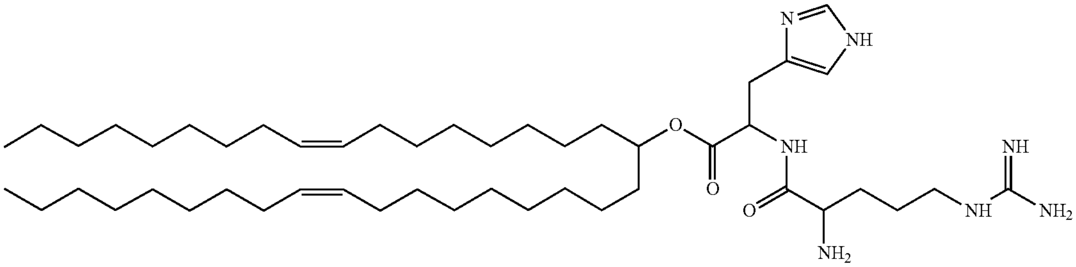
(Id)
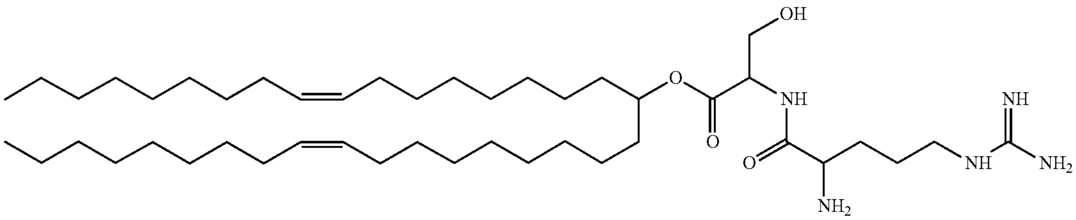
(Ie)
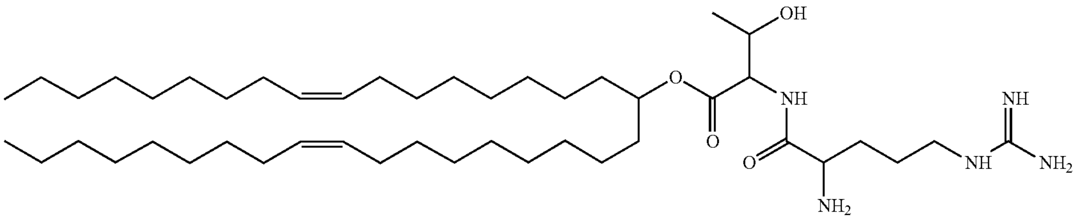

-continued
(If)
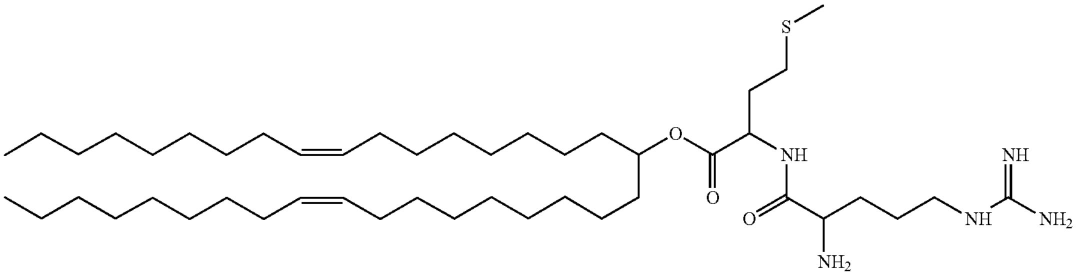
(Ig)
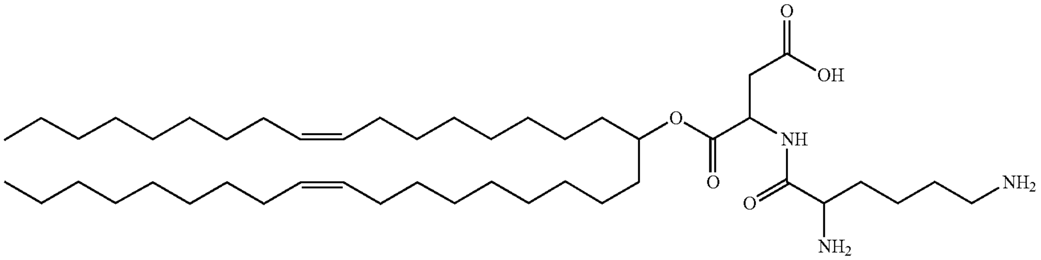
(Ih)
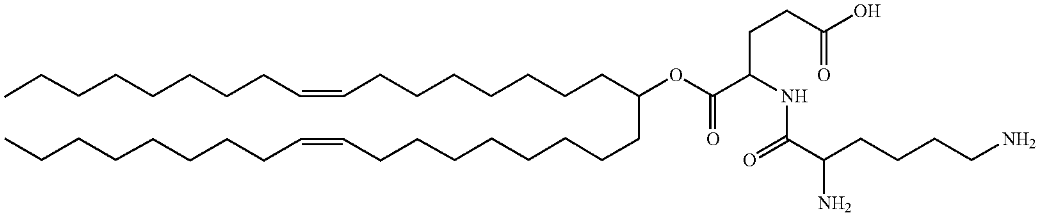
(Ii)
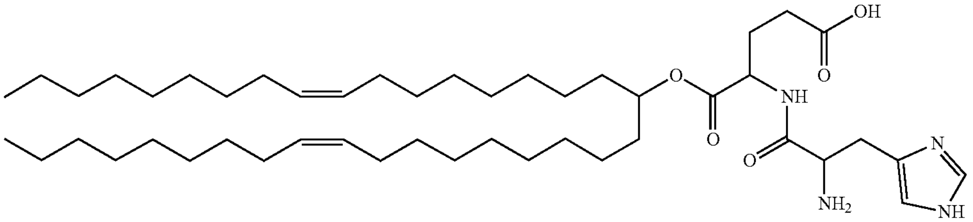
(Ij)
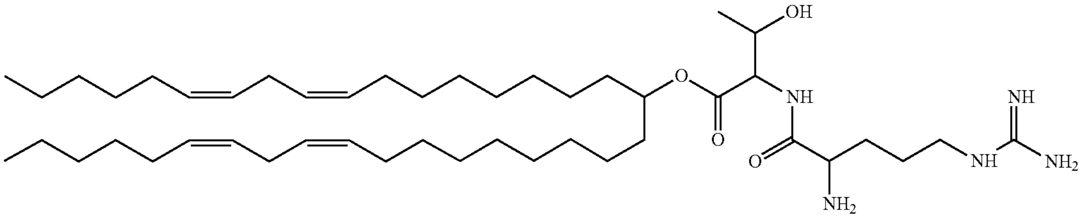
(Ik)
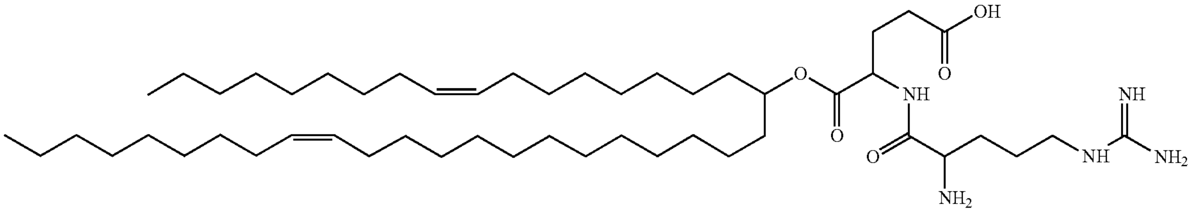

-continued
(II)
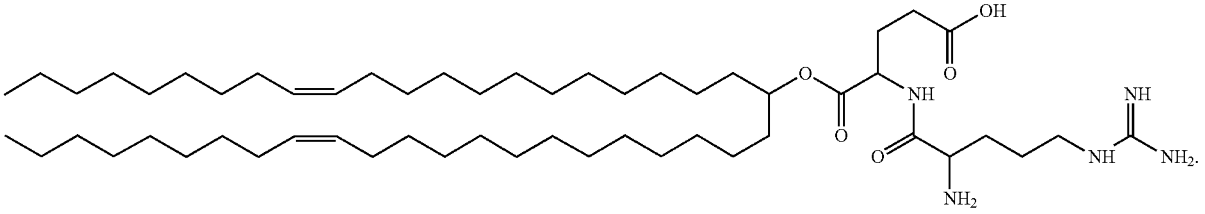
* * * * *